US012690861B2

(12) United States Patent
Kawayoke et al.

(10) Patent No.: US 12,690,861 B2
(45) Date of Patent: Jul. 28, 2026

(54) CLIP UNIT, CLIP DELIVERY DEVICE, AND CLIP RELEASE METHOD

(71) Applicant: OLYMPUS MEDICAL SYSTEMS CORP., Tokyo (JP)

(72) Inventors: Shoichiro Kawayoke, Hino (JP); Yoshimi Kuroda, Funabashi (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 280 days.

(21) Appl. No.: 18/363,303

(22) Filed: Aug. 1, 2023

(65) Prior Publication Data

US 2024/0041449 A1     Feb. 8, 2024

Related U.S. Application Data

(60) Provisional application No. 63/370,339, filed on Aug. 3, 2022.

(51) Int. Cl.
*A61B 17/04*         (2006.01)

(52) U.S. Cl.
CPC .. *A61B 17/0487* (2013.01); *A61B 2017/0488* (2013.01)

(58) Field of Classification Search
CPC .... A61B 17/0487; A61B 17/10; A61B 17/083
See application file for complete search history.

(56) References Cited

U.S. PATENT DOCUMENTS

| | | | | |
|---|---|---|---|---|
| 4,337,774 A | * | 7/1982 | Perlin | A61B 17/122 24/536 |
| 4,822,348 A | * | 4/1989 | Casey | A61F 6/206 606/157 |
| 4,932,955 A | * | 6/1990 | Merz | A61B 17/1227 606/158 |
| 5,049,153 A | * | 9/1991 | Nakao | A61B 17/10 606/151 |
| 5,921,996 A | * | 7/1999 | Sherman | A61B 17/122 606/157 |
| 2002/0045909 A1 | * | 4/2002 | Kimura | A61B 17/083 606/151 |
| 2005/0049618 A1 | * | 3/2005 | Masuda | A61B 17/1285 606/151 |
| 2008/0255427 A1 | * | 10/2008 | Satake | A61B 17/08 606/205 |
| 2008/0312665 A1 | * | 12/2008 | Shibata | A61B 17/10 606/142 |

(Continued)

FOREIGN PATENT DOCUMENTS

| | | |
|---|---|---|
| JP | 6284009 B2 | 2/2018 |
| JP | 6865270 B2 | 4/2021 |

*Primary Examiner* — Alexander J Orkin
(74) *Attorney, Agent, or Firm* — Schwegman Lundberg & Woessner, P.A.

(57)          ABSTRACT

A clip unit for a treatment tool is disclosed herein. The clip unit comprising a first arm that includes a first rotation portion, the first arm rotating around the first rotation portion as a center of rotation. The clip unit further comprising a second arm that includes a second rotation portion that is connected to the first rotation portion, the second arm rotating around the second rotation portion as a center of rotation. The first rotation portion and the second rotation portion are configured to lock a relative rotation of the first arm and the second arm.

14 Claims, 37 Drawing Sheets

(56)               References Cited

U.S. PATENT DOCUMENTS

| | | | |
|---|---|---|---|
| 2013/0053862 A1* | 2/2013 | Tulleken | A61B 17/11 |
| | | | 606/108 |
| 2013/0245653 A1* | 9/2013 | Litherland | A61B 17/128 |
| | | | 606/158 |
| 2015/0057684 A1* | 2/2015 | Zieris | A61B 17/083 |
| | | | 606/151 |
| 2020/0100791 A1* | 4/2020 | Tsuchiya | A61B 17/122 |

* cited by examiner

CLIP UNIT, CLIP DELIVERY DEVICE, AND CLIP RELEASE METHOD

CROSS-REFERENCE TO RELATED APPLICATIONS

The present application claims priority based on U.S. Patent Provisional Application No. 63/370,339 provisionally filed in the United States on Aug. 3, 2022, the contents of which are incorporated herein by reference.

TECHNICAL FIELD

The present disclosure relates to a to a clip unit, a clip delivery device, and a clip release method.

BACKGROUND

In endoscopic treatment, endoscopic treatment tools such as a clip unit that can ligate the resected area after treatment to stop bleeding are used. The clip unit includes a clip that pinches the resected portion or the like with a plurality of arms, a holding tube that accommodates the clip and locks it in a closed state, and a connection member that is detachably connected to the clip and the holding tube (for example, see Japanese Patent (Granted) Publication No. 6284009, hereinafter referred to as Patent Document 1). The connection member has a breaking portion that breaks or deforms when a predetermined amount of breaking force is applied, and the clip separates from the connection member by breaking/deforming the breaking portion.

In addition, the clip unit (clip assembly) of Japanese Patent (Granted) Publication No. 6865270, hereinafter referred to as Patent Document 2, does not include a holding tube that accommodates and locks the clip, and a lock structure is provided in a portion of the clip arm.

The present disclosure provides a clip unit, a clip delivery device, and a clip release method capable of securely locking a tissue while grasping it without obstructing a suturing work position.

SUMMARY

A clip unit according to a first aspect of the present disclosure includes a first arm including a first rotation portion, the first arm rotating around the first rotation portion as a center of rotation; and a second arm including a second rotation portion connected to the first rotation portion, the second arm rotating around the second rotation portion as a center of rotation, wherein the first rotation portion and the second rotation portion are configured to lock a relative rotation of the first arm and the second arm.

According to the clip unit, clip delivery device, and clip release method of the present disclosure, it is possible to securely lock the tissue while grasping it without obstructing the suturing operation position.

BRIEF DESCRIPTION OF THE DRAWINGS

FIG. 14 is a diagram showing an extracting step for the clip-introducing device.

FIG. 43 is an enlarged plan view of a distal end side of a clip-introducing device of a clip delivery device according to a fifth embodiment.

FIG. 46 is a diagram showing an arm closing step for the clip unit.

EMBODIMENTS

First Embodiment

A first embodiment of the present disclosure will be described with reference to FIGS. 1 to 19.

The endoscopic treatment instrument system according to the first embodiment of the present disclosure uses a clip delivery device 300, a cartridge 7, and an endoscope (not shown) in combination. The clip delivery device 300 includes a clip-introducing device (applicator) 200 and a clip unit 1.

[Clip-Introducing Device 200]

Figure 1:
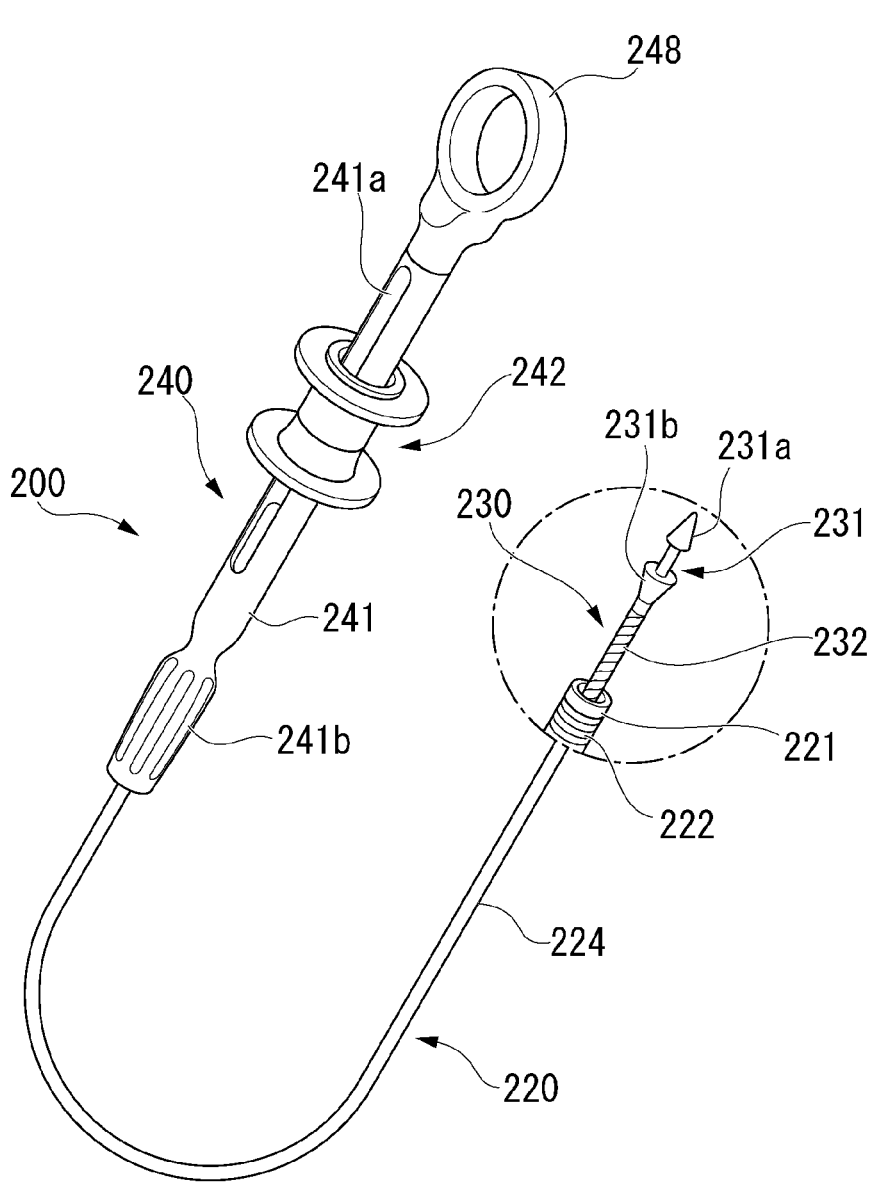
FIG. 1 is a view showing a clip-introducing device of a clip delivery device according to a first embodiment.

FIG. 1 is a diagram showing the clip-introducing device 200.

The clip-introducing device (applicator) 200 includes a sheath 220, an operation wire 230, and an operation portion 240. The clip-introducing device 200 is inserted through, for example, a treatment instrument insertion channel of an endoscope and used in combination with the endoscope. Therefore, the sheath 220 is formed longer than the treatment instrument insertion channel of the endoscope, and has an outer diameter that allows it to be inserted into the treatment instrument insertion channel. The sheath 220 is flexible and curves according to the curvature of the insertion portion of the endoscope.

The sheath 220 includes a distal tip (distal end) 221, a distal coil 222, and a proximal coil 224, and is formed in an elongated tubular shape as a whole. The distal coil 222 is arranged on the distal end side of the sheath 220. The distal tip 221 is arranged at the distal end of the distal coil 222. The sheath 220 is made of an insulating material such as a fluororesin such as PTFE (polytetrafluoroethylene), a resin material such as HDPE (high-density polyethylene), or stainless steel such as SUS301.

The operation wire 230 is inserted through the inner space S1 (see FIG. 15) of the sheath 220. In addition, the sheath 220 can fix an arm 3 of the clip unit 1 (see FIG. 3) drawn from the distal tip 221 into the internal space S1 in a closed state.

The operation wire (power transmission member) 230 includes an arrowhead hook portion (hook portion) 231 connected to the clip unit 1 and a wire 232 that operates the arrowhead hook portion 231 as shown in FIG. 1.

The arrowhead hook portion (hook portion) 231 includes a substantially conical engaging portion 231*a* that engages with the clip unit 1, and a wire-connecting portion 231*b* provided at the proximal end of the engaging portion 231*a*. The arrowhead hook portion 231 is made of, for example, a metal material such as stainless steel.

The wire 232 is inserted through the sheath 220 so that it can move back and forth. The distal end of the wire 232 is fixed to the proximal end of the wire-connecting portion 231*b* by welding, for example.

The operation portion 240 includes an operation portion main body 241, a slider 242, and a thumb ring 248, as shown in FIG. 1. The operation portion main body 241 is injection-molded, for example, from a resin material. The operation portion main body 241 includes a slit portion 241*a* and a rotation grip 241*b* on the distal end side. The slit portion 241*a* supports the slider 242 so as to be able to advance and retract. The rotation grip 241*b* allows the operator to rotate the entire clip-introducing device 200 in the central axis direction. When the entire clip-introducing device 200 rotates, the clip unit 1 connected to the arrowhead hook portion 231 of the operation wire 230 rotates in the same direction.

The slider 242 is attached to the operation portion main body 241 so as to be able to advance and retract in the longitudinal axis direction. A proximal end of the wire 232 is attached to the slider 242. As the slider 242 advances and retracts along the operation portion main body 241, the wire 232 advances and retracts with respect to the sheath 220, and the arrowhead hook portion 231 advances and retracts.

The thumb ring 248 is attached to the proximal end of the operation portion main body 241 so as to be rotatable around the longitudinal axis of the operation portion main body 241.

[Clip Unit 1]

Figure 2:
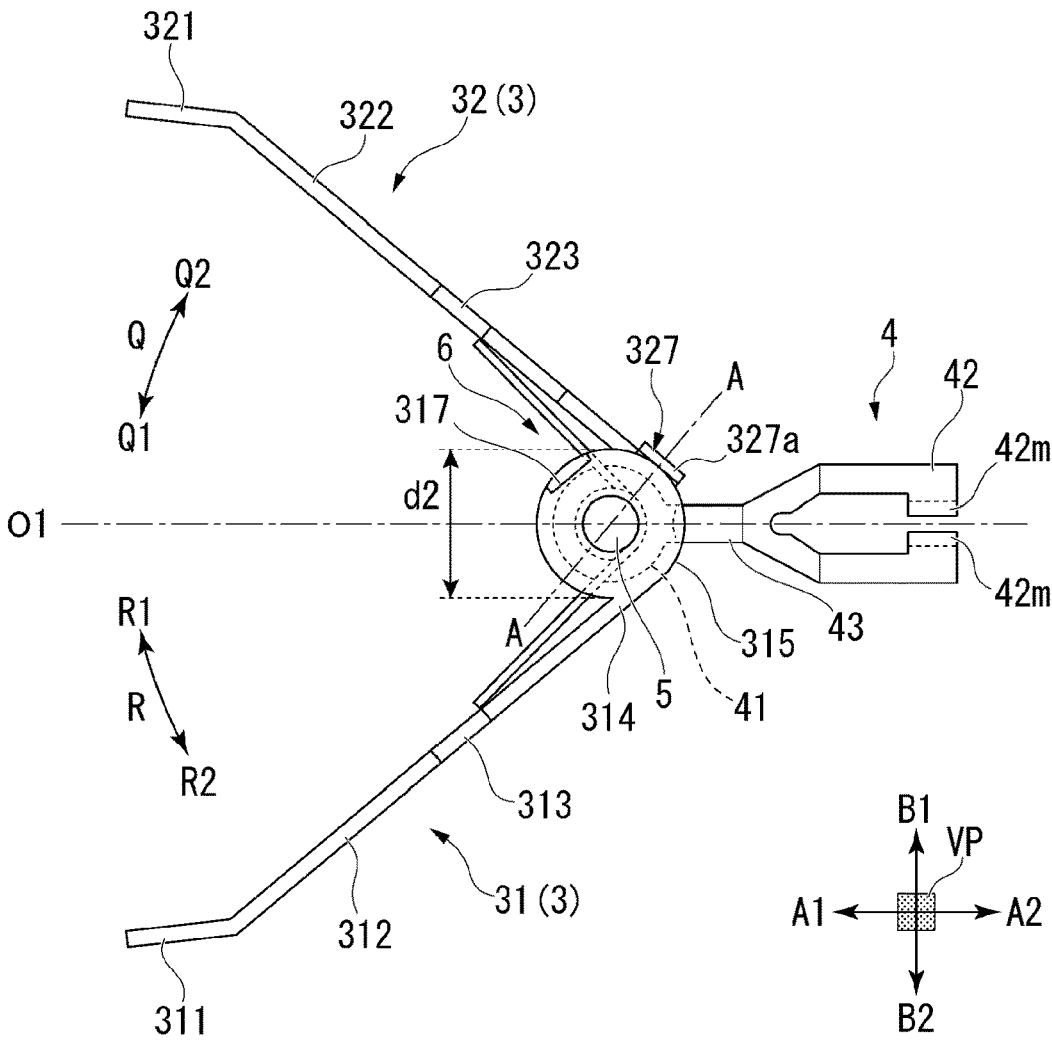
FIG. 2 is a side view showing an open state of an arm provided in a clip unit of the clip delivery device.
Figure 3:
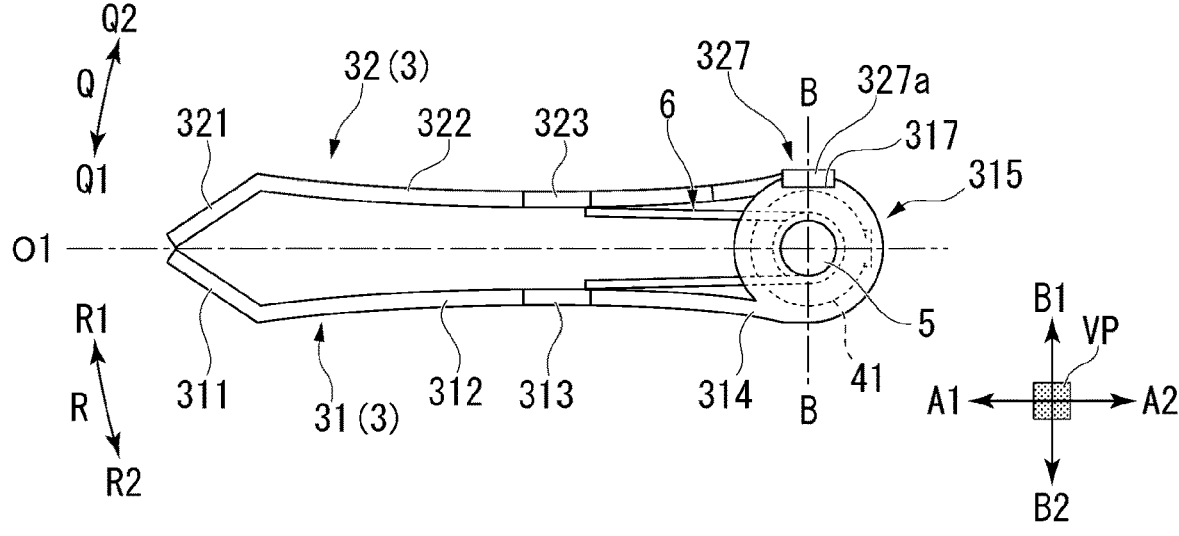
FIG. 3 is a side view showing a closed state of the arm provided in the clip unit of the clip delivery device.
Figure 4:
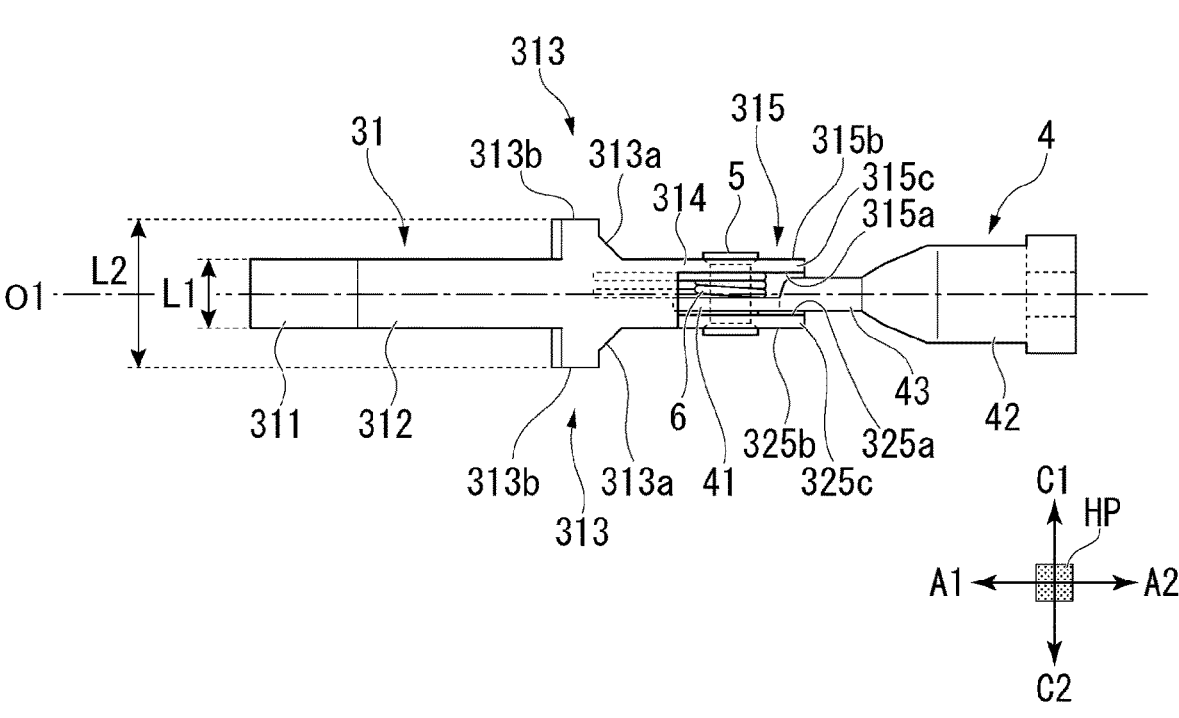
FIG. 4 is a plan view of the clip unit of the clip delivery device.
Figure 5:
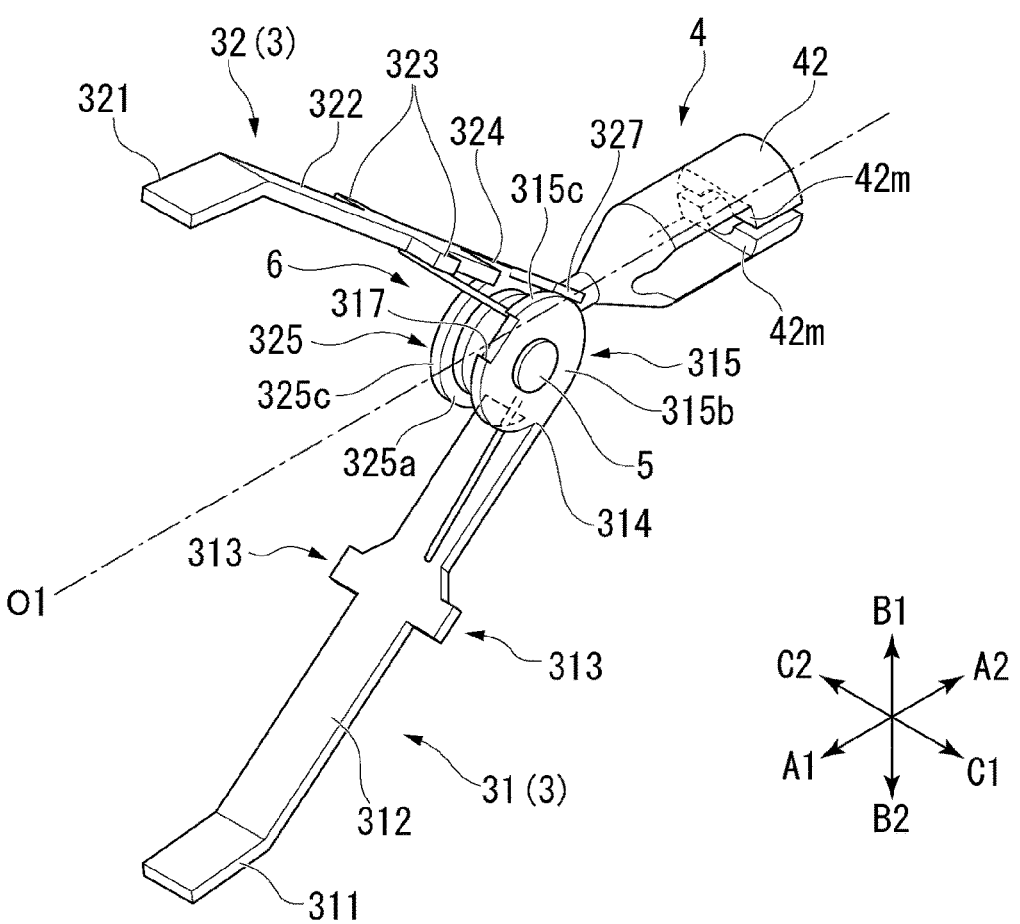
FIG. 5 is a perspective view of the clip unit of the clip delivery device.
Figure 6:
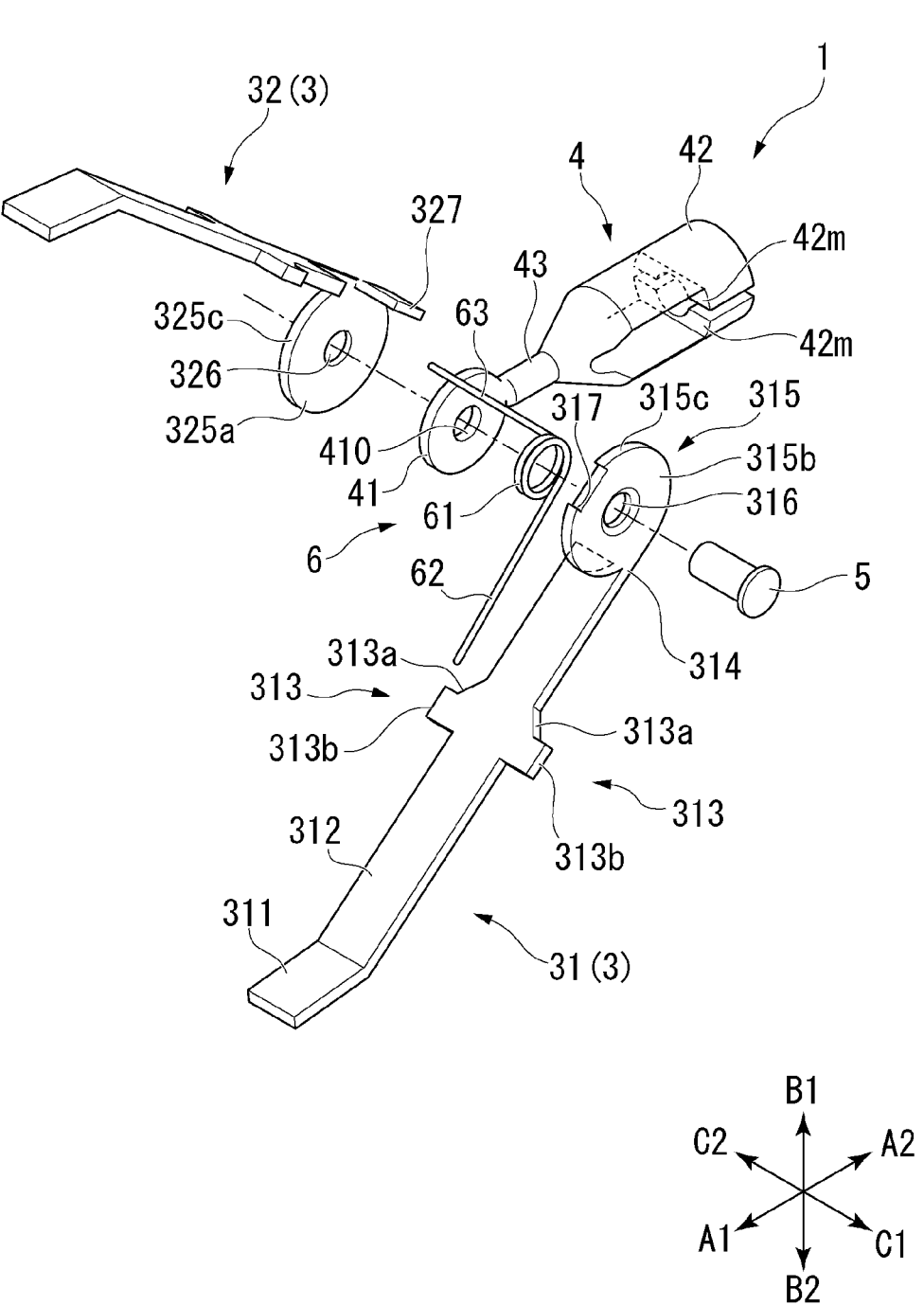
FIG. 6 is a perspective view showing a configuration of each clip unit of the clip delivery device.

FIG. 2 is a side view showing the open state of the arm 3 provided on the clip unit 1. FIG. 3 is a side view showing a closed state of the arm 3 provided on the clip unit 1. FIG. 4 is a plan view of the clip unit 1. FIG. 5 is a perspective view of the clip unit 1. FIG. 6 is a perspective view showing each configuration of the clip unit 1. The clip unit (endoscopic treatment instrument) 1 is used by being loaded (connected) to the clip-introducing device 200. The clip unit 1 is useful for patient therapeutic procedures such as preventing bleeding of body tissue, closing perforations and hemostasis, suturing contractions of internal wounds, marking lesions and tractions, and other surgical procedures.

The clip unit 1 includes the arm 3, a connection member 4, a rotation pin (connecting pin) 5, and a biasing member (biasing portion) 6, as shown in FIG. 2. In the following description, the arm 3 side in the longitudinal direction A of the clip unit 1 is referred to as the distal end side (distal end side) A1 of the clip unit 1, and the connection member 4 side is referred to as the proximal end side (proximal end side) A2 of the clip unit 1.

[Arm 3]

The arm 3 is made of resin, metal plate material, or the like. The arm 3 has a first arm 31 and a second arm 32, as shown in FIGS. 2 to 6. The first arm 31 and the second arm 32 are arranged along the vertical direction B perpendicular to the longitudinal direction A. Moreover, the first arm 31 and the second arm 32 are arranged symmetrically with respect to the central axis O1 in the longitudinal direction A of the clip unit 1 in this embodiment. The second arm 32 is arranged on the upper side B1 in the vertical direction B than the first arm 31 across the central axis O1. The first arm 31 is arranged on the lower side B2 in the vertical direction B than the second arm 32 across the central axis O1. Note that the arm 3 may have three or more arms.

The first arm 31 and the second arm 32 of the arm 3 open and close toward the distal end side A1. The arm 3 is biased by the biasing member 6, and is in an open state when a tissue-grasping portion (distal end portion) 311 of the first arm 31 and a tissue-grasping portion (distal end portion) 321 of the second arm 32 are separated from each other (hereinafter referred to as an open state). Further, the arm 3 enters a closed state when the tissue-grasping portion 311 of the first arm 31 and the tissue-grasping portion 321 of the second arm 32 approach each other from the open state (hereinafter referred to as a closed state).

[First Arm 31]

The first arm 31 is an arm provided on the lower side B2 of the arms 3. As shown in FIGS. 2 and 3, the first arm 31 has a tissue-grasping portion (distal end portion) 311, a first grasping portion 312, and a first rotation portion 315 extending from the distal end side A1 to the proximal end side A2. The first arm 31 can open and close (rotate) the distal end side A1 in an opening/closing direction (rotational direction) R with the first rotation portion 315 as the center of rotation. In the opening/closing direction R, the side of the first arm 31 facing the second arm 32 disposed on the upper side B1 in the vertical direction B across the central axis O1 is defined as the closed side R1, and the side opposite the closed side R1 away from the second arm 32 is defined as the open side R2. Note that the closed side R1 is also referred to as the inner side R1. Also, the open side R2 is also referred to as the outer side R2.

The tissue-grasping portion 311 is the distal end portion of the first arm 31 provided on the distal end side A1 in the longitudinal direction A of the first arm 31. The tissue-grasping portion 311 is formed by bending the tip of the first arm 31 toward the inner side R1. The tissue-grasping portion 311 may have a claw-shaped tip. When the arm 3 is in the closed state, the tissue-grasping portion 311 grasps the tissue by biting together with the tissue-grasping portion 321 of the second arm 32.

The first grasping portion 312 is a substantially flat plate member formed along a horizontal plane HP (see FIG. 4) defined by a longitudinal direction A and a width direction C orthogonal to the longitudinal direction A and the vertical direction B. As shown in FIG. 3, the first grasping portion 312 is arranged so that the front surface faces the closed side R1 and the back surface faces the open side R2. The surface of the first grasping portion 312 is an inner surface that contacts the living tissue in the opening/closing direction R and faces the second arm 32. When the arm 3 is pulled into the internal space S1 of the sheath 220 by the connection member 4, the first grasping portion 312 slides the rear surface thereof against the peripheral edge 221a (see FIG. 16) on the inner diameter side of the distal tip 221. Further, when the arm 3 is further pulled into the sheath 220, the first grasping portion 312 is elastically deformed. In addition, the first grasping portion 312 may be formed in a substantially cup-like shape with the back surface as the bottom surface in the closed state. The width L1 (see FIG. 4) of the first grasping portion 312 in the width direction C is slightly less than the inner diameter d1 (see FIG. 15) of the distal tip 221 of the sheath 220. The first grasping portion 312 has an engaging hook portion 313 at its central portion and a connecting portion 314 at its proximal end portion.

The engaging hook portion 313 is a convex portion that protrudes from the first grasping portion 312 in the width direction C perpendicular to the longitudinal axis direction of the first arm 31. The engaging hook portion 313 has elasticity. One side in the width direction C is the front side C1, and the other side is the back side C2. The engaging hook portion 313 protrudes by approximately the same length on both sides of the front side C1 and the back side C2 in the width direction C. The engaging hook portion 313 has a tapered portion 313a on the proximal end side A2 and a stopper portion 313b on the distal end side A1.

As shown in FIG. 4, the tapered portion 313a is an inclined portion that inclines from the distal end side A1 toward the proximal end side A2 toward the central axis O1. The tapered portion 313a abuts against the peripheral edge 221a on the inner diameter side of the distal tip 221 when the clip is released, and slides along the peripheral edge 221a when the arm 3 is drawn into the internal space S1 of the sheath 220.

Also, as shown in FIG. 4, the stopper portion 313b is a locking portion provided on the distal end side A1 of the tapered portion 313a. The width L2 (see FIG. 4) from the end on the front side C1 of the engaging hook portion 313 to the end on the back side C2 is the longest at the stopper portion 313b. The width L2 of the engaging hook portion 313 of the stopper portion 313b is longer than the width L1 of the first grasping portion 312 and longer than the inner diameter d1 of the distal tip 221 of the sheath 220. The stopper portion 313b is locked to the peripheral edge 221a on the inner diameter side of the distal tip 221 when the clip is released. Note that the tapered portion 313a is not an essential component.

The connecting portion 314 connects the first grasping portion 312 and the first rotation portion 315 as shown in FIG. 4.

The first rotation portion 315 is the proximal end portion of the first arm 31 provided on the proximal end side A2 in the longitudinal direction A of the first arm 31. The first rotation portion 315 is provided closer to the proximal end side A2 than the first grasping portion 312 that grasps the tissue. The first rotation portion 315 is a substantially disk-shaped plate member formed along a vertical plane VP (see FIG. 2) formed by the longitudinal direction A and the vertical direction B. The diameter d2 (see FIG. 15) of the first rotation portion 315 is less than the inner diameter d1 of the sheath 220. As shown in FIG. 5 or 6, the first rotation portion 315 includes a first rotation inner surface (first inner surface) 315a formed on the inner surface facing a second rotation portion 325 and facing the central axis O1, a first rotation outer surface 315b formed on the outer surface facing the opposite side of the central axis O1, and a first rotation side surface 315c on the side surface. The first rotation portion 315 is connected to the connecting portion 314 at one end of the first rotation side surface 315c and is connected to the first grasping portion 312 via the connecting portion 314. The first rotation portion 315 includes a first through-hole 316 and a notch portion (recessed portion, engaged portion) 317.

The first through-hole 316 is provided at the center of the first rotation portion 315, as shown in FIG. 6. The first through-hole 316 is a hole penetrating the first rotation portion 315 in the width direction C.

The notch portion (recessed portion, engaged portion) 317 is provided on the first rotation side surface 315c, and has a slightly larger width in the circumferential direction of the first rotation portion 315 than a protruding portion 327 described later, and is a portion cut out in a substantially rectangular shape toward the center of the first rotation portion 315. Note that, in the present embodiment, the notch portion 317 is provided at a different end portion from the end portion connected to the coupling portion 314 on the first rotation side surface 315c, and the notch portion does not reach the first through-hole 316. The notch portion 317 is part of the locking structure of the arm 3.

[Second Arm 32]

The second arm 32 is an arm provided on the upper side B1 of the arms 3. As shown in FIGS. 2 to 6, the second arm 32 includes a tissue-grasping portion (distal end portion) 321, a grasping portion 322, and a second rotation portion 325 from the distal end side A1 to the proximal end side A2. The second arm 32 can open and close (rotate) the distal end side A1 in an opening/closing direction (rotational direction) Q with the second rotation portion 325 as the center of rotation. In the opening/closing direction Q, the side where the second arm 32 faces the first arm 31 disposed on the lower side B2 in the vertical direction B across the central axis O1 is defined as the closed side Q1, and the side opposite the closed side Q1 away from the first arm 31 is defined as the open side Q2. Note that the closed side Q1 is also referred to as the inner side Q1. The open side Q2 is also called the outer side Q2.

The tissue-grasping portion 321 is the distal end of the second arm 32 provided on the distal end side A1 in the longitudinal direction A of the second arm 32. The tissue-grasping portion 321 is formed by bending the distal end of the second arm 32 toward the inner side Q1. The tissue-grasping portion 321 may have a claw-shaped tip. When the arm 3 is in the closed state, the tissue-grasping portion 321 grasps the tissue so as to bite into it together with the tissue-grasping portion 311 of the first arm 31.

The second grasping portion 322 is a substantially flat plate member formed along the horizontal plane HP formed by the longitudinal direction A and the width direction C. As shown in FIG. 3, the second grasping portion 322 is arranged so that the front surface faces the closed side Q1 and the back surface faces the open side Q2 in the closed state. The surface of the second grasping portion 322 is an inner surface that contacts the living tissue in the opening/closing direction Q and faces the first arm 31. The second grasping portion 322 slides the rear surface thereof against the peripheral edge 221a (see FIG. 16) on the inner diameter side of the distal tip 221 when the arm 3 is pulled into the internal space S1 of the sheath 220 by the connection member 4. Further, the second grasping portion 322 is elastically deformed when the arm 3 is further pulled into the sheath 220. In addition, the second grasping portion 322 may be formed in a substantially cup shape with the back surface as the bottom surface in the closed state. The width of the second grasping portion 322 in the width direction C is substantially the same as the width L1 of the first grasping portion 312 in this embodiment. The second grasping portion 322 has an engaging hook portion 323 at its center and a connecting portion 324 at its proximal end portion.

The engaging hook portion 323 is a convex portion that protrudes from the second grasping portion 322 in the width direction C perpendicular to the longitudinal axis direction of the second arm 32, as shown in FIG. 5. The engaging hook portion 323 has the same shape as the engaging hook portion 313 of the first arm 31, and in FIG. 4, since it overlaps with the engaging hook portion 313 and cannot be seen when viewed from the back side C2 in the width direction C, the illustration is omitted. The engaging hook portion 323 has elasticity. Like the engaging hook portion 313, the engaging hook portion 323 protrudes by approximately the same length on both sides of the front side C1 and the back side C2 in the width direction C. At least one of the engaging hook portion 313 and the engaging hook portion 323 may be provided on the arm 3. The engaging hook portion 323 has a tapered portion 323a on the proximal end side A2 and a stopper portion 323b on the distal end side A1.

The tapered portion 323a is an inclined portion that inclines from the distal end side A1 toward the proximal end side A2 toward the central axis O1. The tapered portion 323a abuts on the peripheral edge 221a on the inner diameter side of the distal tip 221 when the clip is released, and slides along the peripheral edge 221a when the arm 3 is drawn into the internal space S1 of the sheath 220. Note that the tapered portion 323a is not an essential component.

Also, the stopper portion 323b is a locking portion provided on the distal end side A1 with respect to the tapered portion 323a. The width from the end on the front side C1 to the end on the back side C2 of the engaging hook portion 323 is the longest at the stopper portion 323b. The width of the engaging hook portion 323 at the stopper portion 323b is approximately the same length as the width L2 of the engaging hook portion 313. The stopper portion 323b is engaged with the peripheral edge 221a on the inner diameter side of the distal tip 221 when the clip is released.

The connecting portion 324 connects the second grasping portion 322 and the second rotation portion 325 as shown in FIG. 5.

The second rotation portion 325 is connected to the first rotation portion 315 of the first arm 31 and the distal end connecting portion 41 of the connection member 4 via a rotation pin 5, which will be described below. The second rotation portion 325 is the proximal end portion of the second arm 32 provided on the proximal end side A2 in the longitudinal direction A of the second arm 32. In addition, the second rotation portion 325 is provided on the proximal end side A2 from the second grasping portion 322 that grasps the tissue. The second rotation portion 325 is a substantially disk-shaped plate member formed along the vertical plane VP. The diameter of the second rotation portion 325 is substantially the same as the diameter d2 of the first rotation portion 315. As shown in FIG. 5 or FIG. 6, the second rotation portion 325 includes a second rotation inner surface (second inner surface) 325a formed on the inner surface facing the first rotation portion 315 and facing the central axis O1, a second rotation outer surface 325b formed on the outer surface facing the opposite side of the central axis O1, and a second rotation side surface 325c on the side surface. The second rotation portion 325 is connected to the connecting portion 324 at one end of the second rotation side surface 325c and is connected to the second grasping portion 322 via the connecting portion 324. The second rotation portion 325 includes a second through-hole 326 and the protruding portion (convex portion, engaging protrusion) 327.

The second through-hole 326 is provided at the center of the second rotation portion 325, as shown in FIG. 6. The second through-hole 326 is a hole penetrating the second rotation portion 325 in the width direction C.

The protruding portion (convex portion, engaging protrusion) 327 is provided on the second rotation side surface 325c and protrudes toward the first rotation portion 315 and has elasticity. The protruding portion 327 is formed in a substantially rectangular shape and is elastically deformable. The protruding portion 327 is arranged so that at least a tip 327a abuts against the first rotation side surface 315c of the first rotation portion 315 in an elastically deformed state and biases the first rotation side surface 315c. Further, the protruding portion 327 is slidable with respect to the first rotation side surface 315c while biasing the first rotation side surface 315c. Note that, in the present embodiment, the protruding portion 327 is provided at a different end portion from the one end portion connected to the connecting portion 324 on the second rotation side surface 325c. The protruding portion 327 is part of the locking structure of arm 3.

Figure 7:
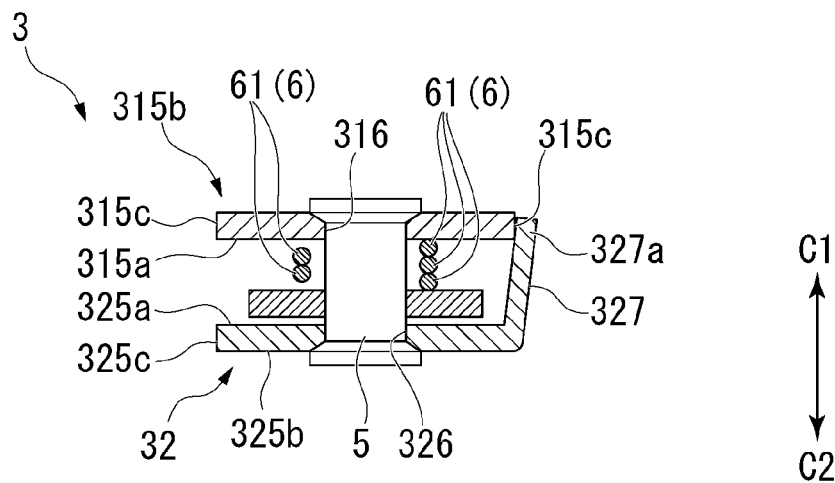
FIG. 7 is a cross-sectional view taken along line A-A shown in FIG. 2 when the arm of the clip unit is in the open state.
Figure 8:
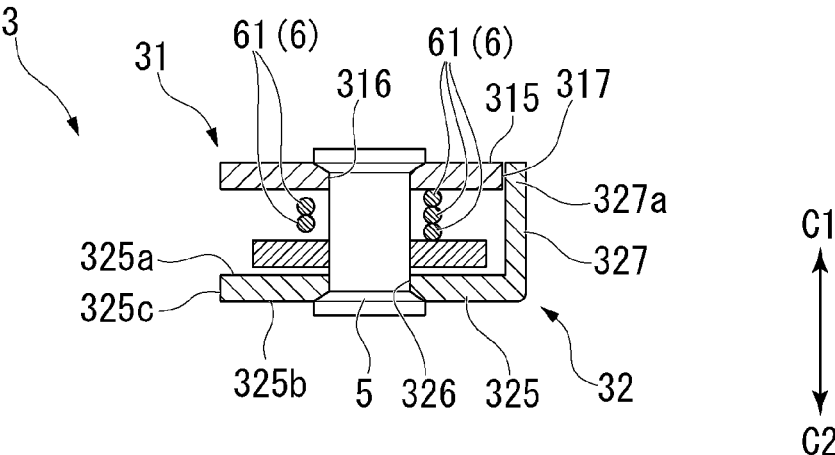
FIG. 8 is a cross-sectional view taken along line B-B shown in FIG. 3 when the arm of the clip unit is in the closed state.

The lock structure between the notch portion 317 provided on the first arm 31 and the protruding portion 327 provided on the second arm 32 will be described. FIG. 7 is a cross-sectional view taken along line A-A when the arm 3 of the clip unit 1 shown in FIG. 2 is in the open state. FIG. 8 is a cross-sectional view taken along line B-B of the clip unit 1 shown in FIG. 3 when the arm 3 is in the closed state.

When the arm 3 is pulled into the internal space S1 of the sheath 220, the rear surface of the first grasping portion 322 of the first arm 31 and the rear surface of the second grasping portion 322 of the second arm 32 are moved to the proximal end side A2 while sliding along the peripheral edge 221a on the inner diameter side of the distal tip 221. The first arm 31 rotates to the closing side R1 in the opening/closing direction R with the first rotation portion 315 as the center of rotation. Also, the second arm 32 rotates in the closing direction Q in the opening/closing direction Q with the second rotation portion 325 as the center of rotation. The protruding portion 327 of the second arm 32 contacts the first rotation side surface 315c of the first rotation portion 315 in the open state, as shown in FIGS. 2, 5 and 7. When the arm 3 is pulled into the internal space S1 of the sheath 220 from the open state, and the first arm 31 and the second arm 32 rotate toward the closing side (closing direction) of the respective opening/closing directions, the protruding portion 327 slides on the first rotation side surface 315c of the one rotation portion 315.

When the arm 3 is further pulled into the sheath 220, the engaging hook portion 313 of the first arm 31 and the engaging hook portion 323 of the second arm 32 come into contact with the peripheral edge 221a on the inner diameter side of the distal tip 221. The engaging hook portion 313 and the engaging hook portion 323 have tapered portions 313a and 323a that slide along the peripheral edge 221a, and the arm 3 slides the tapered portion 313a and the tapered portion 323a along the peripheral edge 221a on the inner diameter side of the distal tip 221. Then, when the tapered portion 313a and the tapered portion 323a slide, the first grasping portion 312 and the second grasping portion 322 are elastically deformed, and the protruding portion 327 engages with the notch portion 317 as shown in FIGS. 3 and 8. Then, the rotation of the first arm 31 and the second arm 32 is relatively locked (restricted). When the arm 3 is further pulled into the sheath 220, the stopper portion 313b of the engaging hook portion 313 and the stopper portion 323b of the engaging hook portion 323 are locked to the peripheral edge 221a on the inner diameter side of the distal tip 221.

Note that the notch portion 317 and the protruding portion 327 are not limited to the above embodiment. For example, the notch portion 317 need not be provided on the first arm 31, but may be provided on the second rotation portion 325 of the second arm 32. In this case, the protruding portion 327 need not be provided on the second arm 32, but may be provided on the first rotation portion 315 of the first arm 31.

Also, the tapered portion 313a of the engaging hook portion 313 and the tapered portion 323a of the engaging hook portion 323 are not essential components. For example, the protruding portion 327 is engaged with the notch portion 317 when the stopper portion 313b of the engaging hook portion 313 and the stopper portion 323b of the engaging hook portion 323 are locked to the peripheral edge 221a on the inner diameter side of the distal tip 221.

[Connection Member 4]

As shown in FIG. 6, the connection member 4 separably connects the arm 3 attached to the distal end side A1, which is one end in the longitudinal direction A, and the arrowhead hook portion 231 provided on the operation wire 230 of the clip-introducing device 200 at the proximal end side A2, which is the other end. That is, the connection member 4 connects the clip unit 1 and the clip-introducing device 200. The connection member 4 has a distal end connecting portion (first connecting portion) 41, a proximal end connecting portion (second connecting portion) 42, and a separating portion 43.

The distal end connecting portion (first connecting portion) 41 is provided on the distal end side A1 of the connection member 4. The distal end connecting portion 41 is a substantially disk-shaped plate member formed along the vertical plane VP. The size of the outer diameter of the distal end connecting portion 41 is smaller than the first rotation portion 315 of the first arm 31 and the second rotation portion 325 of the second arm 32. Specifically, as shown in FIG. 2, the distal end connecting portion 41 is set to have an outer diameter that does not overlap with the notch portion 317 provided in the first rotation side surface 315c of the first rotation portion 315 when viewed in the width direction C. The distal end connecting portion 41 is arranged between the first rotation portion 315 of the first arm 31 and the second rotation portion 325 of the second arm 32, as shown in FIG. 6. The distal end connecting portion 41 has a third through-hole 410.

The third through-hole 410 is provided at the center of the distal end connecting portion 41, as shown in FIG. 6. The third through-hole 410 is a hole penetrating the distal end connecting portion 41 in the width direction C. The distal end connecting portion 41 of the connection member 4 is connected to the first rotation portion 315 of the first arm 31 and the second rotation portion 325 of the second arm 32 by a rotation pin 5 described later.

The proximal end connecting portion (second connecting portion) 42 is provided on the proximal end side A2 of the connection member 4. The proximal end connecting portion 42 is bifurcated. The proximal end connecting portion 42 is elastically deformable and can be opened and closed. The proximal end connecting portion 42 is formed with a notch portion 42m for grasping and accommodating the engaging portion 231*a* of the arrowhead hook portion 231 of the clip-introducing device 200. The notch portion 42*m* is formed in a shape such that it closely contacts the outer peripheral surface of the engaging portion 231*a* provided in the substantially conical arrowhead hook portion 231.

The separating portion (breaking portion) 43 is a member that connects the distal connecting portion 41 on the distal end side A1 and the proximal end connecting portion 42 on the proximal end side A2. The separating portion 43 is deformed and broken by applying a predetermined amount of breaking force due to pulling. With this configuration, the separating portion 43 separates the distal connecting portion 41 and the proximal end connecting portion 42. The separating portion 43 is a portion that is more fragile than other portions of the connection member 4, and for example, is a portion that has a small cross-sectional area due to a notch or a slit or the like and has high mechanical fragility, or a portion that has high material weakness.

[Rotation Pin (Connecting Pin) 5]

The rotation pin (connecting pin) 5 is inserted into a first through-hole 316 of the first rotation portion 315 of the first arm 31, a second through-hole 326 of the second rotation portion 325 of the second arm 32, and a third through-hole 410 of the distal end connecting portion 41 of the connection member 4. With this configuration, the rotation pin 5 connects the first arm 31, the second arm 32, and the connection member 4. Specifically, the first arm 31 is rotatably connected to the connection member 4 in the opening/closing direction R via the rotation pin 5. Further, the second arm 32 is rotatably connected to the connection member 4 in the opening/closing direction Q via the rotation pin 5.

[Forcing Member (Biasing Portion) 6]

The biasing member (biasing portion) 6 biases the first arm 31 toward the opening side R2. Also, the biasing member 6 biases the second arm 32 toward the open side Q2. That is, the biasing member 6 biases the first arm 31 and the second arm 32 toward the opening side (opening direction) of the opening/closing direction of each of the first arm 31 and the second arm 32. The biasing member 6 is a spring member such as a torsion coil spring in this embodiment, and biases the first arm 31 and the second arm 32 at the same time. As shown in FIG. 6, the biasing member 6 includes a coil portion 61, and a first connecting portion 62 and a second connecting portion 63 each extending from the coil portion 61 toward the front end side A1 in the longitudinal direction A. The biasing member 6 is not particularly limited, and may be a torsion spring, a kick spring, a leaf spring, or the like.

As shown in FIG. 6, the coil portion 61 is provided, for example, between the distal end connecting portion 41 and the first rotation portion 315 of the first arm 31, and is attached to the outer circumference of the rotation pin 5. The first connecting portion 62 is attached to the first arm 31 by extending from the coil portion 61 along the first grasping portion 312 of the first arm 31. The second connecting portion 63 extends from the coil portion 61 along the second grasping portion 322 of the second arm 32 and is attached to the second arm 32. With this configuration, the biasing member 6 biases the first arm 31 and the second arm 32 toward the opening side (opening direction) in the opening/closing direction where the tissue-grasping portion (distal end portion) 311 of the first arm 31 and the tissue-grasping portion (distal end portion) 321 of the second arm 32 are separated from each other, so as to be in the open state. Therefore, the first arm 31 and the second arm 32 have self-expanding forces in their respective opening/closing directions. Note that the coil portion 61 may be provided between the distal end connecting portion 41 and the second rotation portion 325 of the second arm 32.

[Cartridge 7]

Figure 9:
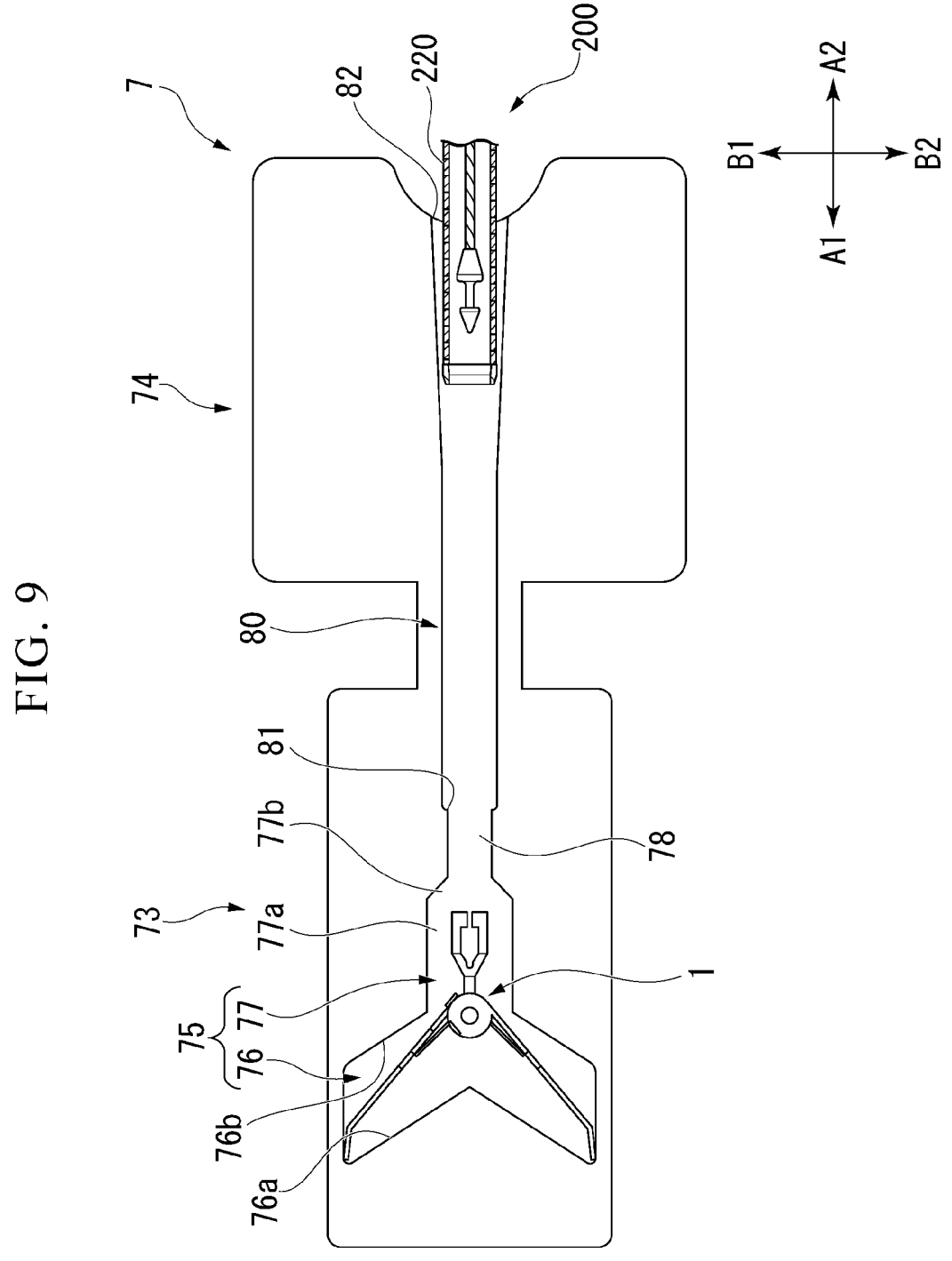
FIG. 9 is a schematic partial cross-sectional view of a cartridge for loading the clip unit into the clip-introducing device.
Figure 10:
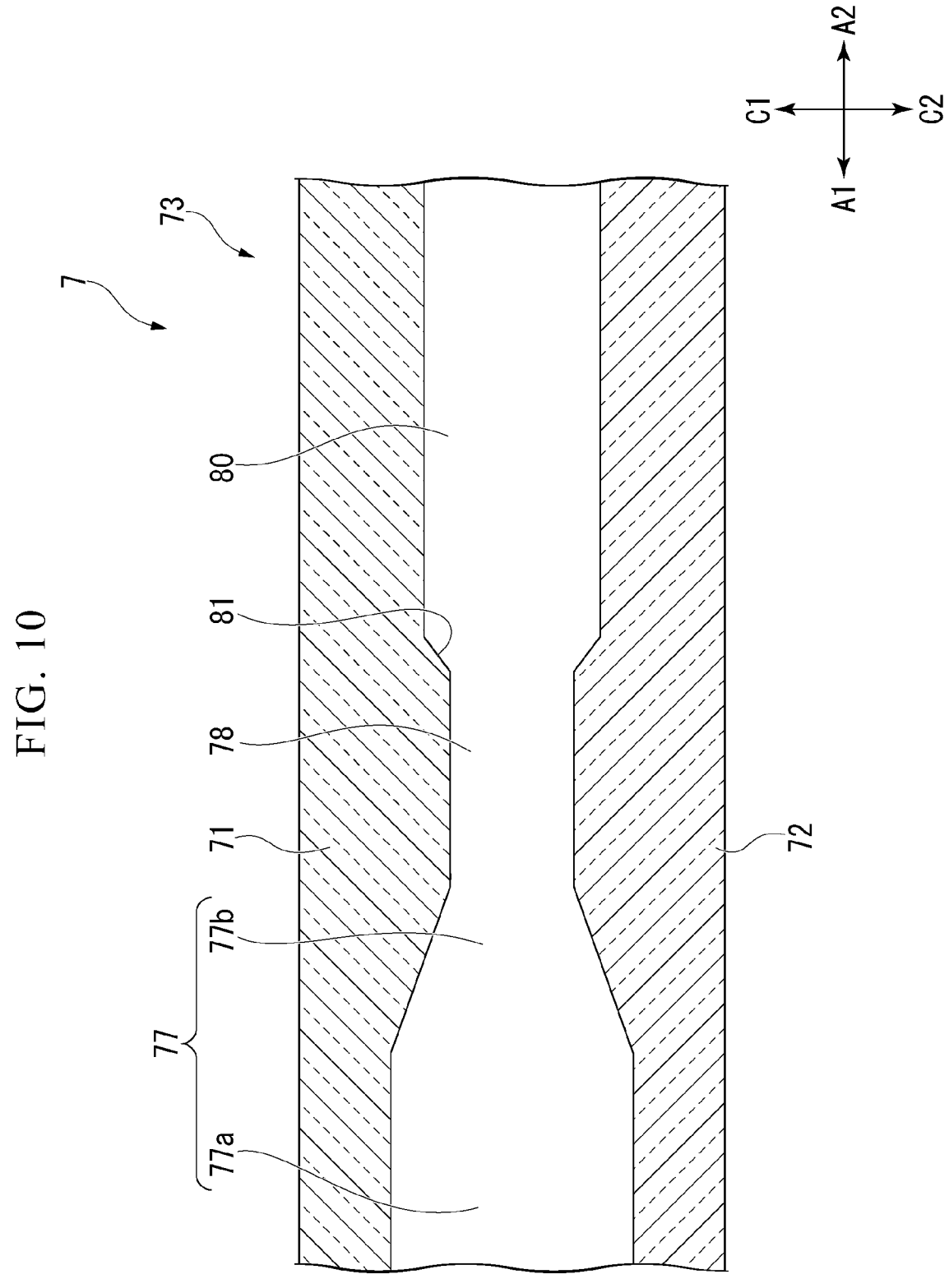
FIG. 10 is an enlarged view of part of the cartridge as seen from below.

FIG. 9 is a schematic partial cross-sectional view of the cartridge 7. FIG. 10 is an enlarged view of part of the cartridge 7 of FIG. 9 viewed from the lower side B2.

The cartridge 7 is an accommodating case for accommodating the clip unit 1, as shown in FIG. 9. Although the type of cartridge 7 is not particularly limited, the cartridge described in Japanese Patent (Granted) Publication No. 4700608 can be used in this embodiment for example.

The cartridge 7 is formed by stacking an upper case 71 and a lower case 72 in the width direction C, as shown in FIG. 10. As shown in FIG. 9, a clip unit-accommodating portion (treatment instrument-accommodating portion) 73 in which the clip unit 1 is accommodated is formed on the distal end side A1 of the cartridge 7 in the longitudinal direction A. A pressing portion 74 is formed on the proximal end side A2 of the cartridge 7 in the longitudinal direction A. Since the upper case 71 and the lower case 72 are the same shape, the lower case 72 will be representatively described in the following description of the clip unit-accommodating portion 73 and the pressing portion 74.

As shown in FIG. 9, the clip unit-accommodating portion 73 includes a clip main body-accommodating portion (treatment instrument main body-accommodating portion) 75 formed of a substantially Y-shaped concave portion. The clip body-accommodating portion 75 includes a first clip-accommodating portion 76 and a second clip-accommodating portion 77 provided on the proximal end side A2 of the first clip-accommodating portion 76. In addition, the clip unit-accommodating portion 73 includes a sheath insertion portion 80 formed across the pressing portion 74 on the proximal end side A2 of the second clip-accommodating portion 77.

The first clip-accommodating portion 76 stores the arm 3 of the clip unit 1 in an open state. The first clip-accommodating portion 76 has a tapered surface 76*a* at the distal end thereof with which the tissue-grasping portion 311 of the first arm 31 and the tissue-grasping portion 321 of the second arm 32 abut. Also, the first clip-accommodating portion 76 forms an arm contraction portion 76*b* at the proximal end portion. The arm reduction portion 76*b* is used to guide the arm 3 of the clip unit 1 in a direction to reduce the opening of the arm 3.

As shown in FIG. 9, the second clip-accommodating portion 77 includes a proximal end connecting portion enlarged diameter portion 77*a* that allows opening and closing of the proximal end connecting portion 42 of the connection member 4, and a locking spring accommodating recess portion 77*b*.

The proximal end connecting portion enlarged diameter portion 77*a* is an opening/closing permitting portion that allows the proximal end connecting portion 42 of the connection member 4 to elastically expand (open and close). The cross-sectional shape of the proximal end connecting portion enlarged diameter portion 77*a* is substantially elliptical when the upper case 71 and the lower case 72 are engaged with each other. The proximal end connecting portion enlarged diameter portion 77*a* has a space so as to open and close the proximal end connecting portion 42 of the connection member 4 in a predetermined direction when the arrowhead hook portion 231 of the clip-introducing device 200 and the connection member 4 of the clip unit 1 are engaged with each other. That is, the proximal end connecting portion enlarged diameter portion 77*a* is an engagement-permitting portion of the proximal end connecting portion 42. The proximal portion of the proximal end connecting portion 42 is allowed to expand (open and close) by means of the proximal end connecting portion enlarged diameter portion 77*a*.

The locking spring accommodating recess portion 77*b* is tapered from the proximal end side A2 toward the distal end side A1. As shown in FIG. 10, the locking spring accommodating recess portion 77*b* has a tapered surface inclined toward the center of the cartridge 7 from the distal end side A1 to the proximal end side A2 as shown in FIG. 10. When the arm 3 is slid from the distal end side A1 to the proximal end side A2, the locking spring accommodating recess portion 77*b* contracts by elastically deforming the engaging hook portion 313 and the engaging hook portion 323 of the first arm 31 and the second arm 32 toward the center of the clip unit 1.

The connection member housing portion 78 is a blocking portion that holds the proximal end connecting portion 42 in a diameter-reduced (blocking) state. In addition, the connection member housing portion 78 maintains the elastically deformed state of the engaging hook portion 313 and the engaging hook portion 323 of the first arm 31 and the second arm 32. The cross-sectional shape of the connection member housing portion 78*a* is substantially circular when the upper case 71 and the lower case 72 are engaged with each other.

The sheath insertion portion 80 is an arcuate groove formed in the longitudinal direction A on the proximal end side A2 of the connection member housing portion 78. The sheath 220 is inserted into the sheath insertion portion 80 from an inlet 82 on the proximal end side A2. The sheath insertion portion 80 may be a V-shaped groove instead of a circular arc groove. The sheath insertion portion 80 has a distal tip-abutting portion 81.

The distal tip-abutting portion 81 is formed at the distal end of the sheath insertion portion 80. The distal end surface of the distal tip 221 of the sheath 220 is abutted against the distal tip-abutting portion 81. When the distal end of the distal tip 221 of the sheath 220 is abutted against the distal tip-abutting portion 81, the inner diameter of the distal tip 221 is the same as the inner diameter of the connection member housing portion 78. Therefore, the surface of the connection member housing portion 78 and the inner peripheral surface of the distal tip 221 are smoothly connected.

The pressing portion 74 is a plate-like member provided on the proximal end side A2 of the cartridge 7, as shown in FIG. 9. The pressing portion 74 is provided on both the upper case 71 and the lower case 72 so as to face each other in the width direction C. The pressing portion 74 is, for example, about 20 mm square, and is formed in a size suitable for picking up with fingers.

Note that the clip unit 1 is arranged substantially on the central axis of the cartridge 7 when the clip unit 1 is arranged inside the cartridge 7. Thus, the cartridge 7 accommodating the clip unit 1 is blister-packaged and enclosed in a sterilization pack or the like, for example.

[Operation and Action of Clip Delivery Device 300]

The operation and action of the clip delivery device 300 will now be described with reference to FIGS. 11 to 19.

First, a method of attaching (reloading) the clip unit 1 using the cartridge 7 to the clip-introducing device 200 will be described with reference to FIGS. 11 to 14.

<Insertion Step>

Figure 11:
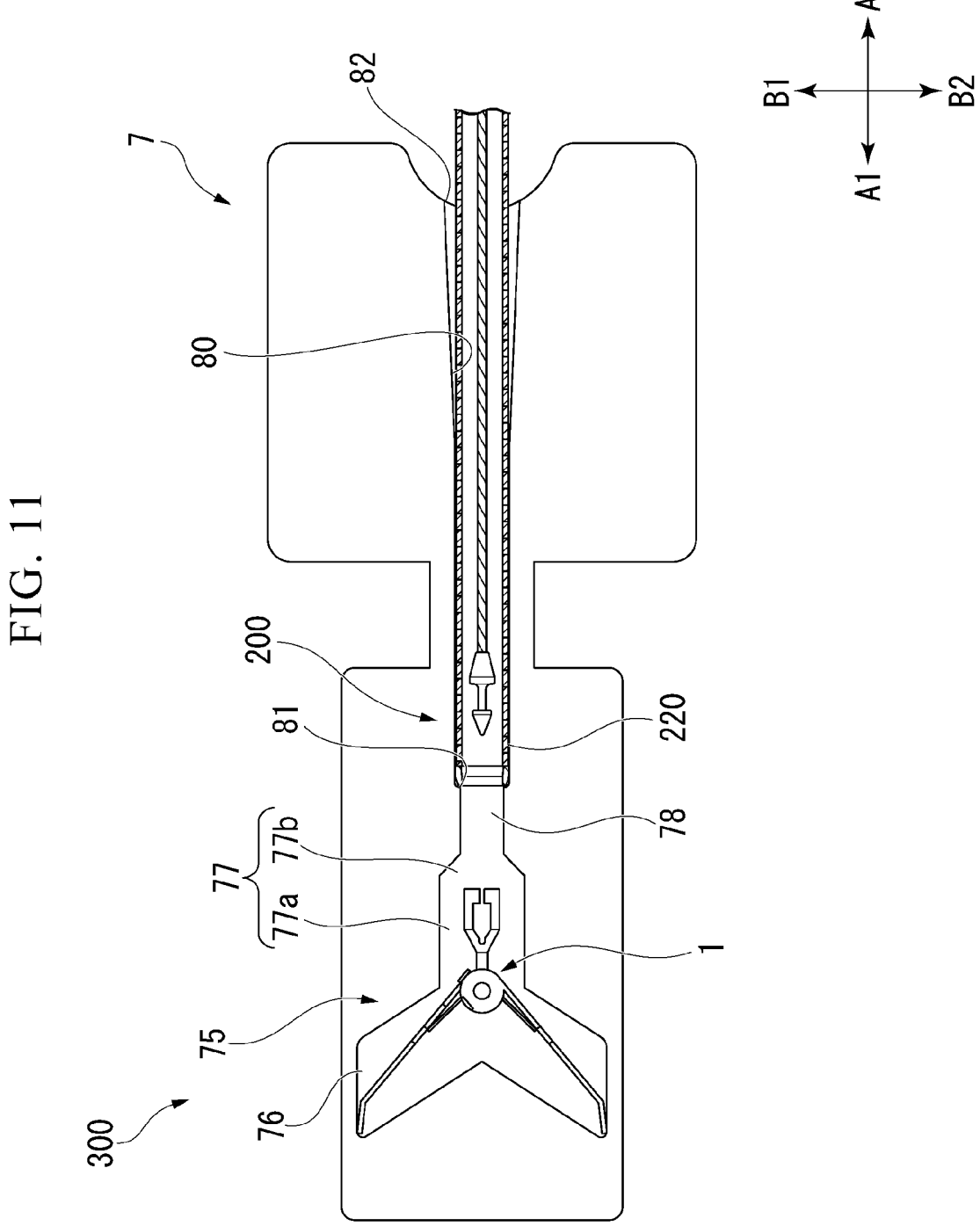
FIG. 11 is a diagram showing an insertion step for the clip-introducing device.

FIG. 11 is a diagram showing the insertion step of the clip-introducing device 200.

The operator inserts the sheath 220 of the clip-introducing device 200 into the sheath insertion portion 80 from the inlet 82 on the proximal end side A2 of the cartridge 7, as shown in FIG. 11. The distal tip 221 of the sheath 220 is abutted against the distal tip-abutting portion 81 at its distal end surface. In a state where the distal end of the distal tip 221 of the sheath 220 is abutted against the distal tip-abutting portion 81, the operator presses the sheath 220 with the pressing portion 74 to fix the sheath 220 to the cartridge 7.

<Loading Step>

Figure 12:
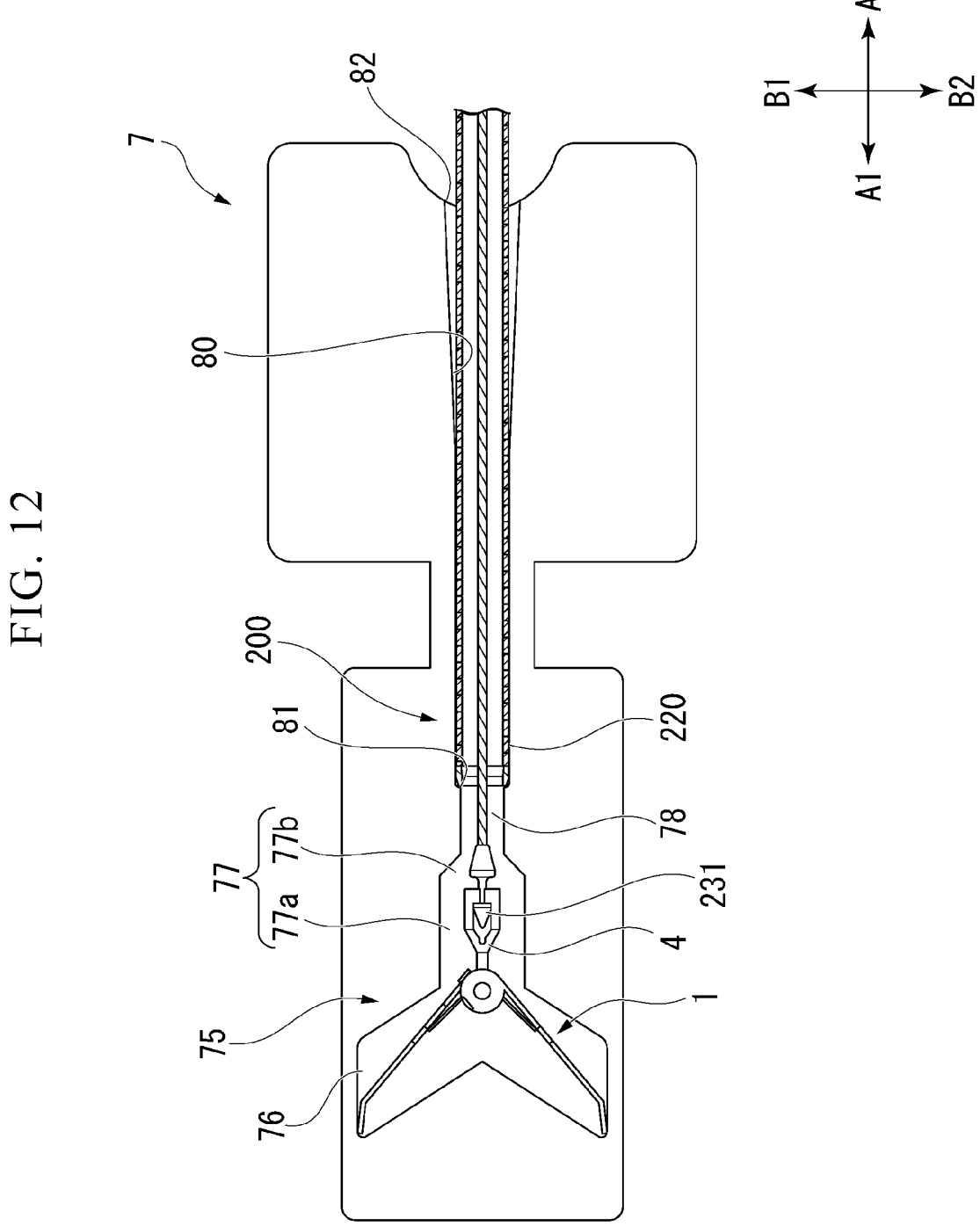
FIG. 12 is a diagram showing a loading step for the clip-introducing device.

FIG. 12 is a diagram showing the loading step of the clip-introducing device 200.

As shown in FIG. 12, the operator operates the operation portion 240 to advance the operation wire 230 with respect to the sheath 220, thereby advancing the arrowhead hook portion 231. The arrowhead hook portion 231 loads the clip unit 1 accommodated in the cartridge 7 into the clip-introducing device 200 by connecting with the connection member 4 of the clip unit 1.

<Pulling Step>

Figure 13:
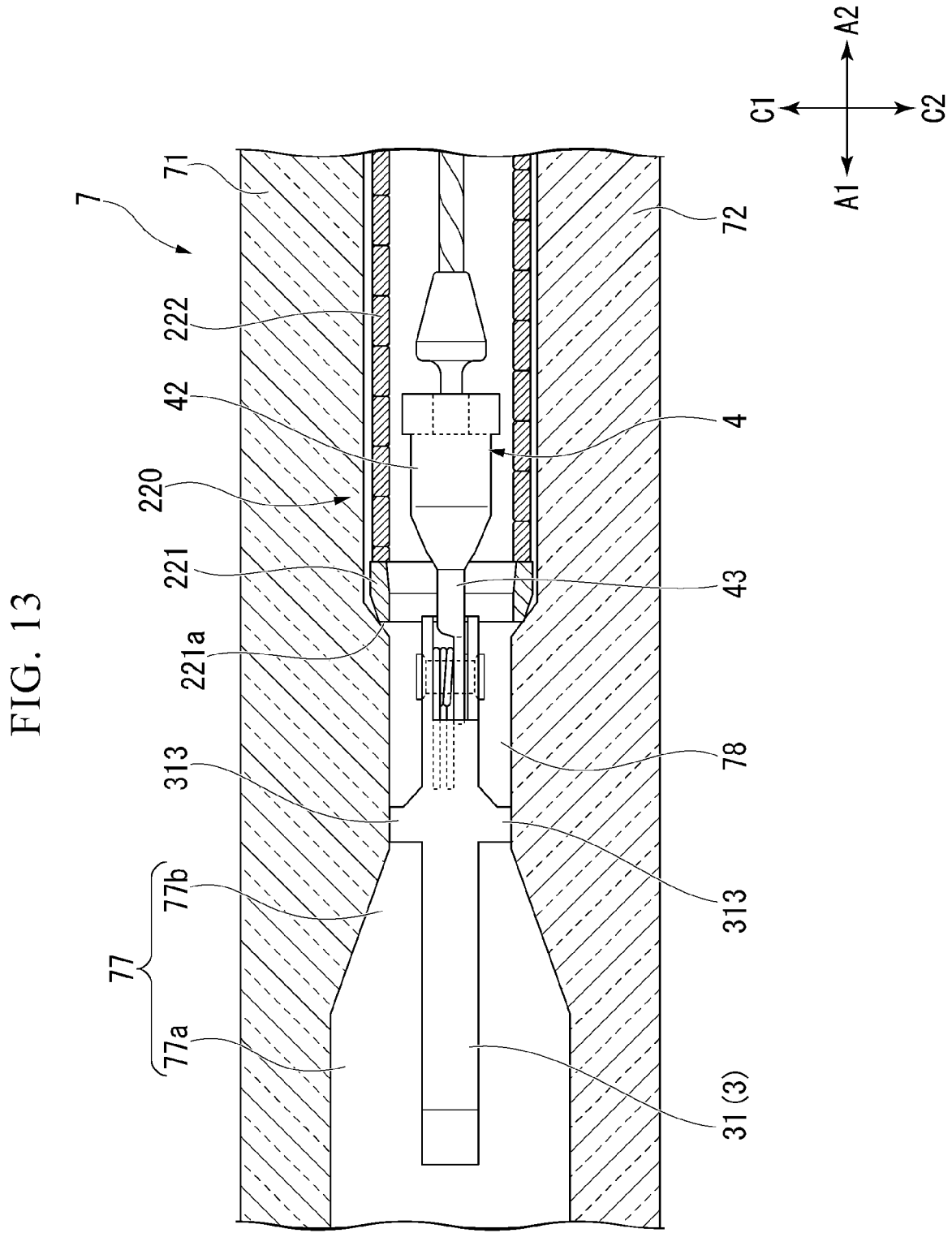
FIG. 13 is a diagram showing a pulling step for the clip-introducing device.

FIG. 13 are diagrams showing the pulling step of the clip-introducing device 200.

The operator pulls the operation wire 230 to the proximal end side A2, as shown in FIG. 13. The clip unit 1 is pulled toward the proximal end side A2 by the connection member 4 connected to the arrowhead hook portion 231. The separating portion 43 of the connection member 4 pulls the arm 3 without breaking.

<Contraction Step>

The operator further pulls the clip unit 1 to the proximal end side A2. Then, as shown in FIG. 13, when the arm 3 is slid from the distal end side A1 to the proximal end side A2, the locking spring accommodating recess portion 77*b* contracts elastically deforming the engaging hook portion 313 and the engaging hook portion 323 of the first arm 31 and the second arm 32 toward the center of the clip unit 1. When the operator pulls the clip unit 1 further toward the proximal end side A2, the proximal end connecting portion 42 is in a diameter-reduced state at the connection member housing portion 78. Also, the contracted engaging hook portion 313 and engaging hook portion 323 of the first arm 31 and the second arm 32 are kept in an elastically deformed state. Therefore, the stopper portion 313*b* and the stopper portion 323*b* provided on the distal end side A1 of the engaging hook portion 313 and the engaging hook portion 323 are not locked to the peripheral edge 221*a* on the inner diameter side of the distal tip 221. In this state, the clip unit 1 is drawn into the internal space S1 of the sheath 220 without being caught by the inner peripheral edge 221*a* of the distal tip 221 that is in contact with the distal tip-abutting portion 81 at the proximal end portion.

As shown in FIG. 13, the arm 3 of the clip unit 1 is held closed by the distal tip 221 of the sheath 220 and the distal coil 222 according to their inner diameters. The engaging hook portion 313 and the engaging hook portion 323 of the first arm 31 and the second arm 32 are kept in contact with the inner surface of the sheath 220 and accommodated in the inner space S1 of the sheath 220.

<Extracting Step>

Figure 14:
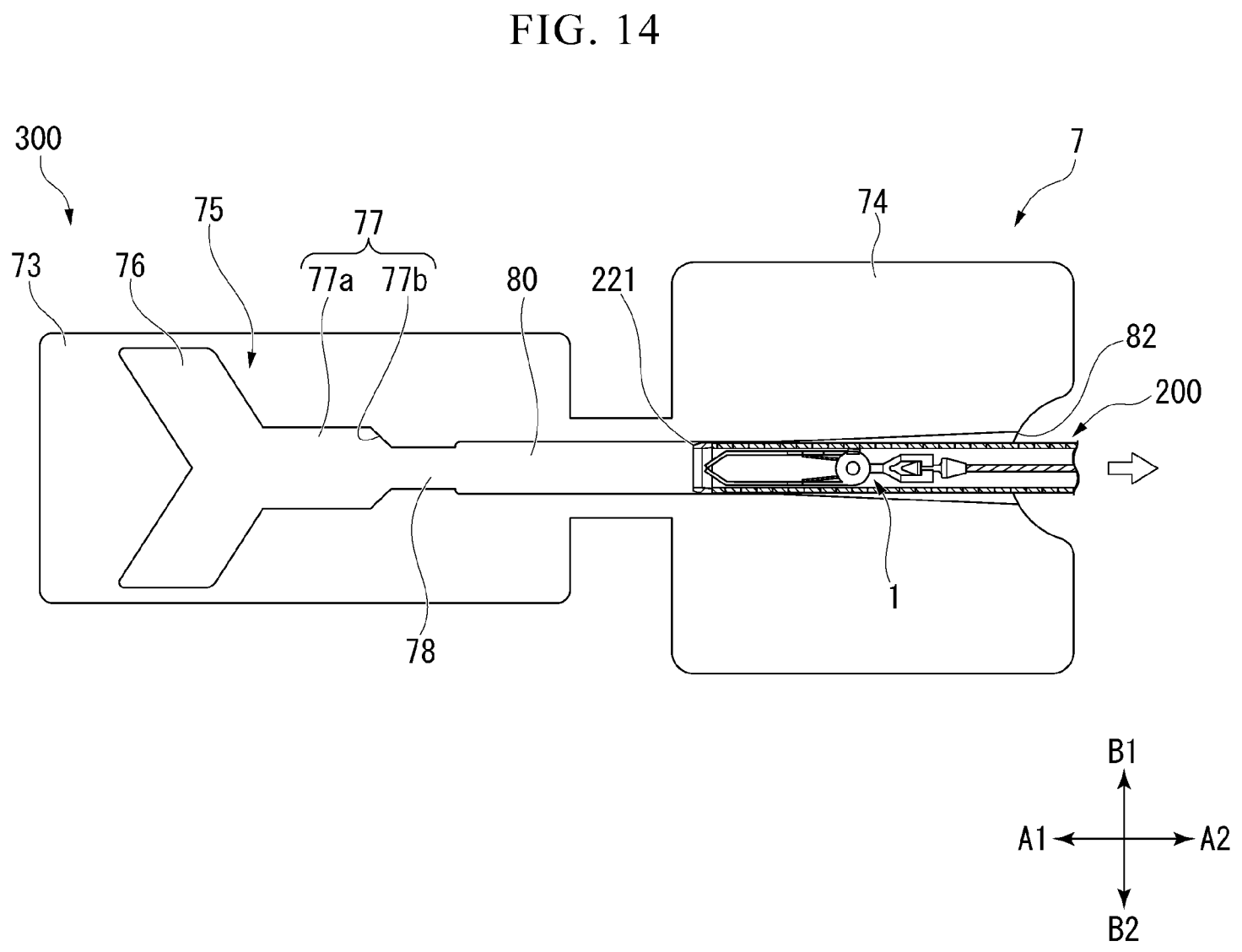

FIG. 14 is a diagram showing an extracting step for the clip-introducing device 200.

After the clip unit 1 is drawn into the internal space S1 of the sheath 220, the strength to grasp the pressing portion 74 of the cartridge 7 is weakened, and the sheath 220 can be extracted from the sheath insertion portion 80 of the cartridge 7. That is, the sheath 220 is separated from the cartridge 7. The clip unit 1 is loaded onto the arrowhead hook portion 231 of the operation wire 230 of the clip-introducing device 200.

Next, a clip release method for the clip delivery device 300 will be described with reference to FIGS. 15 to 19. In this embodiment, as an example of a method of using the clip delivery device 300, a procedure for ligating a wound in body tissue (not shown) will be described.

<Arm 3 Opening Step>

Figure 15:
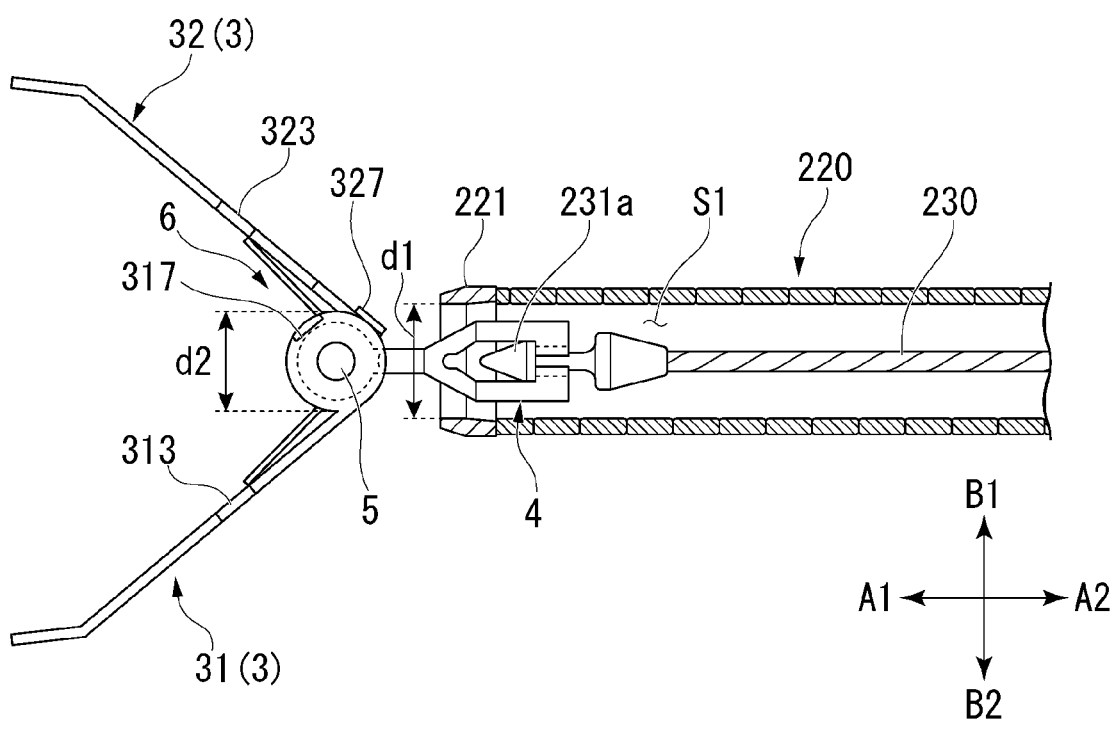
FIG. 15 is a view showing an arm-opening step of the clip unit.

FIG. 15 is a diagram showing the arm 3 opening step of the clip unit 1.

The operator introduces the clip unit 1 loaded in the clip-introducing device 200 into the body via the treatment instrument insertion channel of the endoscope. Next, the operator advances the arrowhead hook portion 231 by advancing the slider 242 along the operation portion main body 241. The operator advances the clip unit 1 until the arm 3 comes out of the sheath 220. When the arm 3 comes out of the sheath 220, it will be in an open state. As shown in FIG. 15, when the arm 3 comes out of the sheath 220, the engaging hook portion 313 and the engaging hook portion 323 of the first arm 31 and the second arm 32 return from the elastically deformed state to the non-elastically deformed state, which is the basic posture.

<Pulling Step>

Figure 16:
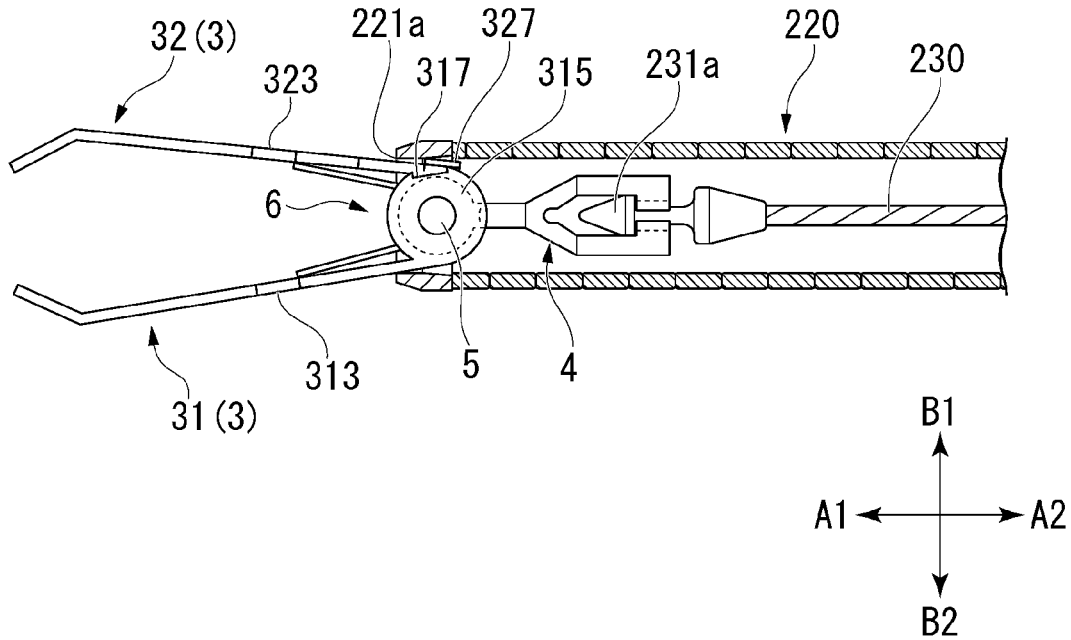
FIG. 16 is a diagram showing a pulling step of the clip unit.

FIG. 16 is a diagram showing the pulling step of the clip unit 1.

The operator places the arm 3 of the clip unit 1 at the suturing position of the wound. The operator retracts the arrowhead hook portion 231 by retracting the slider 242 along the operation portion main body 241. The connection member 4 connected to the arrowhead hook portion 231 pulls the arm 3. The arm 3 is then drawn into the internal space Sb1 of the sheath 220. The operator may rotate the clip unit 1 during the arm 3 opening step and the pulling step. The operator operates the rotation grip 241*b* of the operation portion 240 to rotate the entire unit in the direction of the central axis. Thus, the clip unit 1 connected to the arrowhead hook portion 231 of the operation wire 230 can be rotated in the same direction. Therefore, even when the tissue is in a direction that makes it difficult to grasp the tissue with respect to the clip unit 1, the operator can rotate the clip unit 1 to adjust the tissue to be easily grasped.

<Arm 3 Accommodating Step>

Figure 17:
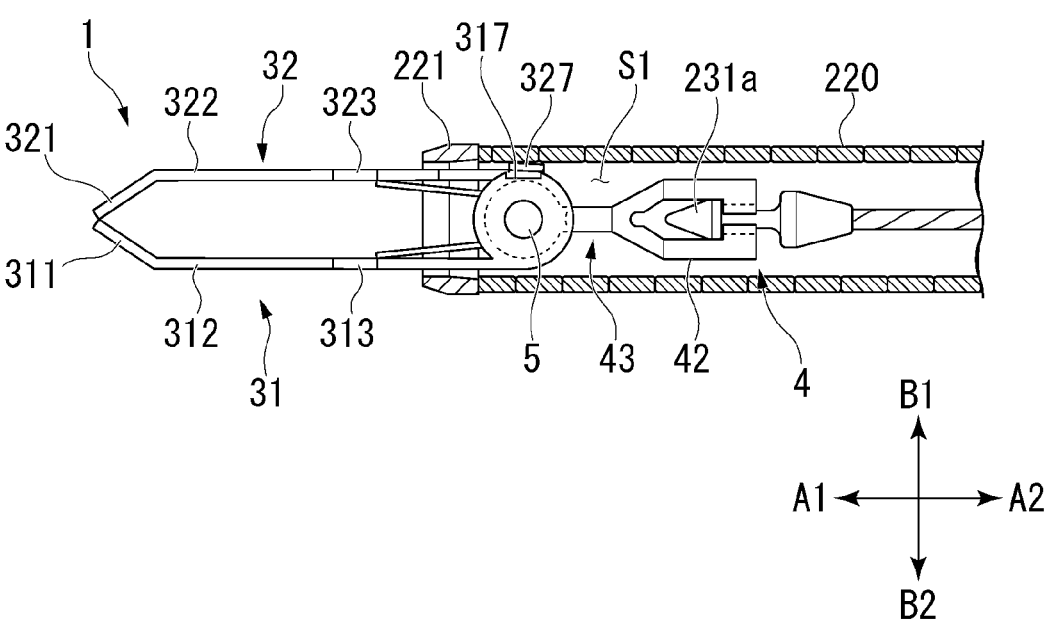
FIG. 17 is a diagram showing an arm accommodating step of the clip unit.

FIG. 17 is a diagram showing steps for accommodating the clip unit 1.

As shown in FIG. 17, when the arm 3 is drawn into the internal space S1 of the sheath 220, it moves to the proximal end side A2 while sliding the rear surface of the first grasping portion 312 of the first arm 31 and the rear surface of the second grasping portion 322 of the second arm 32 to the peripheral edge 221*a* on the inner diameter side of the distal tip 221. The first arm 31 then rotates to the closing side R1 in the opening/closing direction R with the first rotation portion 315 as the center of rotation. Also, the second arm 32 rotates in the closing direction Q1 in the opening/closing direction Q with the second rotation portion 325 as the center of rotation. The arm 3 is accommodated in the internal space S1 of the sheath 220 and is in a closed state to grasp the tissue.

<Sliding Step of Protruding Portion 327>

As shown in FIG. 15, the protruding portion 327 of the second arm 32 is in contact with the first rotation side surface 315*c* of the first rotation portion 315 in the open state. As shown in FIGS. 16 and 17, the arm 3 is pulled into the internal space S1 of the sheath 220 from the open state, and the first arm 31 and the second arm 32 move toward the closing side (closing direction) in the opening/closing direction. When rotated, the protruding portion 327 slides on the first rotation side surface 315*c* of the first rotation portion 315.

<Re-Grasping Step>

After executing the sliding step of the protruding portion 327, the operator operates the clip unit 1 again in the re-grasping step to rotate the arm 3 and shift the arm 3 to the open state. Thereby it is also possible to re-grasp the tissue.

<Deformation and Lock-Setting Step>

Figure 18:
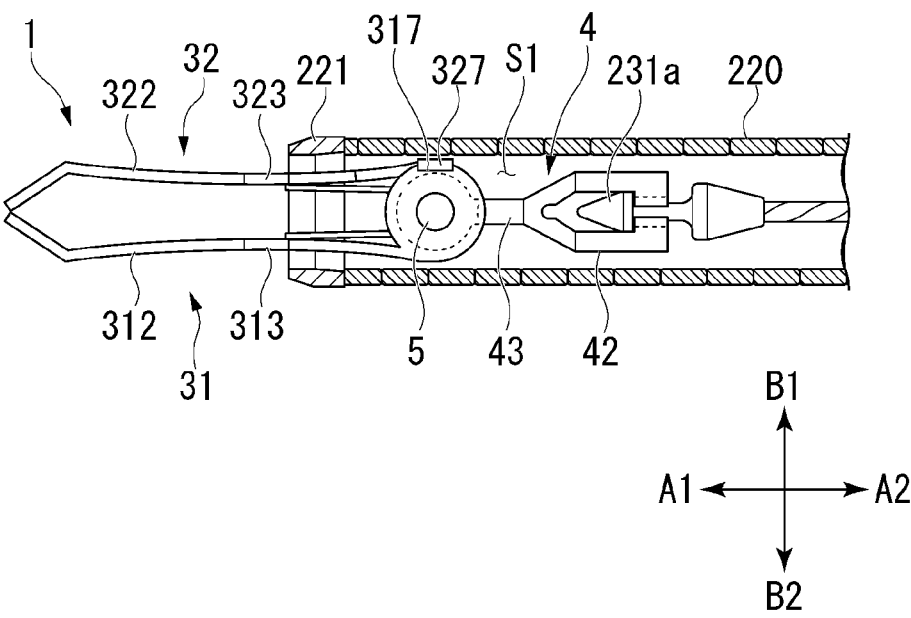
FIG. 18 is a diagram showing deformation and lock-setting steps for the clip unit.

FIG. 18 is a diagram showing deformation and lock-setting steps of the clip unit 1.

When the arm 3 is further pulled into the sheath 220, the engaging hook portion 313 of the first arm 31 and the engaging hook portion 323 of the second arm 32 come into contact with the peripheral edge 221 *a* on the inner diameter side of the distal tip 221.

The engaging hook portion 313 and the engaging hook portion 323 have tapered portions 313*a* and 323*a* that slide along the peripheral edge 221*a*. When the first grasping portion 312 and the second grasping portion 322 are elastically deformed when the tapered portion 313*a* and the tapered portion 323*a* slide along the peripheral edge 221*a*, the protruding portion 327 engages with the notch portion 317 as shown in FIG. 18. With the above configuration, the rotation of the first arm 31 and the second arm 32 is relatively locked (restricted).

<Connection Release Step>

Figure 19:
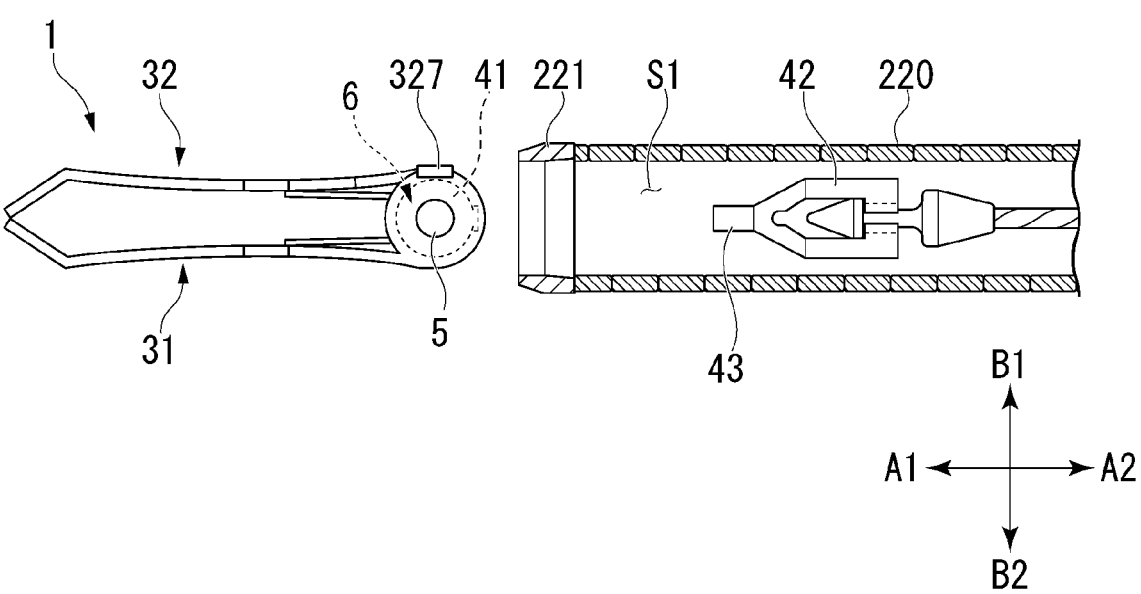
FIG. 19 is a diagram showing a connection release step for the clip unit.

FIG. 19 is a diagram showing a connection release step of the clip unit 1.

The operator further retracts the slider 242 along the operation portion main body 241 to retract the clip unit 1 loaded on the arrowhead hook portion 231. Then, when the arm 3 is further pulled into the sheath 220, while the stopper portion 313*b* of the engaging hook portion 313 and the stopper portion 323*b* of the engaging hook portion 323 are engaged with the peripheral edge 221*a* on the inner diameter side of the distal tip 221, the first grasping portion 312 and the second grasping portion 322 are further elastically deformed. Then, a predetermined amount of breaking force is applied to the separating portion (breaking portion) 43, and the separating portion 43 breaks. The operator withdraws the sheath 220 and leaves the clip unit 1 with the tissue ligated in the body.

According to the clip unit 1 and the clip release method using the clip unit 1 according to this embodiment, the closed state of the arm 3 can be securely locked while grasping the tissue.

Also, the clip unit 1 does not have a holding tube that conventional clip units have. Therefore, even if the operator uses a plurality of clip units 1, the clip units 1 do not block the sewing position, so the operator can easily see the sewing position.

In addition, the clip unit 1 is provided with a notch portion 317 and a protruding portion 327, which are locking structures, on the first rotation portion 315 and the second rotation portion 325 that do not grasp the tissue. Therefore, when the tissue is grasped by the arm 3, there is no risk of the tissue being bitten by the locking structure.

As described above, the first embodiment of the present disclosure has been described in detail with reference to the drawings, but the specific configuration is not limited to this embodiment, and design changes and the like are included within the scope of the present disclosure. Also, the constituent elements shown in the above-described embodiment and modifications can be combined as appropriate.

Second Embodiment

Next, a second embodiment of the present disclosure will be described with reference to FIGS. 20 to 25. In the following description, the same reference numerals are given to the same configurations as those already described, and redundant descriptions will be omitted. Note that, in the following embodiments, the notch portion and the protruding portion, which are lock structures, provided in the first rotation portion and the second rotation portion of the clip unit and the distal end connecting portion (first connecting portion) of the connection member are different from the first embodiment. Therefore, in the following description, the differences from the first embodiment will be mainly described.

Figure 20:
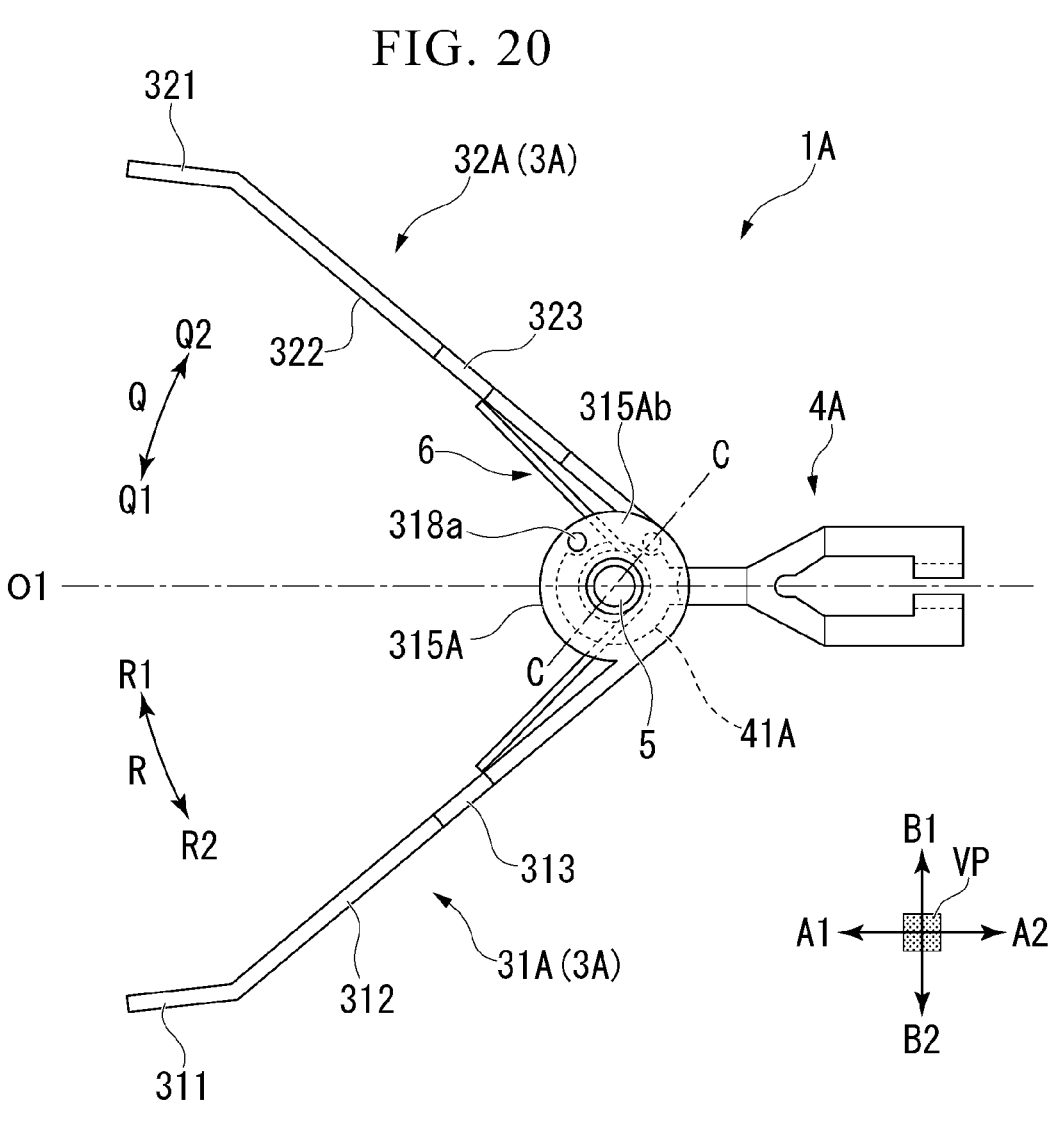
FIG. 20 is a side view showing an open state of an arm provided in a clip unit of a clip delivery device according to a second embodiment.
Figure 21:
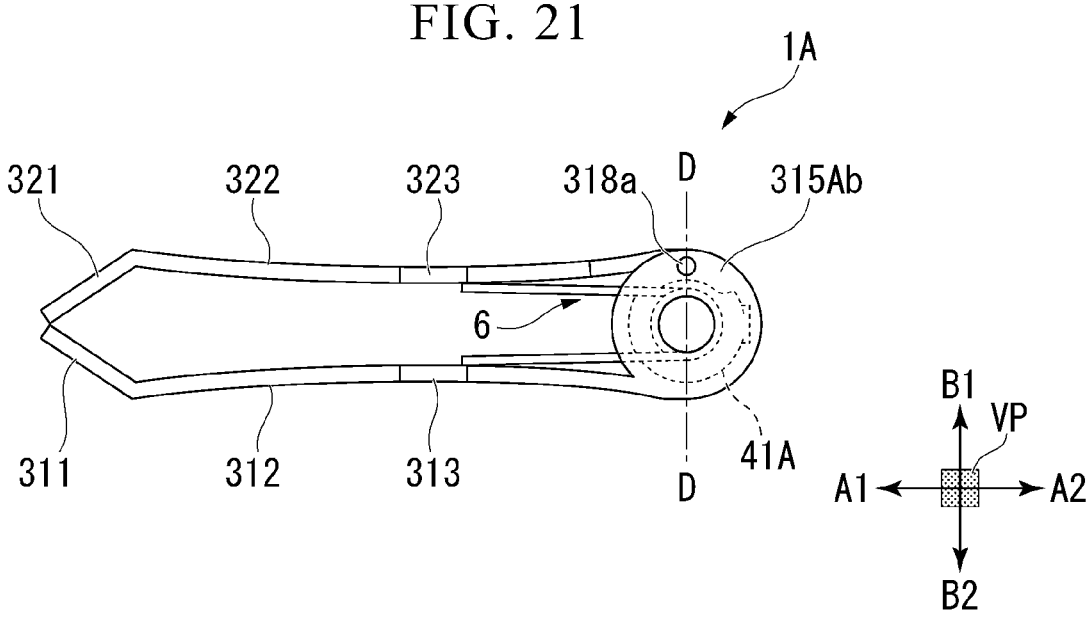
FIG. 21 is a side view showing a closed state of the arm provided in the clip unit of the clip delivery device.
Figure 22:
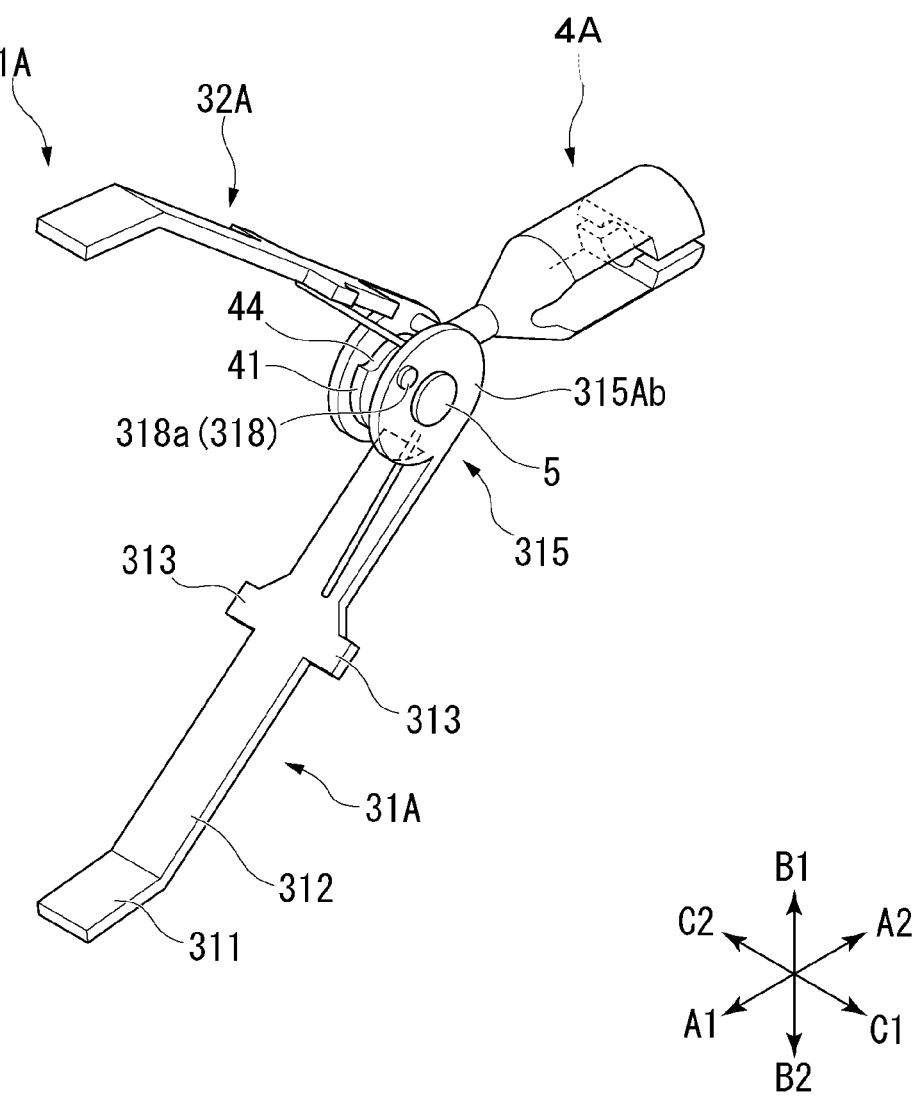
FIG. 22 is a perspective view of the clip unit of the clip delivery device.
Figure 23:
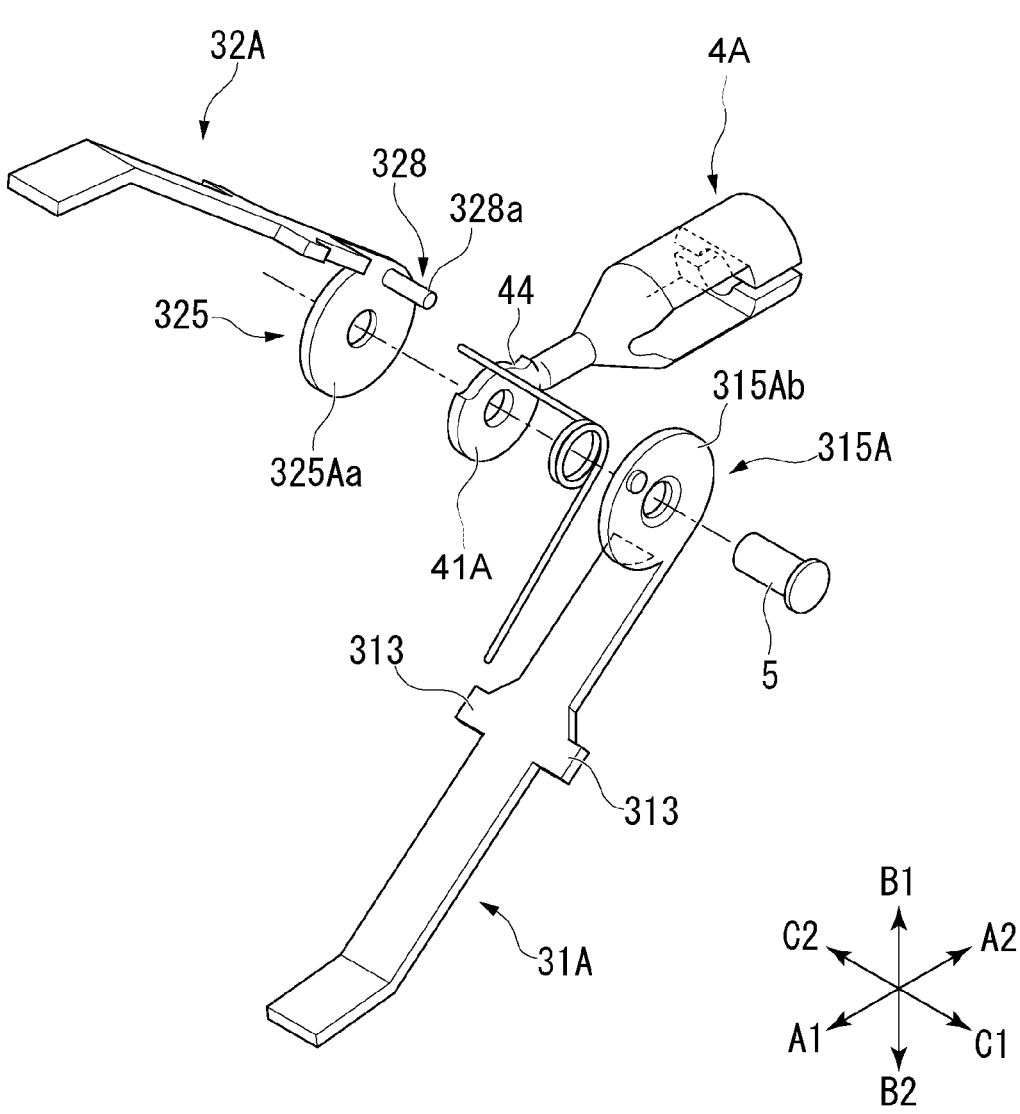
FIG. 23 is a perspective view showing a configuration of each clip unit.

FIG. 20 is a side view showing the open state of the arm 3A provided on the clip unit 1A. FIG. 21 is a side view showing the closed state of the arm 3A provided on the clip unit 1A. FIG. 22 is a perspective view of the clip unit 1A. FIG. 23 is a perspective view showing each configuration of the clip unit 1A.

A clip unit (endoscopic treatment instrument) 1A according to the second embodiment of the present disclosure has a different arm 3A from that of the first embodiment, as shown in FIG. 20. The arm 3A has a first arm 31A and a second arm 32A.

As shown in FIGS. 20 to 23, the first arm 31A has a different lock structure compared to the first embodiment. The first arm 31A does not have the notch portion 317 of the first rotation portion 315, and instead has an uneven portion 318 on the first rotation portion 315A.

Figure 24:
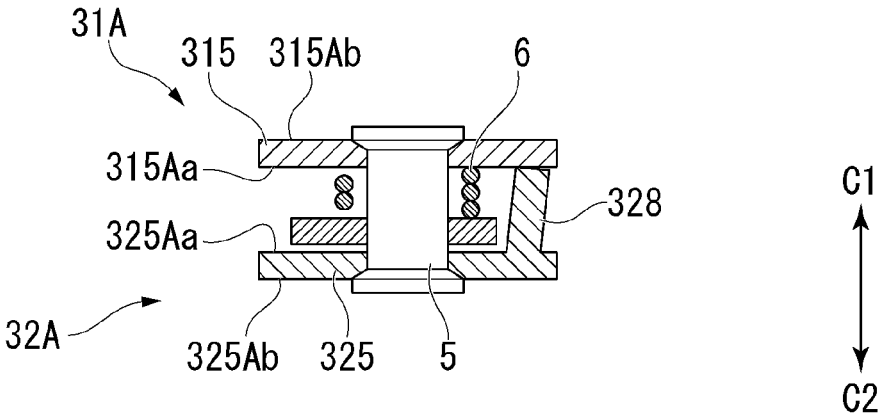
FIG. 24 is a cross-sectional view taken along line C-C shown in FIG. 20 when the arm of the clip unit is in the open state.
Figure 25:
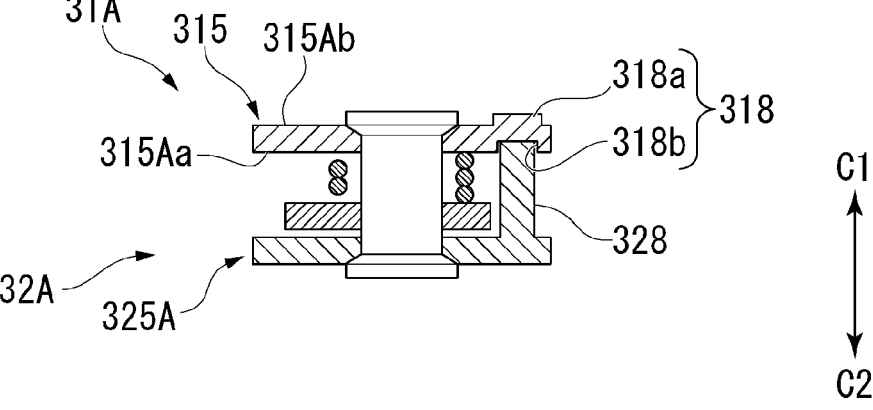
FIG. 25 is a cross-sectional view taken along line D-D shown in FIG. 21 when the arm of the clip unit is in the closed state.

FIG. 24 is a CC sectional view when the arm 3A of the clip unit 1A shown in FIG. 20 is in the open state. FIG. 25 is a DD cross-sectional view when the arm 3A of the clip unit 1A shown in FIG. 21 is in the closed state.

The uneven portion 318 is formed on the first rotation portion 315A. As shown in FIG. 25, the uneven portion 318 includes a substantially cylindrical convex portion 318a on the first rotation outer surface 315Ab. The convex portion 318a protrudes toward the front side C1 in the width direction C from the first rotation outer surface 315Ab. In addition, the uneven portion 318 includes a recessed portion (engaged portion) 318b on the first rotation inner surface 315Aa. As shown in FIG. 25, the recessed portion (engaged portion) 318b is recessed from the first rotation inner surface 315A toward the front side C1 in the width direction C by substantially the same amount as the projecting amount of the convex portion 318a.

The uneven portion 318 can be easily formed at a low cost by subjecting the first rotation inner surface 315A to press work or the like. However, the method for manufacturing the uneven portion 318 is not particularly limited. Further, the uneven portion 318 may not have the convex portion 318a.

The second rotation portion 325A of the second arm 32A has a protruding portion (convex portion, engaging protrusion) 328 instead of the protruding portion 327.

As shown in FIG. 23, the protruding portion (convex portion, engaging protrusion) 328 is provided on the second rotation inner surface 325Aa and is an elastic protruding portion that protrudes toward the first rotation portion 315. The protruding portion 328 is formed in a substantially columnar shape and is elastically deformable. The protruding portion 328 is arranged so that at least the tip 328a abuts against the first inner rotation surface 315Aa of the first rotation portion 315A in an elastically deformed state and biases the first inner rotation surface 315Aa. Further, the protruding portion 328 is slidable with respect to the first rotation inner surface 315Aa while biasing the first rotation inner surface 315Aa.

As shown in FIG. 23, the distal end connecting portion (first connecting portion) 41A has a connecting portion notch portion 44 partially cut away from the side surface toward the center in the circumferential direction, compared to the first embodiment. The connecting portion notch portion 44 is a portion obtained by cutting out a portion where a range in which the protruding portion 328 slides on the first rotation inner surface 315Aa overlaps with the distal end connecting portion 41A when viewed in the width direction C.

Next, the lock structure between the uneven portion 318 provided on the first arm 31A and the protruding portion 328 provided on the second arm 32A will be described.

When the arm 3A is drawn into the internal space S1 of the sheath 220, it moves to the proximal end side A2 as in the first embodiment. The first arm 31A rotates to the closing side R1 in the opening/closing direction R around the first rotation portion 315A as the center of rotation, as shown in FIGS. 21 and 22. In addition, the second arm 32A rotates in the closing direction Q1 in the opening/closing direction Q with the second rotation portion 325A as the center of rotation. As shown in FIG. 24, the protruding portion 328 of the second arm 32A abuts on the first rotation inner surface 315Aa of the first rotation portion 315A in the open state. When the arm 3A is pulled into the internal space S1 of the sheath 220 from the open state, and the first arm 31A and the second arm 32A rotate toward the closing side (the closing direction) of the respective opening/closing directions, the protruding portion 328 slides on the first rotation inner surface 315Aa of the one rotation portion 315A. Since the connecting portion notch portion 44 is formed in the distal end connecting portion 41A of the connection member 4A, the protruding portion 328 does not interfere with the distal end connecting portion 41A of the connection member 4A.

When the arm 3A is further pulled into the sheath 220, the engaging hook portion 313 of the first arm 31A and the engaging hook portion 323 of the second arm 32A come into contact with the peripheral edge 221a on the inner diameter side of the distal tip 221. The engaging hook portion 313 and the engaging hook portion 323 have tapered portions 313a and 323a that slide along the peripheral edge 221a. When the first grasping portion 312 and the second grasping portion 322 are elastically deformed when the tapered portion 313a and the tapered portion 323a slide along peripheral edge 221a, the protruding portion 328 engages with the recessed portion 318b of the uneven portion 318, as shown in FIG. 25. With the above configuration, the rotation of the first arm 31A and the second arm 32A is relatively locked (restricted). Other operations and effects of the clip delivery device are the same as those of the first embodiment, so description thereof will be omitted.

Note that the recessed portion 318b and the protruding portion 328 are not limited to the above embodiment. For example, the recessed portion 318b need not be provided on the first arm 31A, but may be provided on the second rotation portion 325A of the second arm 32A. Moreover, in that case, the protruding portion 328 may not be provided on the second arm 32A, but may be provided on the first rotation portion 315A of the first arm 31A.

In this embodiment, the protruding portion 328 is provided inside the second rotation side surface 325Ac of the second rotation portion 325 (center side of the second rotation portion 325A). Therefore, it is possible to reduce the possibility that the arm 3A will get caught in the tissue inside the body during surgery.

As described above, the second embodiment of the present disclosure has been described in detail with reference to the drawings, but the specific configuration is not limited to this embodiment, and design changes and the like are also included within the scope of the present disclosure. Also, the constituent elements shown in the above-described embodiment and modifications can be combined as appropriate.

Third Embodiment

Next, a third embodiment of the present disclosure will be described with reference to FIGS. 26 to 29. In the following description, the same reference numerals are given to the same configurations as those already described, and redundant descriptions will be omitted. It should be noted that the third embodiment differs from the first embodiment in that the notch portions and protruding portions, which are locking structures, provided in the first rotation portion and the second rotation portion of the clip unit are different. Therefore, in the following description, the differences from the first embodiment will be mainly described.

Figure 26:
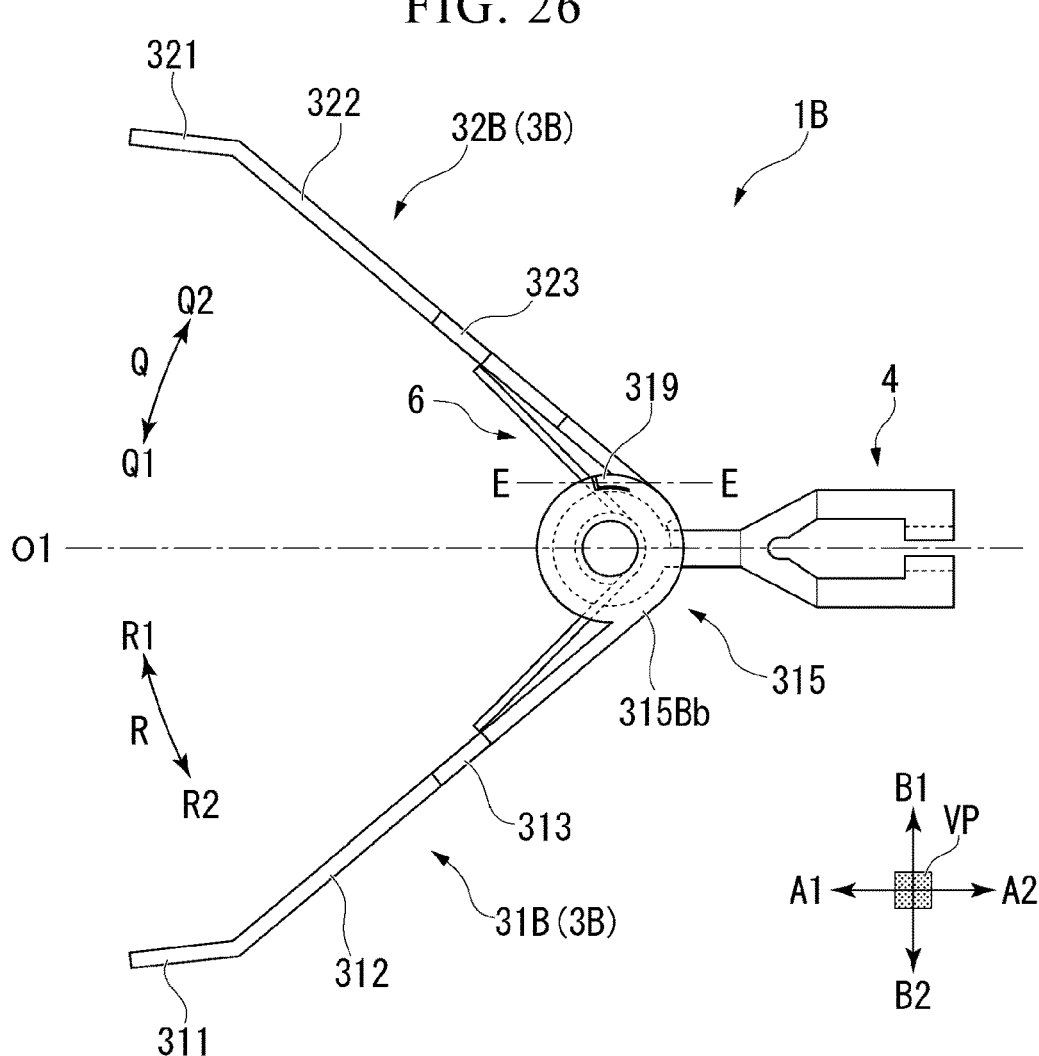
FIG. 26 is a side view showing an open state of an arm provided in a clip unit of a clip delivery device according to a third embodiment.
Figure 27:
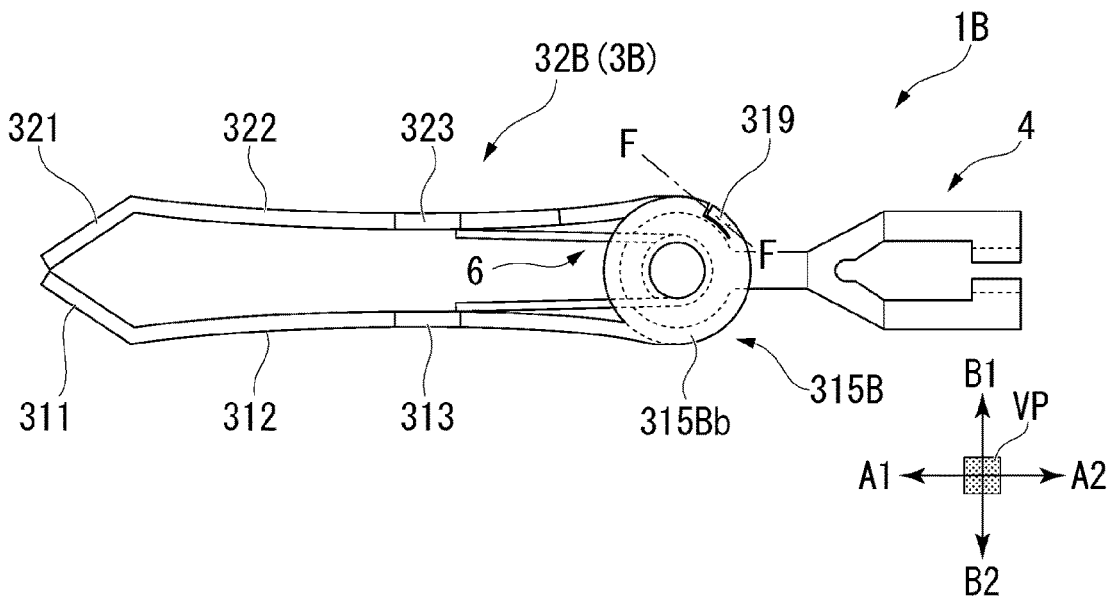
FIG. 27 is a side view showing a closed state of the arm provided on the clip unit.

FIG. 26 is a side view showing the open state of the arm 3B provided on the clip unit 1B. FIG. 27 is aside view showing the closed state of the arm 3B provided on the clip unit 1B.

A clip unit (endoscope treatment tool) 1B according to the third embodiment of the present disclosure has a different arm 3B from that of the first embodiment, as shown in FIG. 26. The arm 3B has a first arm 31B and a second arm 32B.

As shown in FIGS. 26 and 27, the first arm 31B has a different lock structure compared to the first embodiment. The first arm 31B does not have the notch portion 317 of the first rotation portion 315, and instead has a leaf spring portion (engaging protrusion) 319 on the first rotation portion 315B.

Figure 28:
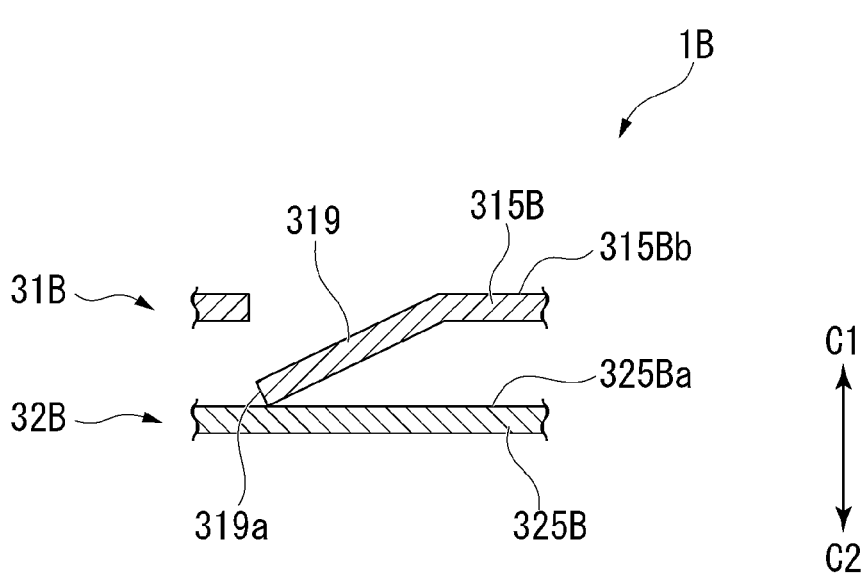
FIG. 28 is a cross-sectional view taken along line E-E shown in FIG. 26 when the arm of the clip unit is in the open state.
Figure 29:
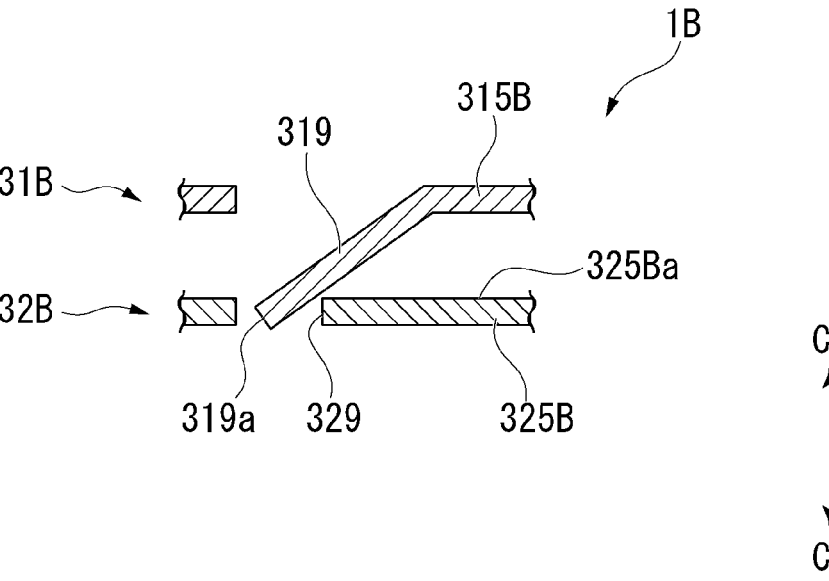
FIG. 29 is a cross-sectional view taken along line F-F shown in FIG. 27 when the arm of the clip unit is in the closed state.

FIG. 28 is an EE cross-sectional view when the arm 3B of the clip unit 1B shown in FIG. 26 is in the open state. FIG. 29 is a cross-sectional view along FF when the arm 3B of the clip unit 1B shown in FIG. 27 is in the closed state.

The leaf spring portion (engaging protrusion) 319 is an elastic portion that protrudes toward the second rotation portion 325B from the first rotation inner surface 315Ba of the first rotation portion 315B. In this embodiment, as shown in FIG. 28, the leaf spring portion 319 is formed by cutting a portion of the peripheral edge of the first rotation portion 315B along the circumference of the first rotation portion 315B. The leaf spring portion 319 protrudes to the back side C2 in the width direction C. The leaf spring portion 319 is arranged so that at least the distal end 319a abuts against the second inner rotation surface 325Ba of the second rotation portion 325B in an elastically deformed state and biases the second inner rotation surface 325Ba. Further, the leaf spring portion 319 is slidable with respect to the second inner rotation surface 325Ba while biasing the second inner rotation surface 325Ba.

The leaf spring portion 319 can be easily formed at low cost by cutting out a portion of the first rotation portion 315B. However, the manufacturing method of the leaf spring portion 319 is not particularly limited. The leaf spring portion 319 may be formed of a different member from, for example, the first rotation portion 315B.

The second rotation portion 325B of the second arm 32B does not have the protruding portion 327. The second rotation portion 325B has a through-hole (engaged portion) 329.

As shown in FIG. 29, the through-hole (engaged portion) 329 is provided on the second rotation inner surface (second inner surface) 325Ba of the second rotation portion 325B. In addition, the through-hole 329 is a hole penetrating in the width direction C. However, the through-hole 329 may be a recess or the like that is recessed in the second rotation inner surface 325Ba.

Next, the locking structure between the leaf spring portion 319 provided on the first arm 31B and the through-hole 329 provided on the second arm 32B will be described.

When the arm 3B is drawn into the internal space S1 of the sheath 220, it moves to the proximal end side A2 as in the first embodiment. The first arm 31B rotates to the closing side R1 in the opening/closing direction R around the first rotation portion 315B as the center of rotation, as shown in FIGS. 26 and 27. Further, the second arm 32B rotates in the closing direction Q1 in the opening/closing direction Q with the second rotation portion 325B as the center of rotation. As shown in FIG. 28, the leaf spring portion 319 of the first arm 31B abuts on the second inside rotation surface 325Ba of the second rotation portion 325B in the open state. When the arm 3B is pulled into the internal space S1 of the sheath 220 from the open state, and the first arm 31B and the second arm 32B rotate toward the closing side (the closing direction) of the respective opening/closing directions as shown in FIG. 27, the leaf spring portion 319 slides on the second rotation inner surface 325Ba of the second rotation portion 325B.

When the arm 3B is further pulled into the sheath 220, the engaging hook portion 313 of the first arm 31B and the engaging hook portion 323 of the second arm 32B come into contact with the peripheral edge 221a on the inner diameter side of the tip 221. The engaging hook portion 313 and the engaging hook portion 323 have tapered portions 313a and 323a that slide along the peripheral edge 221a. When the first grasping portion 312 and the second grasping portion 322 are elastically deformed when the tapered portion 313a and the tapered portion 323a slide along the peripheral edge 221a, the leaf spring portion 319 is engaged with the through-hole 329 of the second rotation portion 325 as shown in FIG. 29. With the above configuration, the rotation of the first arm 31B and the second arm 32B is relatively locked (restricted). Other operations and effects of the clip delivery device are the same as those of the first embodiment, so description thereof will be omitted.

It should be noted that the leaf spring portion 319 and the through-hole 329 are not limited to the above embodiment. For example, the leaf spring portion 319 need not be provided on the first arm 31B, but may be provided on the second rotation portion 325B of the second arm 32B. Moreover, in that case, the through-hole 329 may not be provided in the second arm 32B, but may be provided in the first rotation portion 315B of the first arm 31B.

Also in this case, in the present embodiment, the leaf spring portion 319 is provided inside the peripheral edge of the first rotation portion 315B (center side of the first rotation portion 315B). Therefore, it is possible to reduce the possibility that the arm 3A will get caught in the tissue inside the body during surgery.

As described above, the third embodiment of the present disclosure has been described in detail with reference to the drawings, but the specific configuration is not limited to this embodiment, and design changes and the like are included within the scope of the present disclosure. Also, the constituent elements shown in the above-described embodiment and modifications can be combined as appropriate.

Fourth Embodiment

Next, a fourth embodiment of the disclosure will be described with reference to FIGS. 30 to 42. In the following description, the same reference numerals are given to the same configurations as those already described, and redundant descriptions will be omitted. It should be noted that the following embodiments all differ from the first embodiment in the wire of the clip-introducing device, the clip unit, and the cartridge. Therefore, in the following description, the differences from the first embodiment will be mainly described.

Figure 30:
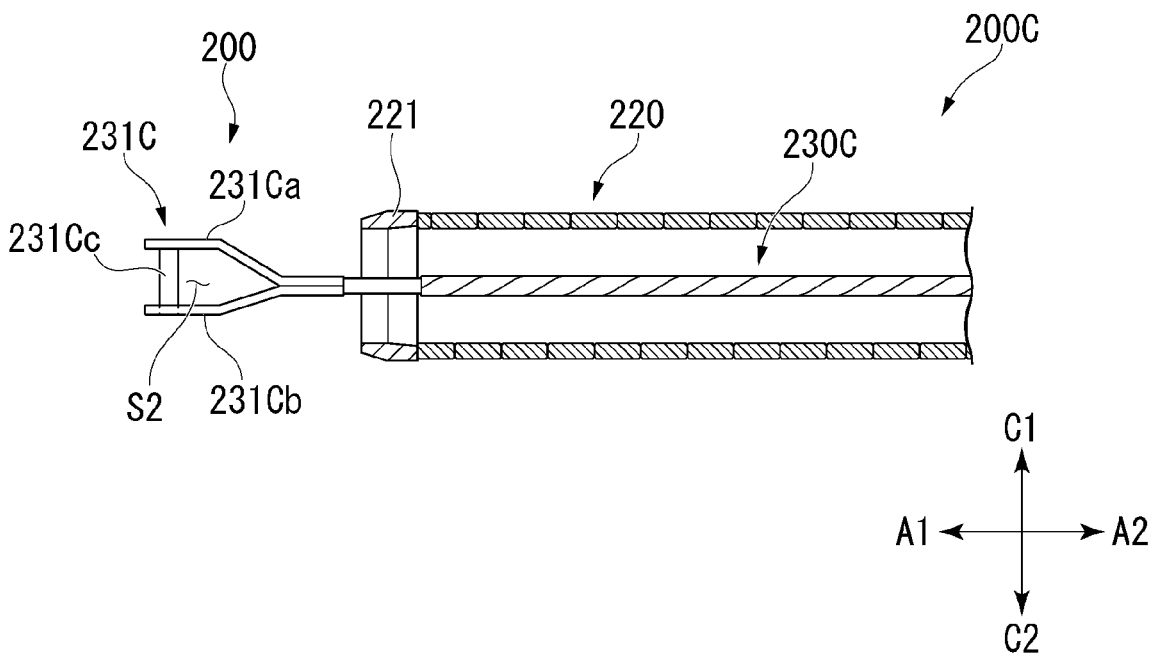
FIG. 30 is an enlarged plan view of a distal end side of an operation wire provided in a clip-introducing device of a clip delivery device according to a fourth embodiment.
Figure 31:
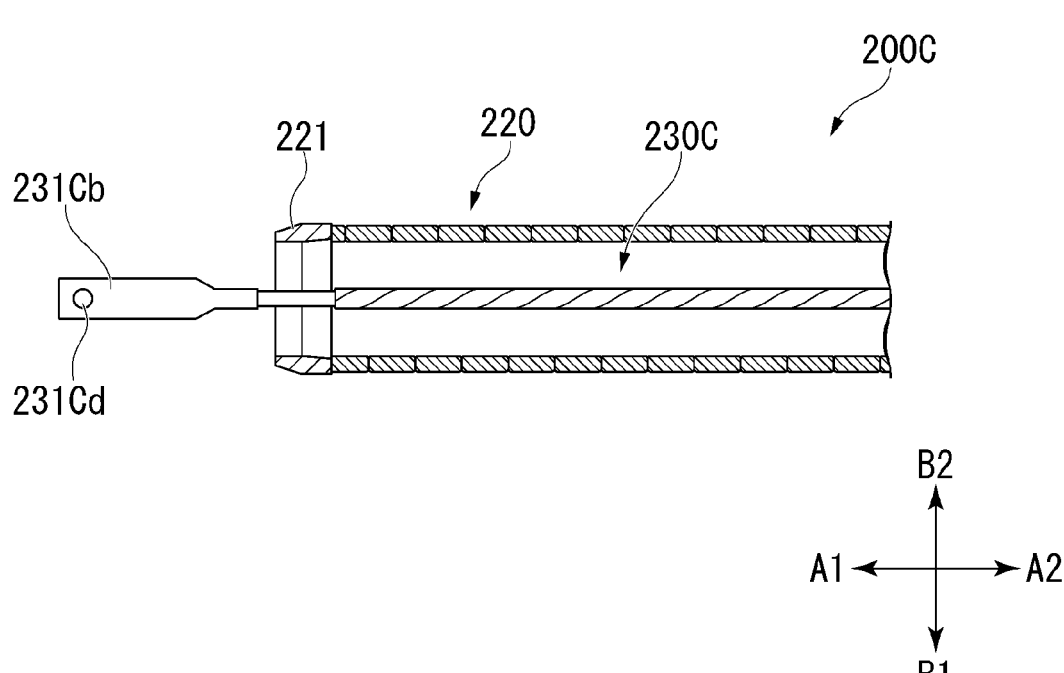
FIG. 31 is an enlarged side view of the distal end side of the operation wire of the clip-introducing device.

FIG. 30 is an enlarged plan view of the distal end side of the operation wire 230C provided in the clip-introducing device 200C of the clip delivery device 300C according to the fourth embodiment. FIG. 31 is an enlarged side view of the distal end side of the operation wire 230C of the clip-introducing device 200C.

The operation wire 230C includes a connecting hook portion (hook portion) 231C connected to the clip unit (endoscope treatment instrument) 1C. The connecting hook portion 231C is formed with the member which can be elastically deformed. Further, the connecting hook portion 231C includes an upper jaw 231Ca and a lower jaw 231Cb. The upper jaw 231Ca is provided on the front side C1 of the operation wire 231C, and the lower jaw 231Cb is provided on the back side C2 of the operation wire 231C. The upper jaw 231Ca and the lower jaw 231Cb are, for example, plate-like members having surfaces facing each other, and a gap S2 is provided between the upper jaw 231Ca and the lower jaw 231Cb.

As shown in FIG. 30, the upper jaw 231Ca has a clip connecting pin 231Cc extending in the width direction C on the surface facing the lower jaw 231Cb. The clip connecting pin 231Cc may be formed of a member that deforms and breaks when a predetermined amount of breaking force is applied to the clip connecting pin 231Cc, like the separating portion 43 of the first embodiment. Moreover, the lower jaw 231Cb is provided with a pin through-hole 231Cd penetrating in the width direction C, as shown in FIG. 31. The clip connecting pin 231Cc extends toward the lower jaw 231Cb in the gap S2 and fits into the pin through-hole 231Cd.

Figure 32:
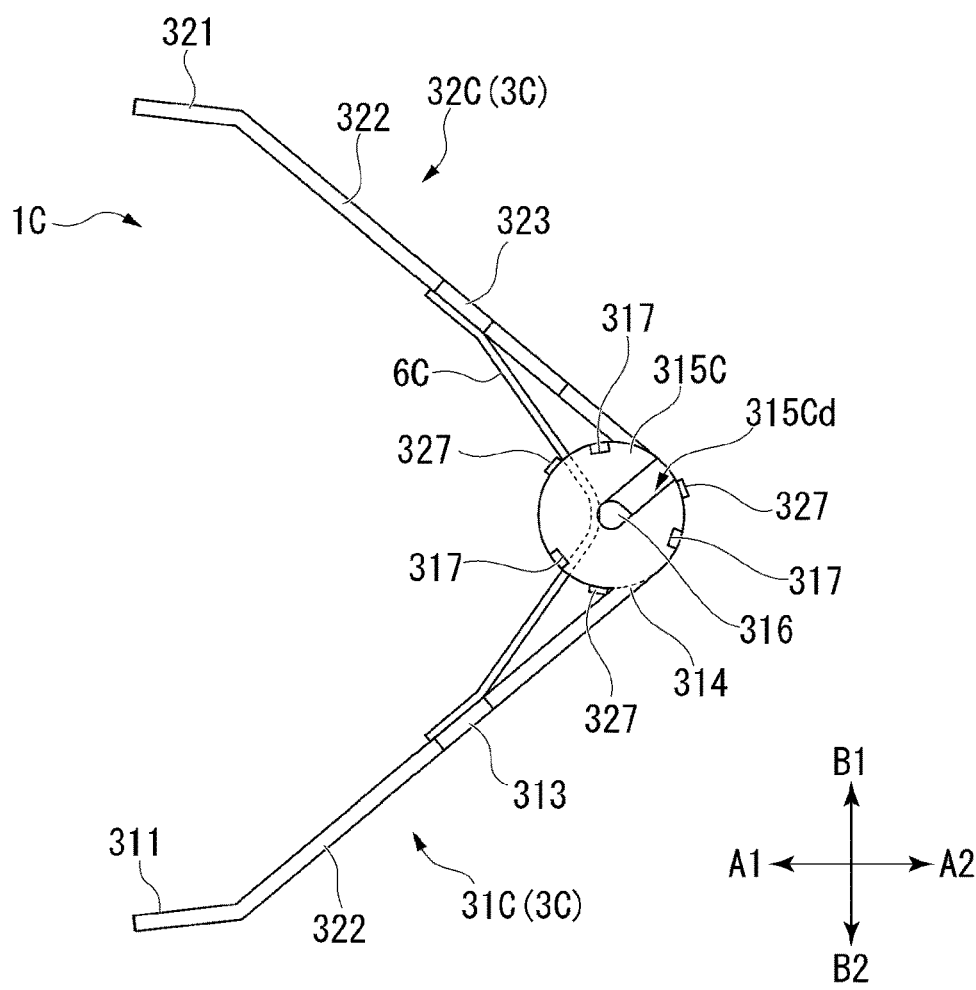
FIG. 32 is a side view showing an open state of an arm provided in a clip unit of the clip delivery device.
Figure 33:
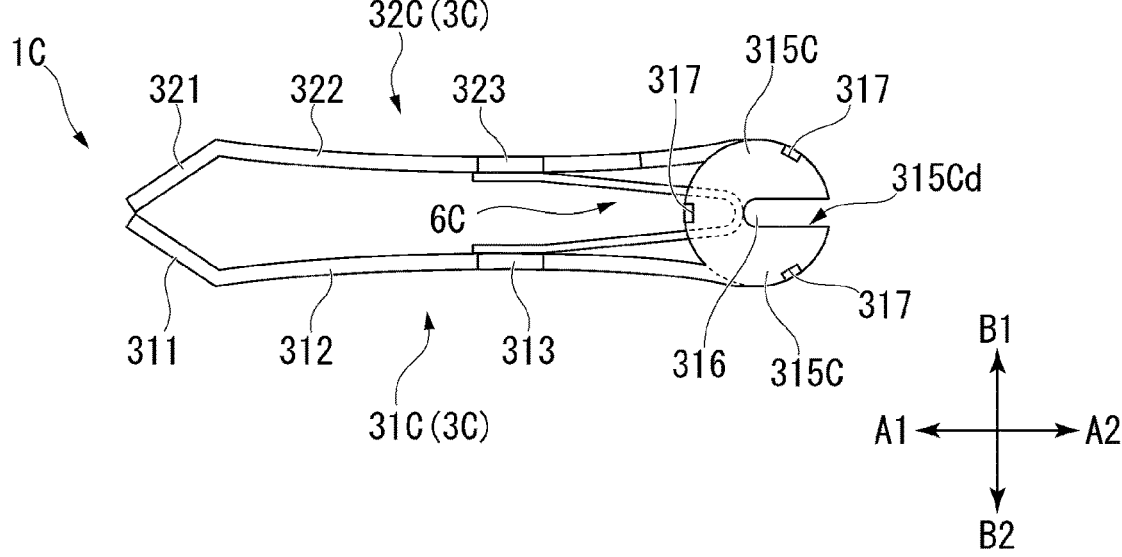
FIG. 33 is a side view showing a closed state of the arm provided in the clip unit.
Figure 34:
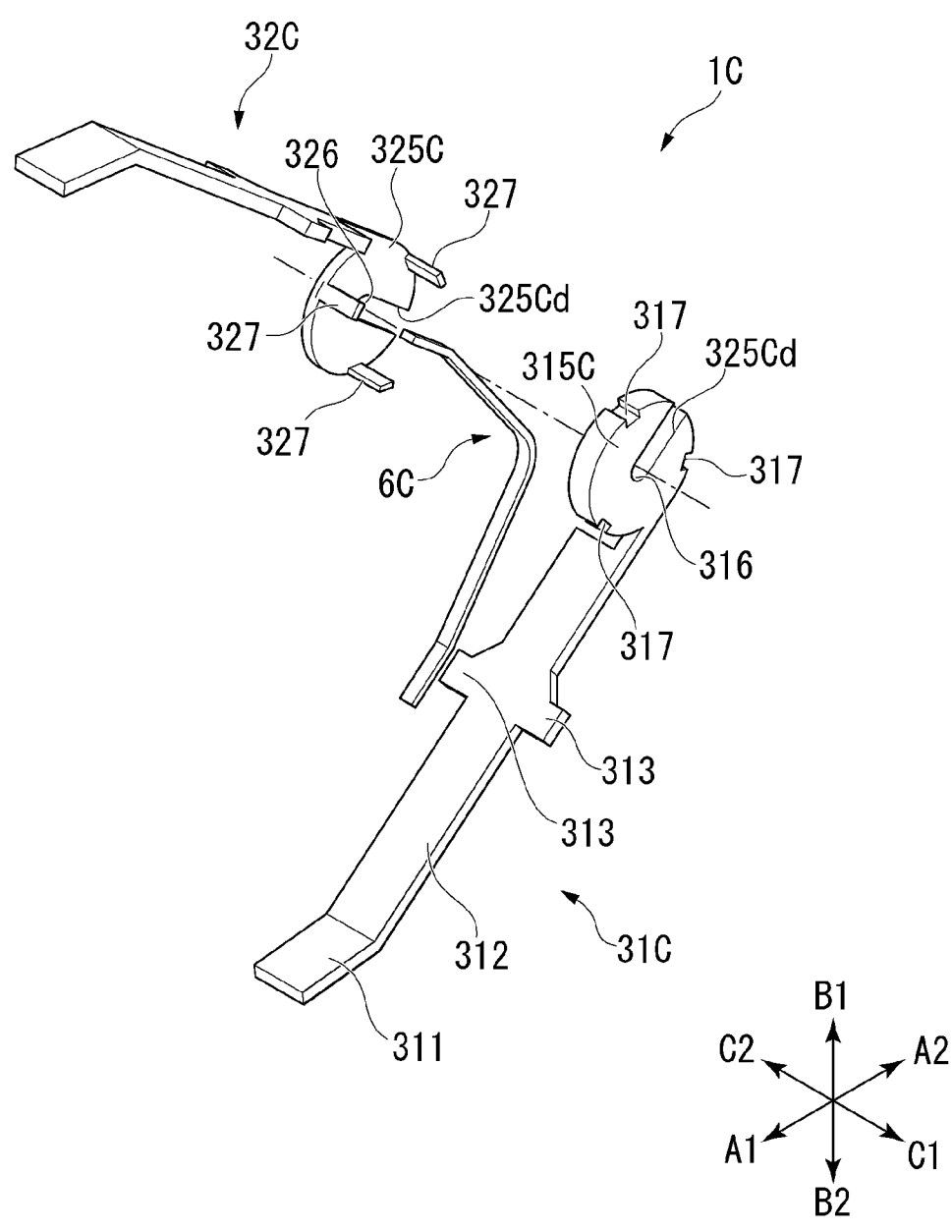
FIG. 34 is a perspective view showing a configuration of each clip unit.

FIG. 32 is a side view showing the open state of the arm 3C provided on the clip unit 1C. FIG. 33 is a side view showing the closed state of the arm 3C provided on the clip unit 1C. FIG. 34 is a perspective view showing each configuration of the clip unit 1C.

The clip unit 1C does not have the connection member 4 and the connecting pin 5 in this embodiment as compared with the first embodiment. The clip unit 1C includes only an arm 3C and a biasing member (biasing portion) 6C.

A first arm 31C of the arm 3C has a plurality of notch portions 317 compared to the first embodiment. The first arm 31C also has a first groove portion 315Cd formed from the peripheral edge of the first arm 31C toward the first through-hole 316 into which the clip connecting pin 231Cc is fitted. The width of the first groove portion 315Cd is approximately the same length as the diameter of the first through-hole 316. Also, the width of the first groove portion 315Cd may be designed to be slightly larger than the diameter of the clip connecting pin 231Cc provided in the upper jaw 231Ca. The first groove portion 315Cd serves as a path for the clip connecting pin 231Cc.

The second arm 32C of the arm 3C has a plurality of protruding portions 327, as shown in FIGS. 32 to 34, as compared with the first embodiment. Further, the second arm 32C has a second groove portion 325Cd formed from the peripheral edge of the second arm 32C toward the second through-hole 326 into which the clip connecting pin 231Cc is fitted. The width of the second groove portion 325Cd is approximately the same length as the diameter of the second through-hole 326.

The first groove portion 315Cd and the second groove portion 325Cd do not overlap in the width direction C in states other than the closed state. The first groove portion 315Cd and the second groove portion 325Cd overlap along the longitudinal direction A in the width direction C when the first groove portion 315Cd and the second groove portion 325Cd are in the closed state.

As shown in FIG. 34, for example, a leaf spring is used as the biasing member (biasing portion) 6C in this embodiment. The biasing members 6C do not have the coil portion 61 compared with the first embodiment. The connecting portion between the first connecting portion 62 and the second connecting portion 63 of the biasing member 6C is formed in a substantially U-shape, and is provided on the distal end side A1 from the first through-hole 326 of the first rotation portion 315C and the second through-hole 326 of the second rotation portion 325C.

Figure 35:
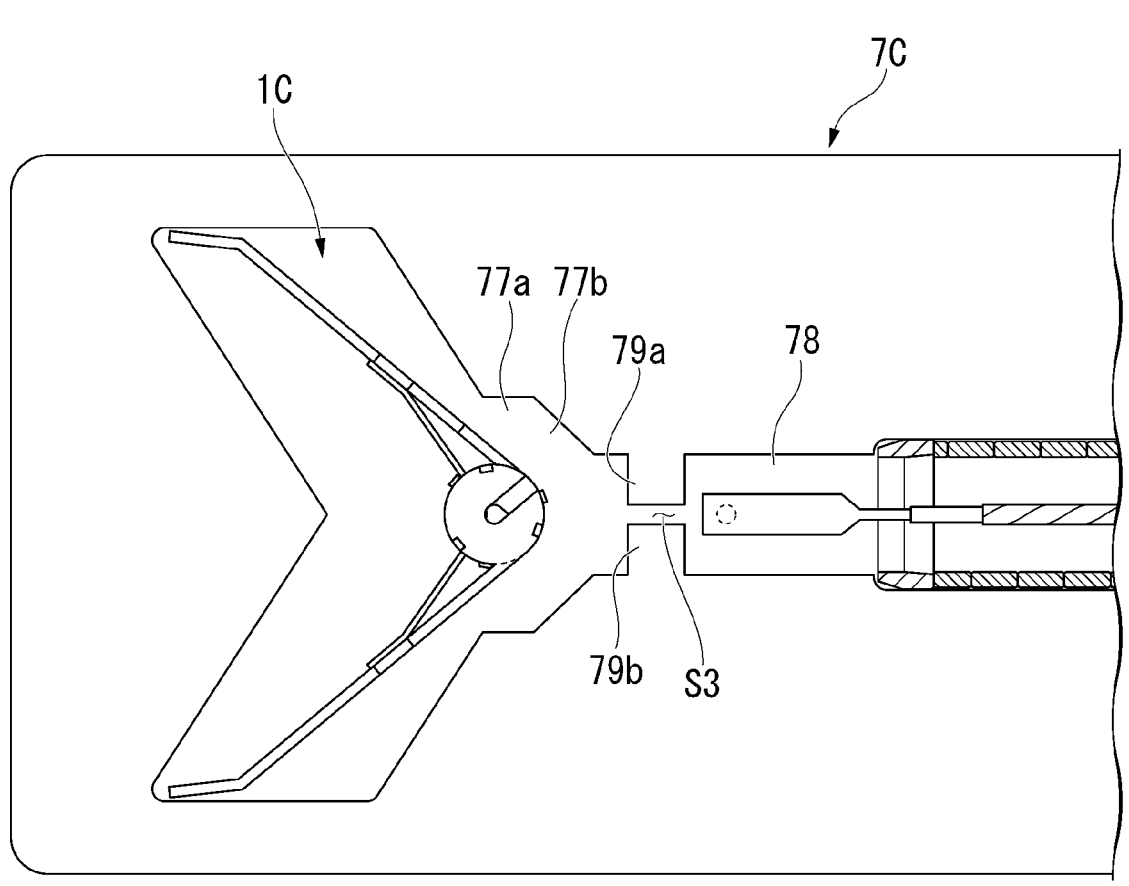
FIG. 35 is a schematic partial cross-sectional view enlarging a distal end side of a cartridge for loading the clip unit into the clip-introducing device.
Figure 35:
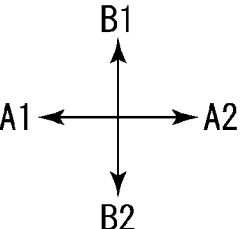
Figure 36:
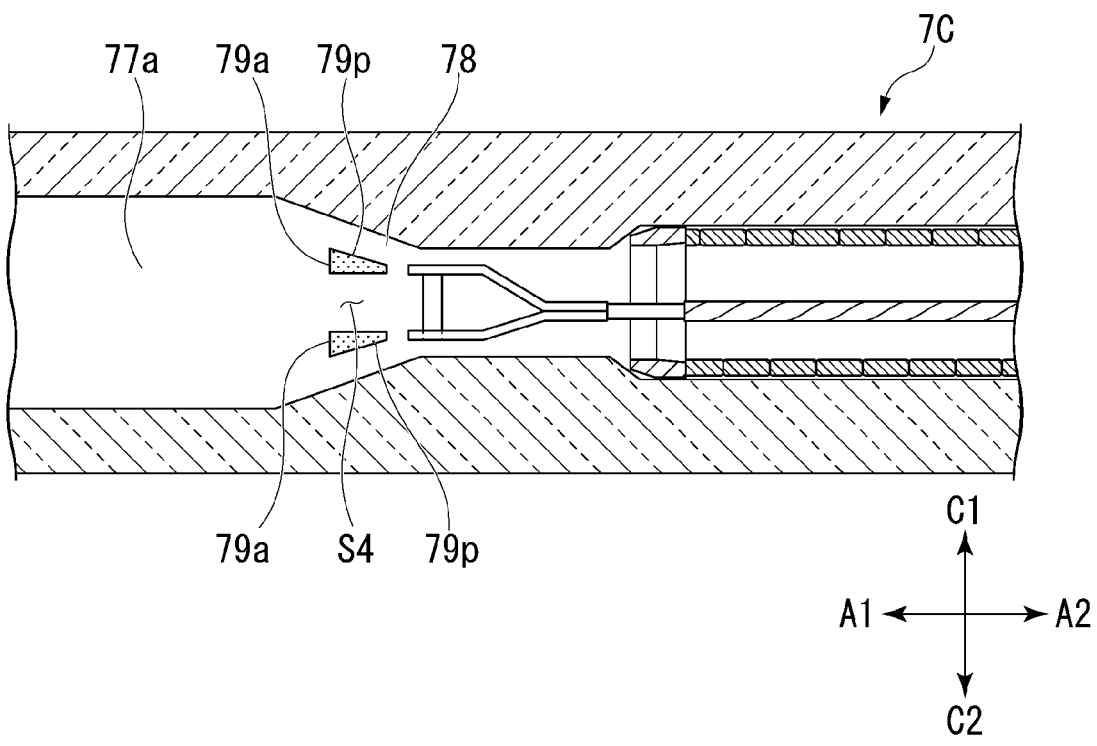
FIG. 36 is a schematic partial side view enlarging the distal end side of the cartridge.
Figure 37:
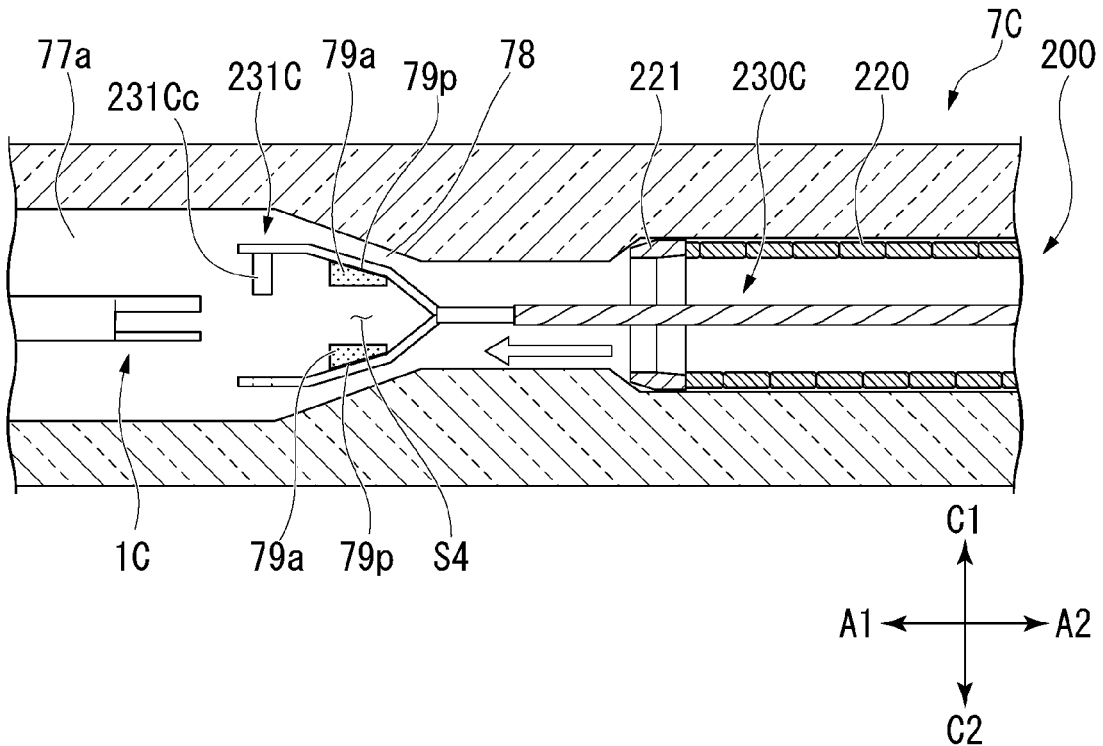
FIG. 37 is a schematic partial side view enlarging a connecting hook portion passing through a hook extension portion of the cartridge.

FIG. 35 is a schematic partial cross-sectional view enlarging the distal end side A1 of the cartridge 7C. FIG. 36 is a schematic partial side view enlarging the distal end side A1 of the cartridge 7C. FIG. 37 is an enlarged schematic partial side view of the connecting hook portion 231C passing through the hook extension portion 79 of the cartridge 7C.

As shown in FIG. 35, the cartridge 7C has a shorter length in the longitudinal direction A of the proximal end connecting portion enlarged diameter portion 77a compared to the first embodiment. Further, the cartridge 7C is provided with a hook extension portion 79 extending from the inner wall of the connection member housing portion 78 toward the center of the cartridge 7C.

A plurality of hook extension portions 79 are provided, and for example, include a first hook extension portion 79a protruding from the upper side B1 of the inner wall of the connection member housing portion 78 toward the center of the cartridge 7C, and a second hook extension portion 79b protruding from the lower side B2 of the inner wall of the connection member housing portion 78 toward the center of the cartridge 7C. Two first hook extension portions 79a are provided in the width direction C, as shown in FIG. 36. Although not shown, two second hook extensions 79b are also provided like the first hook extension portions 79a. As shown in FIGS. 36 and 37, each of the first hook extension portion 79a and the second hook extension portion 79b has a guide portion 79p that is inclined so that the end portion in the width direction C widens from the proximal end side A2 toward the distal end side A1 in the longitudinal direction A.

The first hook extension portion 79a and the second hook extension portion 79b have a gap S3 when viewed from the width direction C, as shown in FIG. 35. Also, as shown in FIGS. 36 and 37, the first hook extension portion 79a and the second hook extension portion 79b have a gap S4 when viewed from the vertical direction B.

Next, operations and actions of the clip delivery device 300C according to the fourth embodiment will be described with reference to FIGS. 38 to 42.

First, with reference to FIGS. 38 to 40, a method of attaching (reloading) the clip unit 1C using the cartridge 7C to the clip-introducing device 200C will be described. Since the insertion step is the same as in the first embodiment, the description is omitted.

Figure 38:
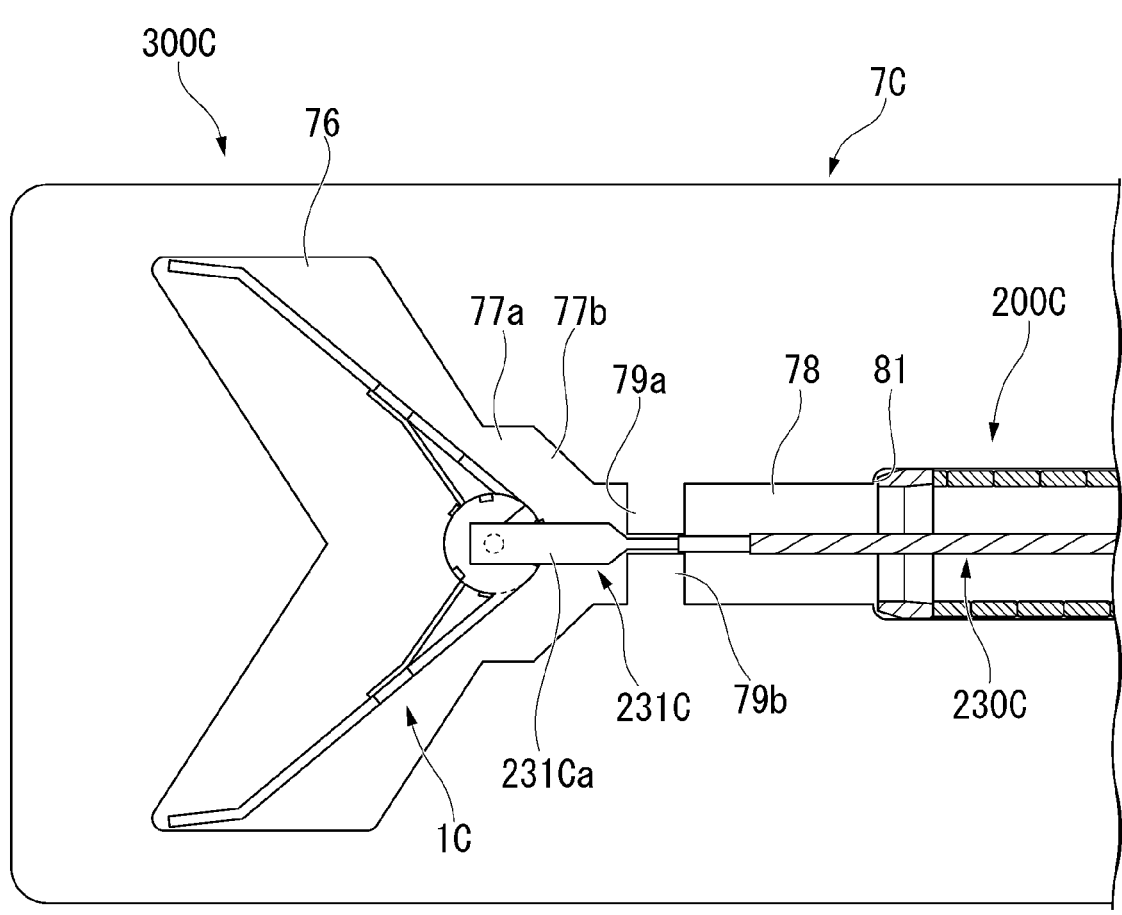
FIG. 38 is a plan view showing a loading step for the clip-introducing device.
Figure 38:
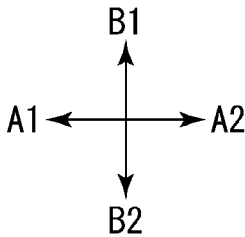
Figures 39, 40:
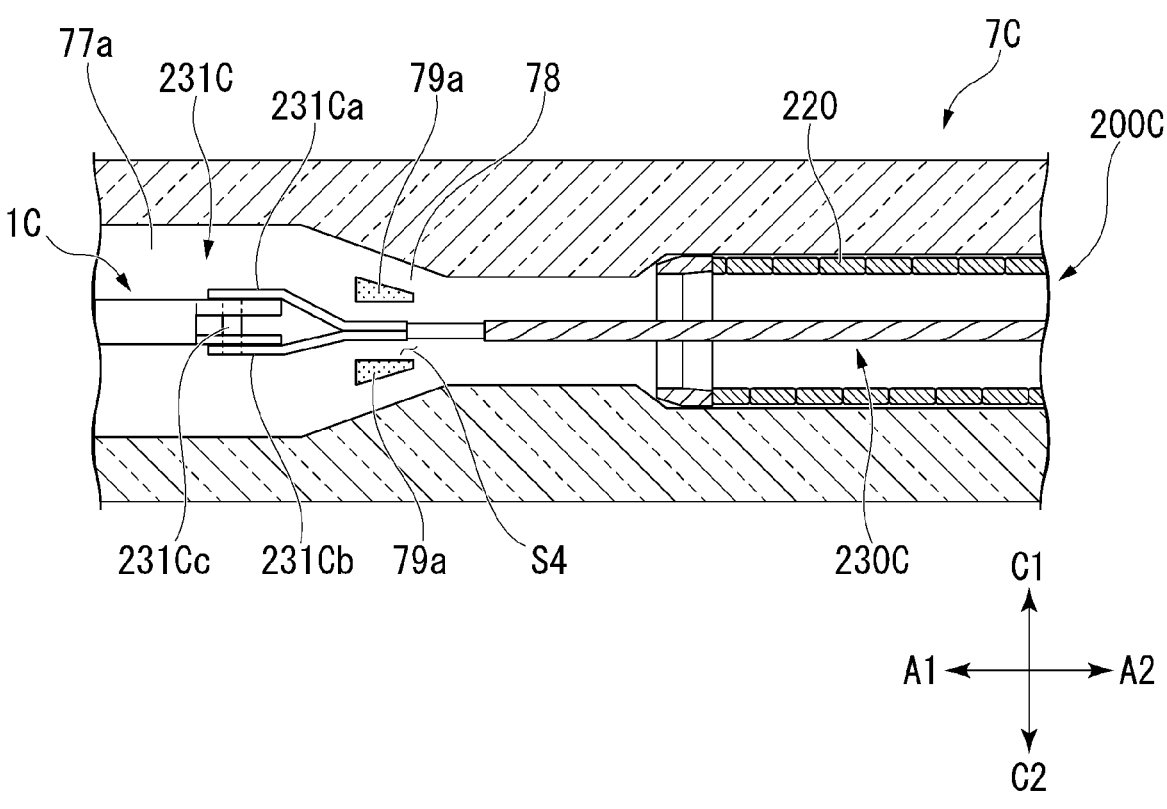
FIG. 39 is a side view showing a loading step for the clip-introducing device.
FIG. 40 is a view showing the clip delivery device after loading.

FIGS. 38 and 39 are diagrams showing the loading step of the clip-introducing device 200. FIG. 40 shows clip delivery device 300C after loading.

As shown in FIG. 38, the operator operates the operation portion 240 to advance the operation wire 230C with respect to the sheath 220, thereby advancing the connecting hook portion 231C. The connecting hook portion 231C has a clip connecting pin 231Cc extending in the width direction C in the gap S2 between the upper jaw 231Ca and the lower jaw 231Cb. Further, the cartridge 7C is provided with a hook extension portion 79 extending from the inner wall of the connection member housing portion 78 toward the center of the cartridge 7C. However, since the first hook extension portion 79*a* and the second hook extension portion 79*b* of the hook extension portion 79 are provided with a gap S3 when viewed from the width direction C, the connecting hook portion 231C smoothly moves into the connection member housing portion 78.

Then, when the connecting hook portion 231C moves forward, the upper jaw 231Ca and the lower jaw 231Cb are widened by the inclined guide portion 79*p* (see FIG. 37). As shown in FIG. 39, the clip connecting pin 231Cc of the connecting hook portion 231C is fitted into the first through-hole 326 of the first rotation portion 315C and the second through-hole 326 of the second rotation portion 325C. By thus connecting the arm 3C of the clip unit 1C and the connecting hook portion 231C, the clip unit 1C accommodated in the cartridge 7C is loaded into the clip-introducing device 200C.

<Pulling Step>

The operator pulls the operation wire 230C to the proximal end side A2. The first hook extension portion 79*a* and the second hook extension portion 79*b* have a gap S4 when viewed from the vertical direction B, as shown in FIG. 39. Therefore, the connecting hook portion 231C of the operation wire 230C can pass through the gap S4 and move toward the proximal end side A2 while the clip unit 1C is connected to the connecting hook portion 231C.

The contraction step and the extracting step are the same as in the first embodiment, so the description is omitted. The operator can use the cartridge 7C to load the clip-introducing device 200C with the clip unit 1C as shown in FIG. 40.

Next, a clip release method for the clip delivery device 300C will be described with reference to FIGS. 41 and 42. Note that the arm-opening step, the pulling step, the arm accommodating step, the sliding step of the protruding portion 327, the re-grasping step, and the deforming step are the same as those in the first embodiment, so description thereof will be omitted.

<Lock-Setting Step>

Figure 41:
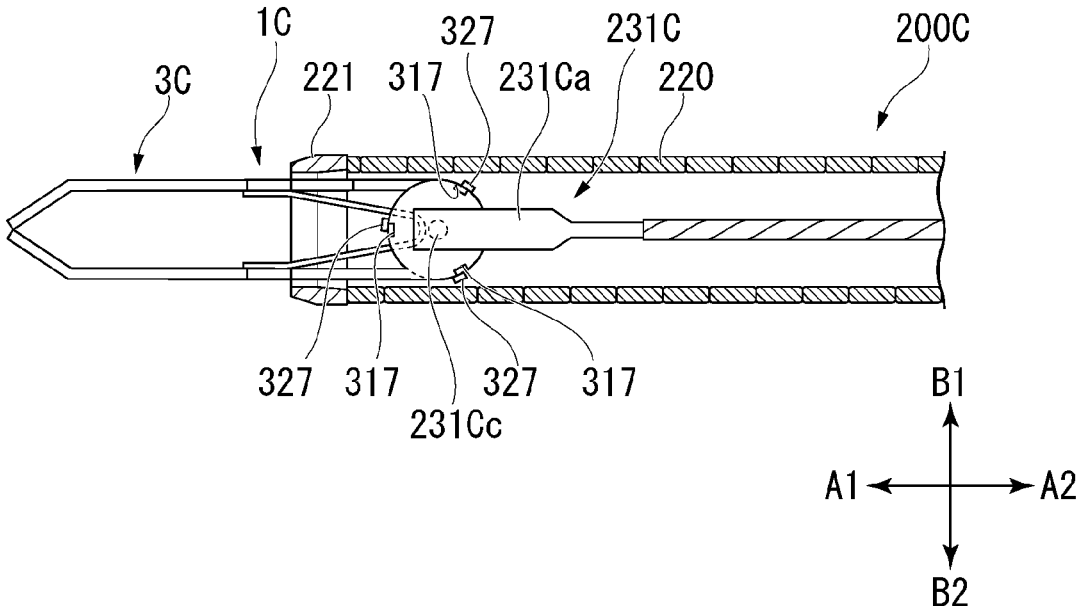
FIG. 41 is a diagram showing lock setting and connection release steps for the clip unit.
Figure 42:
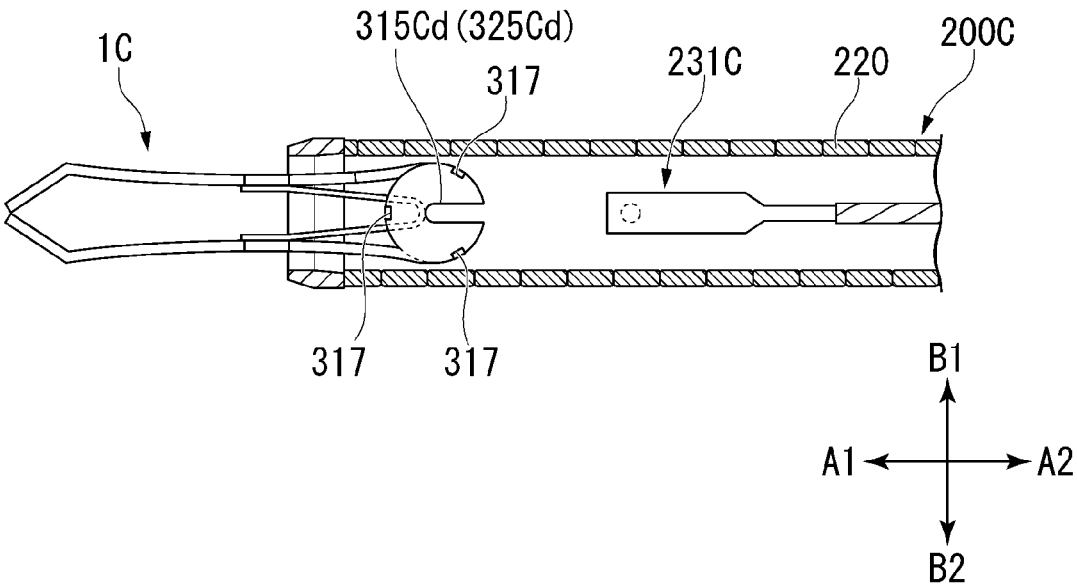
FIG. 42 is a diagram showing lock setting and connection release steps for the clip unit.

FIGS. 41 and 42 are diagrams showing lock setting and connection release steps for the clip unit 1C.

When the arm 3C is pulled into the sheath 220, the first grasping portion 312 and the second grasping portion 322 are elastically deformed as in the first embodiment. When the first grasping portion 312 and the second grasping portion 322 are elastically deformed, the plurality of protruding portions 327 are engaged with the plurality of notch portions 317 as shown in FIGS. 41 and 42. With the above configuration, the rotation of the first arm 31 and the second arm 32 is relatively locked (restricted). The first groove portion 315Cd and the second groove portion 325Cd overlap along the longitudinal direction A in the width direction C.

<Connection Release Step>

By retracting the slider 242 along the operation portion main body 241, the operator retracts the clip unit 1C loaded on the connecting hook portion 231C. Then, the clip connecting pin 231Cc of the connecting hook portion 231C passes through the first groove portion 315Cd and the second groove portion 325Cd and is removed from the clip unit 1C. That is, when the connecting hook portion 231C is pulled out along the groove of the arm 3C, the clip-introducing device 200C and the clip unit 1C are separated, and the clip unit 1C is left inside the body.

According to the clip unit 1C according to this embodiment, the connection member 4 and the connecting pin 5 are not required as compared with the first embodiment. Therefore, the time and cost involved in manufacturing can be reduced.

In addition, the clip delivery device 300C according to the present embodiment can place the entire clip unit 1C without using the connection member 4 and the connecting pin 5 as compared with the first embodiment. Therefore, the operator can smoothly load the next clip unit 1C into the clip-introducing device 200C.

As described above, the fourth embodiment of the present disclosure has been described in detail with reference to the drawings, but the specific configuration is not limited to this embodiment, and design changes and the like are included within the scope of the present disclosure. Also, the constituent elements shown in the above-described embodiment and modifications can be combined as appropriate.

Fifth Embodiment

Next, a fifth embodiment of the present disclosure will be described with reference to FIGS. 43 to 48. In the following description, the same reference numerals are given to the same configurations as those already described, and redundant descriptions will be omitted. It should be noted that each of the following embodiments differs from the first embodiment in the clip-introducing device and the cartridge. Therefore, in the following description, the differences from the first embodiment will be mainly described. Note that the clip unit is the same as the clip unit 1 of the first embodiment, except that the arm does not have a locking hook.

Figure 43:
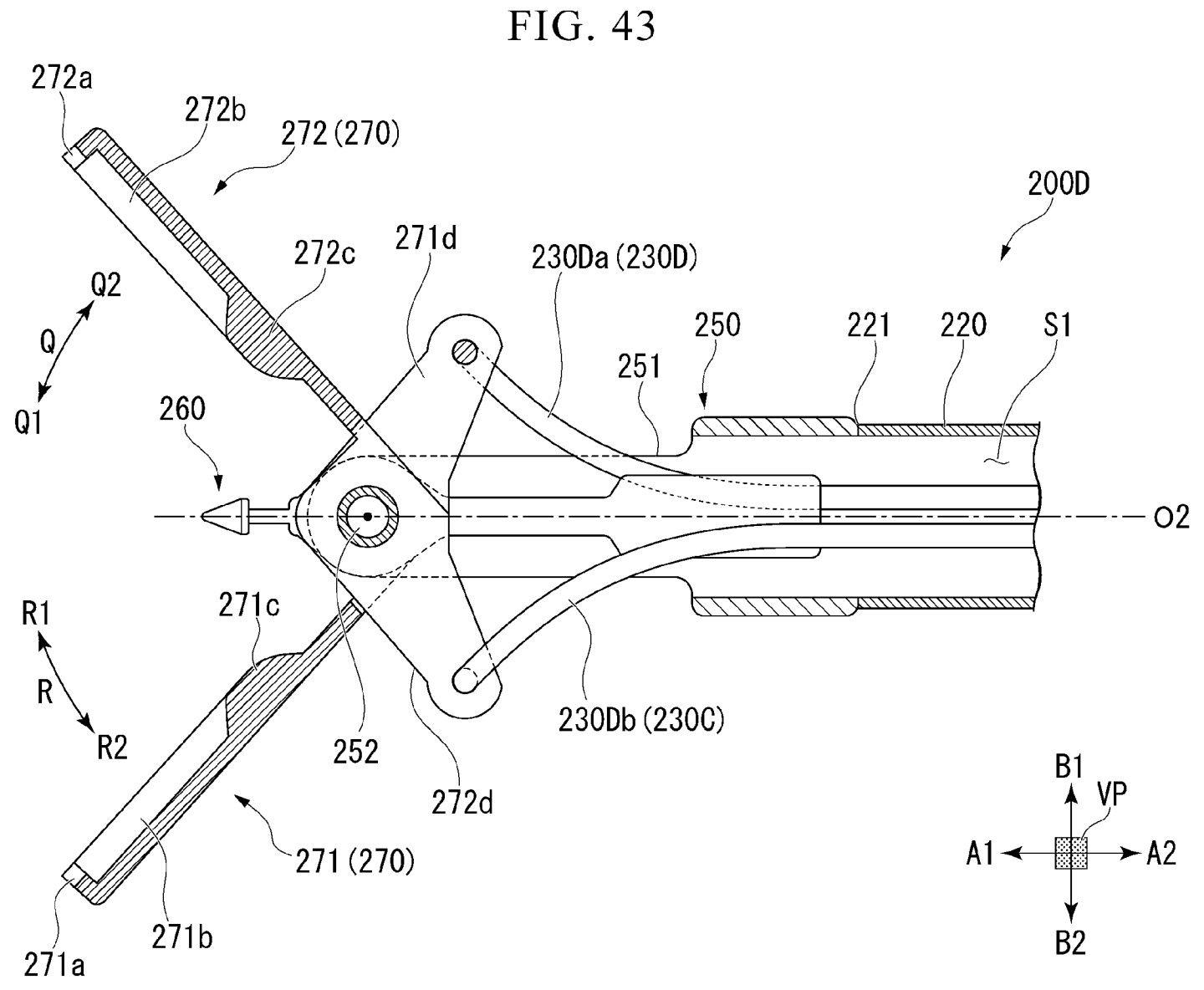

FIG. 43 is an enlarged side view of the distal end side of the clip-introducing device 200D of the clip delivery device according to the fifth embodiment.

The clip-introducing device 200D includes an operation wire 230D, a support member 250, an arrowhead hook portion (hook portion) 260, and forceps 270.

The operation wire 230D includes a first operation wire 230Da and a second operation wire 230Db, as shown in FIG. 43. The first operation wire 230Da and the second operation wire 230Db pass through the inner space S1 of the sheath 220.

In the present embodiment, the proximal ends of the first operation wire 230Da and the second operation wire 230Db are attached to the slider 242 of the operation portion 240, and two wires can be operated at the same time, but the present disclosure is not particularly limited. For example, the clip-introducing device 200D may have different operation portions for the first operation wire 230Da and the second operation wire 230Db.

As shown in FIG. 43, the support member 250 is attached to the distal tip 221 of the sheath 220 by caulking or the like, and supports the arrowhead hook portion 260 and the forceps 270. The support member 250 is made of metal such as stainless steel and is formed in a substantially U-shape. The support member 250 has a frame 251 and a rotation shaft member 252.

The frame 251 is a pair of plate members formed on both sides of the central axis O2 of the clip-introducing device 200D in the width direction C. The frame 251 extends in the longitudinal direction A on the distal end side A1 of the support member 250 and is formed along the vertical plane VP. A through-hole 251h which penetrates in the width direction C is provided in the distal end side A1 of a pair of flame 251.

The rotation shaft member 252 is formed in a substantially cylindrical shape. The rotation shaft member 252 is inserted through through-holes 251 h provided in the pair of frames 251.

The arrowhead hook portion (hook portion) 260 is attached to the distal end side A1 of the support member 250, as shown in FIG. 43. The arrowhead hook portion 260 is substantially the same size and shape as the arrowhead hook portion 231 according to the first embodiment.

The forceps (jaw) 270 includes a first forceps piece 271 and a second forceps piece 272.

The first forceps piece 271 is a member that is provided on the lower side B2 of the forceps 270 and grasps the first arm 31. The first forceps piece 271 can open and close (rotate) the distal end side A1 in an opening/closing direction (rotational direction) R about a through-hole of a proximal end portion 271d described later. The first forceps piece 271 includes a first arm grasping portion 271a, an accommodating portion 271b, a pushing portion 271c, and a proximal end portion 271d in this order from the distal end side A1 to the proximal end side A2.

The first arm grasping portion 271a abuts on the back surface of the first grasping portion 312 so as to be fitted into the first grasping portion 312 of the first arm 31.

The accommodating portion 271b accommodates the first arm 31. The accommodating portion 271b is formed, for example, in a substantially cup-like shape with a recessed closed side R1.

The pushing portion 271c is a portion that is provided closer to the proximal end side A2 than the first arm grasping portion 271a and protrudes from the first forceps piece 271 toward the closing side R1 in the opening/closing direction R. After the clip unit 1 is loaded into the clip-introducing device 200D and the arm 3 is closed by the first forceps piece 271 and the second forceps piece 272, the pushing portion 271c pushes and breaks the separating portion 43 of the connection member 4 of the clip unit 1 together with a pushing portion 272c of the second forceps piece 272.

The proximal end portion 271d is provided on the proximal end side A2 of the first forceps piece 271 and partially arranged between the pair of frames 251. The proximal end portion 271d has a through-hole through which the rotation shaft member 252 can be inserted on the distal end side A1, and the proximal end side A2 is connected to the first operation wire 230Da. With this configuration, when the first operation wire 230Da is operated, the first forceps piece 271 can open and close (rotate) in the opening/closing direction R about the rotation shaft member 252 inserted through the through-hole provided on the distal end side A1.

The second forceps piece 272 is a member that is provided on the upper side B1 of the forceps 270 and grasps the second arm 32. The second forceps piece 272 can open and close (rotate) the distal end side A1 in an opening/closing direction (rotational direction) Q about a through-hole of a proximal end portion 272d described later. The second forceps piece 272 includes a second arm grasping portion 272a, an accommodating portion 272b, a pushing portion 272c, and a proximal end portion 272d in this order from the distal end side A1 to the proximal end side A2.

The second arm grasping portion 272a abuts on the back surface of the second grasping portion 322 so as to be fitted into the second grasping portion 322 of the second arm 32.

The accommodating portion 272b accommodates the second arm 32. The accommodating portion 272b is formed, for example, in a substantially cup-like shape with the closed side Q1 being recessed.

The pushing portion 272c is a portion that is provided closer to the proximal end side A2 than the second arm grasping portion 272a and protrudes from the second forceps piece 272 toward the closing side Q1 in the opening/closing direction Q. The pushing portion 272c pushes and breaks the separating portion 43 of the connection member 4 of the clip unit 1 together with the pushing portion 271c of the first forceps piece 271.

The proximal end portion 272d is provided on the proximal end side A2 of the second forceps piece 272, and is partially arranged between the pair of frames 251. The proximal end portion 272d has a through-hole through which the rotation shaft member 252 can be inserted on the distal end side A1, and the proximal end side A2 is connected to the second operation wire 230Db. With this configuration, when the second operation wire 230Db is operated, the second forceps piece 272 can open and close (rotate) in the opening/closing direction Q about the rotary shaft member 252 inserted through the through-hole provided on the distal end side A1.

Note that, in this embodiment, when the first forceps piece 271 rotates to the closing side R1 and the second forceps piece 272 rotates to the closing side Q1, the forceps 270 simultaneously closes toward the closing side (closing direction). Further, when the first forceps piece 271 rotates to the opening side R2 and the second forceps piece 272 rotates to the open side Q2, the forceps 270 opens toward the opening side (opening direction).

Figure 44:
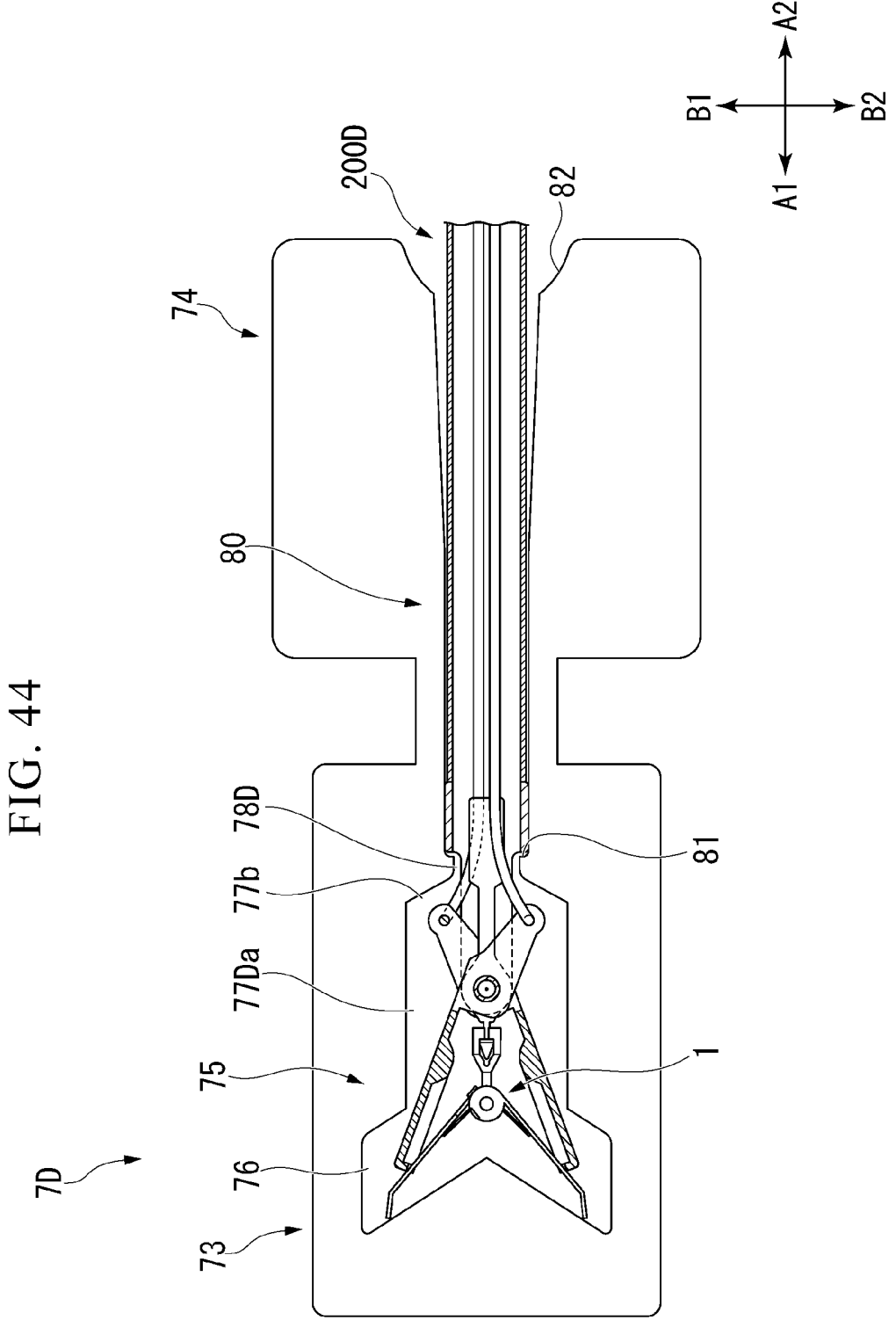
FIG. 44 is a schematic partial cross-sectional view of a cartridge for loading the clip unit into the clip-introducing device.

FIG. 44 is a schematic partial cross-sectional view of a cartridge 7D for loading the clip unit 1 into the clip-introducing device 200D.

In the cartridge 7D, as shown in FIG. 44, the width in the vertical direction B of a proximal end connecting portion enlarged diameter portion 77Da is larger than the width in the vertical direction B of the proximal end connecting portion enlarged diameter portion 77a compared to the cartridge 7 of the first embodiment, and is longer in the longitudinal direction A. Further, the length in the longitudinal direction A of the connection member housing portion 78D of the cartridge 7D is less than the length in the longitudinal direction A of the connection member housing portion 78 compared to the cartridge 7 of the first embodiment.

Next, the operation and action of the clip delivery device will be described.

Since the method of attaching (reloading) the clip unit 1 to the clip-introducing device 200D using the cartridge 7D is substantially the same as in the first embodiment, description thereof will be omitted. A clip release method of the clip delivery device will be described with reference to FIGS. 45 to 48.

<Arm 3 Opening Step>

Figure 45:
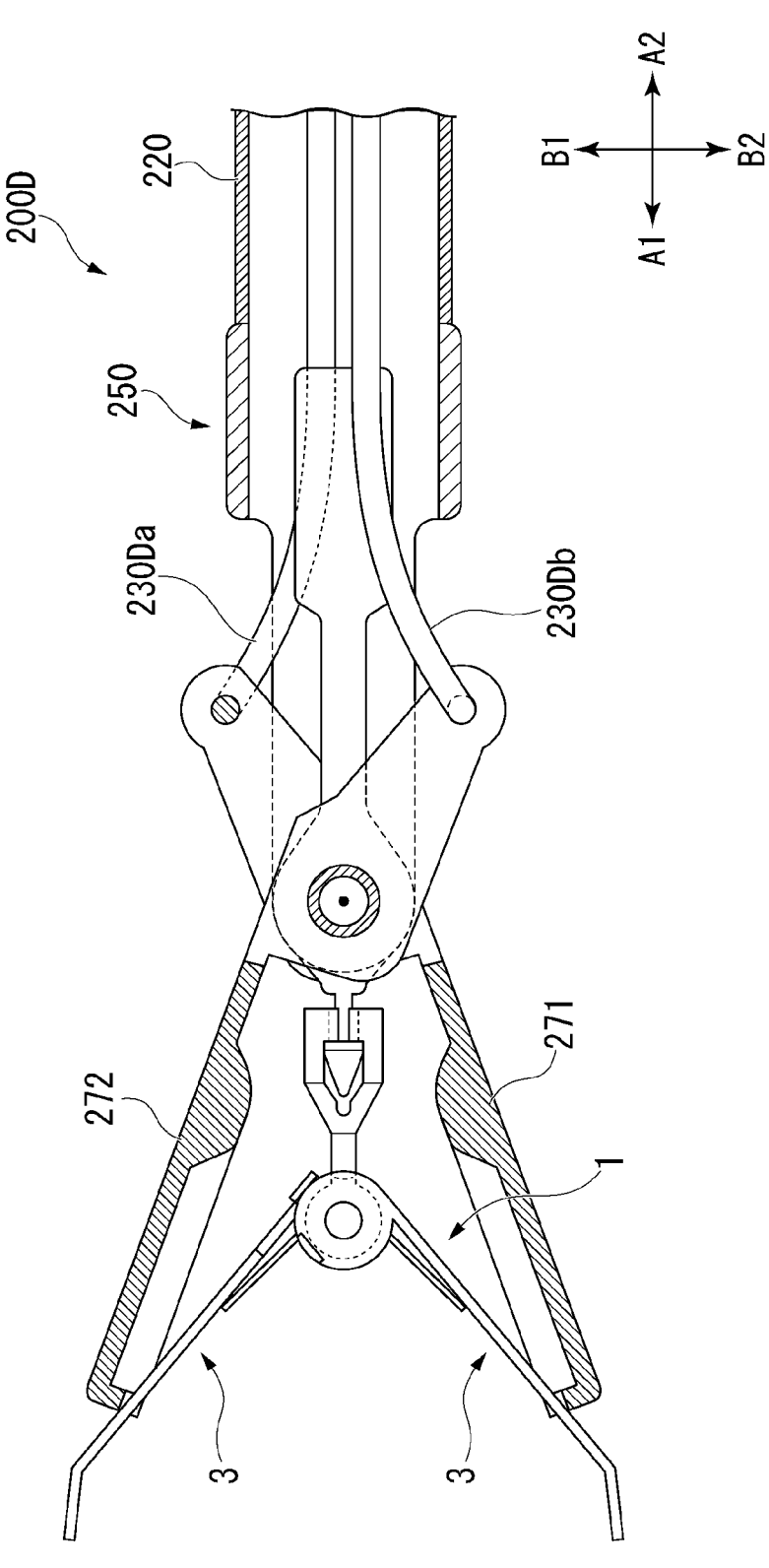
FIG. 45 is a view showing an arm-opening step for the clip unit.

FIG. 45 is a diagram showing the arm 3 opening step of the clip unit 1.

In a state where the forceps 270 of the clip-introducing device 200D is closed, the operator introduces the loaded clip unit 1 into the body via the treatment instrument insertion channel of the endoscope. Next, the operator advances the operation wire 230D by advancing the slider 242 along the operation portion main body 241. Then, the first forceps piece 271 and the second forceps piece 272 of the forceps 270 are opened to the opening side (opening direction) in the opening/closing direction. Then, the arm 3 held down by the forceps 270 is opened to the open side (opening direction) in the opening/closing direction by the self-expanding force of the biasing member 6 to be in the open state.

<Arm 3 Closing Step>

Figure 46:
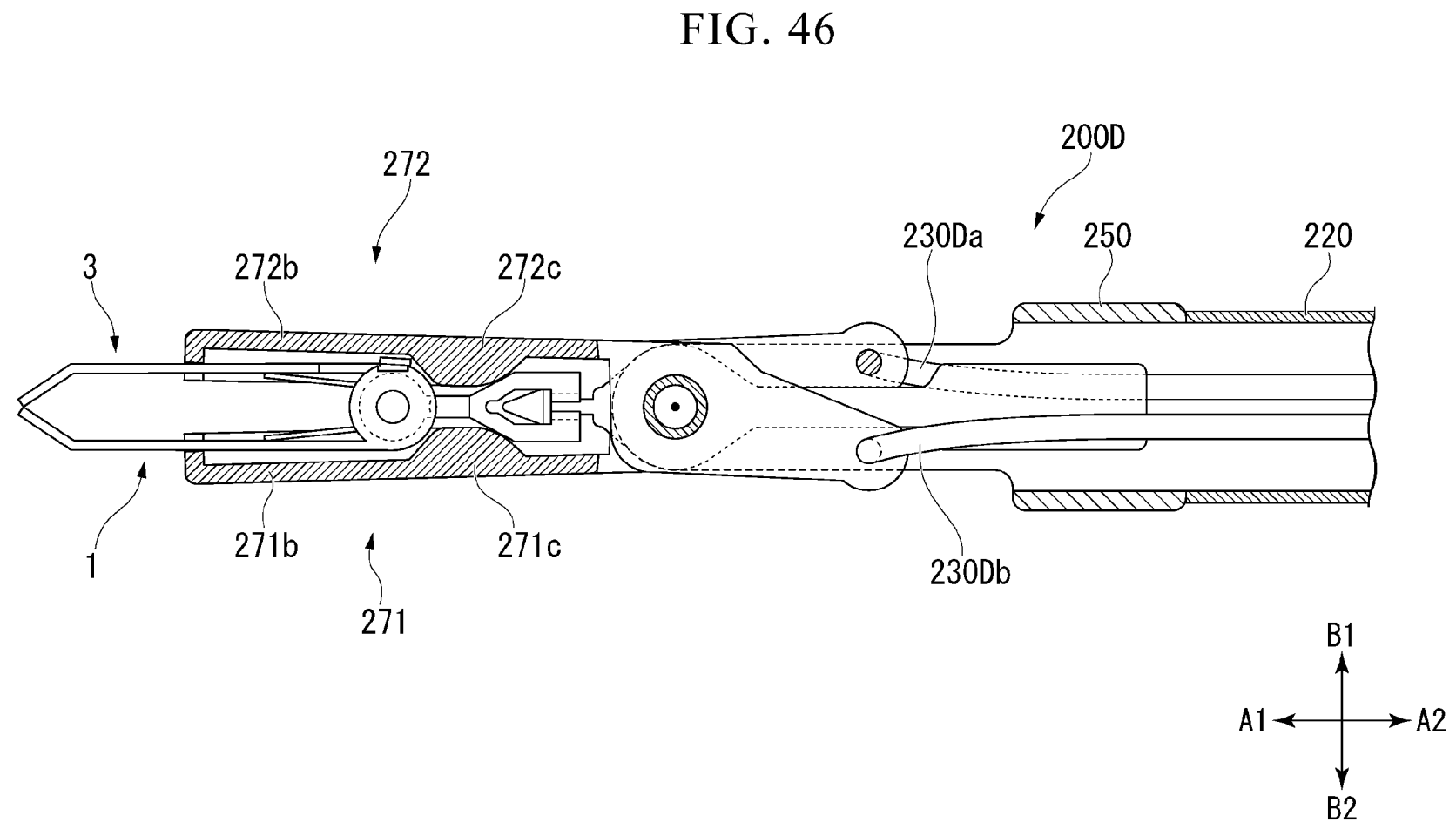

FIG. 46 is a diagram showing the arm 3 closing step of the clip unit 1.

The operator places the arm 3 of the clip unit 1 at the suturing position of the wound. The operator retracts the operation wire 230D by retracting the slider 242 along the operation portion main body 241. Then, the first forceps piece 271 and the second forceps piece 272 of the forceps 270 are closed to the closing side (closing direction) of the opening/closing direction. Then, the arm 3 is closed to the closing side (closing direction) in the opening/closing direction while being held down by the forceps 270 to the closed state.

<Re-Grasping Step>

After executing the arm 3 closing step, the operator operates the operation portion 240 again to open the forceps 270 in the re-grasping step. Thereby, it is also possible to rotate the arm 3 to shift the arm 3 to the open state and re-grasp the tissue.

<Lock-Setting Step>

Figure 47:
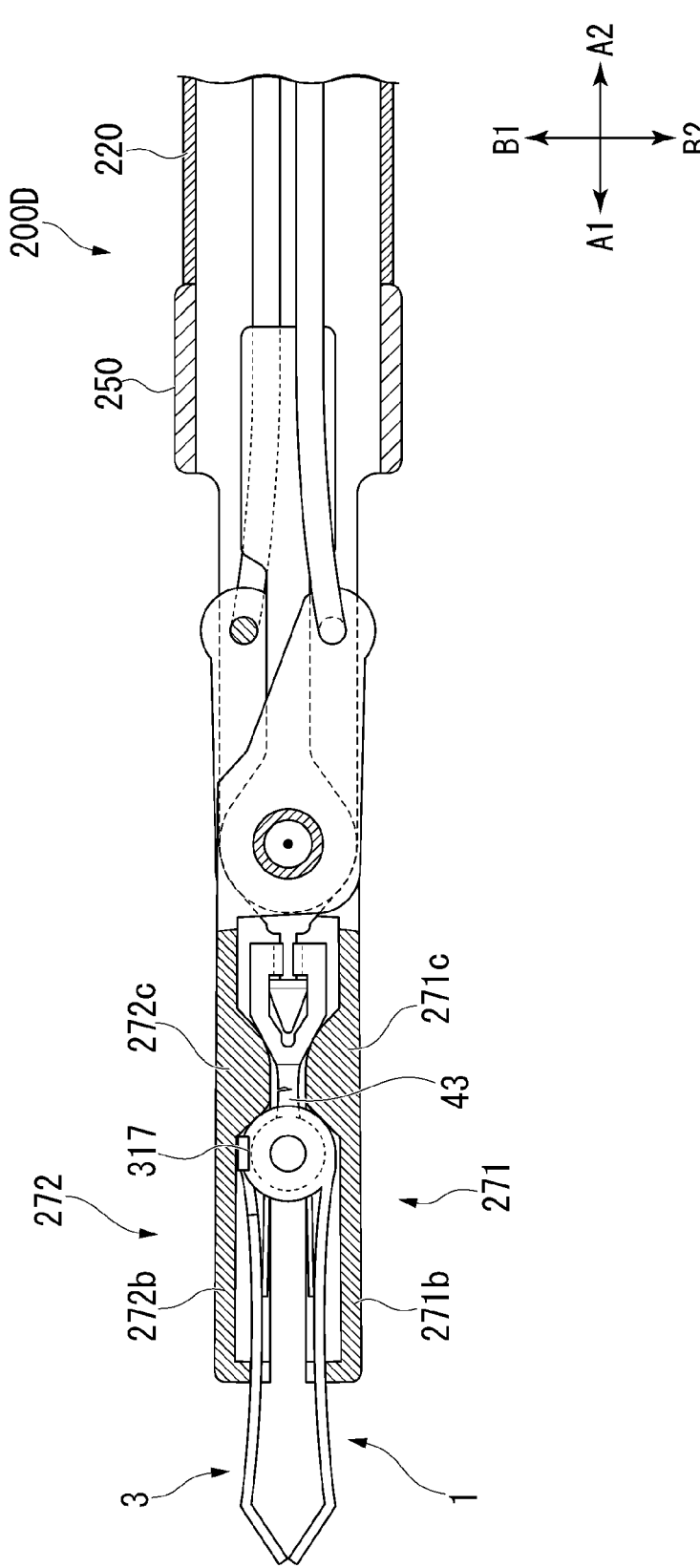
FIG. 47 is a diagram showing a lock-setting step for the clip unit.

FIG. 47 is a diagram showing a lock-setting step for the clip unit 1.

When the arm 3 is further pushed to the closing side by the forceps 270, the first grasping portion 312 and the second grasping portion 322 are elastically deformed. When the first grasping portion 312 and the second grasping portion 322 are elastically deformed, the protruding portion 327 is engaged with the notch portion 317 as shown in FIG. 47. With the above configuration, the rotation of the first arm 31 and the second arm 32 is relatively locked (restricted).

<Connection Release Step>

Figure 48:
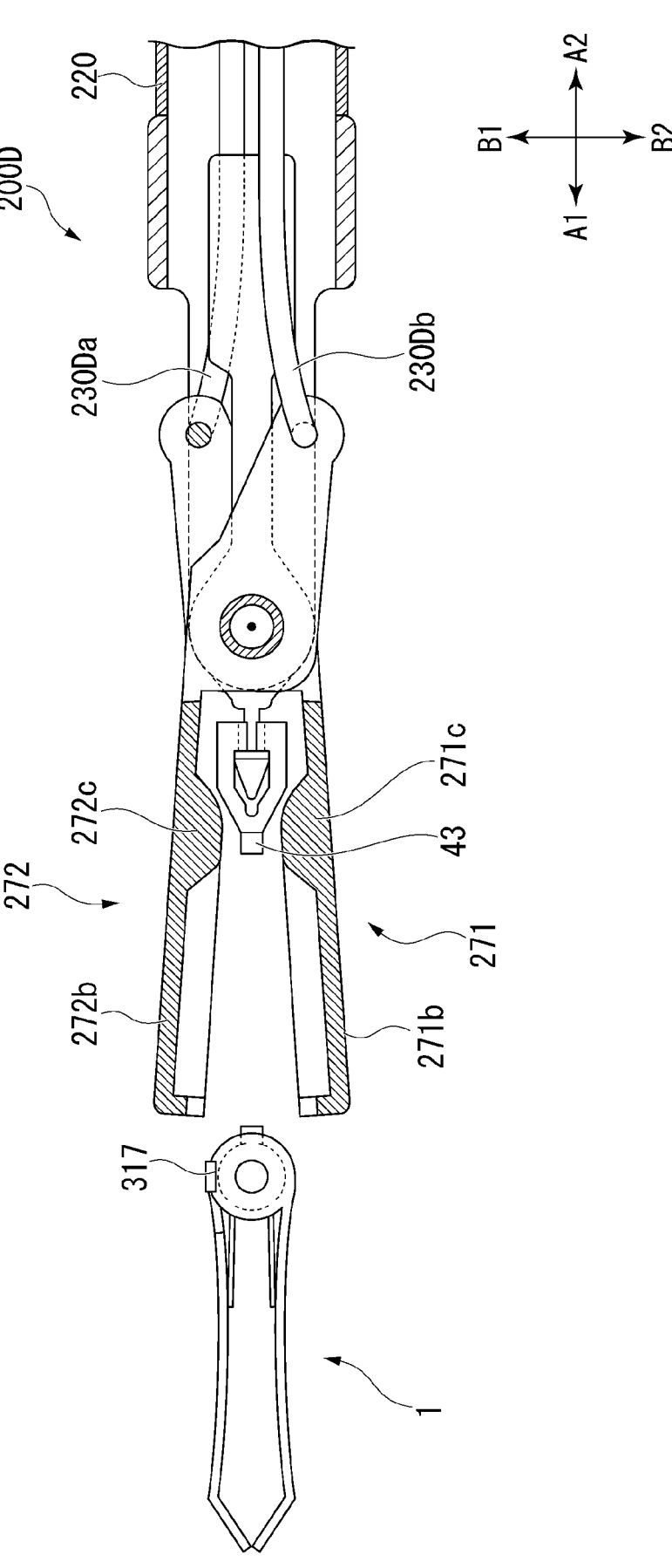
FIG. 48 is a diagram showing a connection release step for the clip unit.

FIG. 48 is a diagram showing a connection release step for the clip unit 1.

The operator further retracts the slider 242 along the operation portion main body 241 to further close the forceps 270 to the closing side. Then, the pushing portion 271c of the first forceps piece 271 and the pushing portion 272c of the second forceps piece 272 push the separating portion 43 of the connection member 4 of the clip unit 1. As shown in FIG. 48, the separating portion (breaking portion) 43 is broken by applying a predetermined amount of breaking force by the pushing portions 271c and 272c. The operator withdraws the sheath 220 and leaves the clip unit 1 with the tissue ligated in the body.

According to the clip unit 1 and the clip release method using the clip unit 1 of the present embodiment, the arm 3 is pressed to the closed side by the forceps 270 to grasp the tissue, so the tissue can be grasped more reliably.

In addition, in this embodiment, since the arrowhead hook portion 260 that connects the clip unit 1 is provided directly on the distal end side of the sheath 220, the operator wants to rotate the clip unit 1 in the central axis direction according to the tissue. In this case, the sheath 220 can be easily grasped and rotated for adjustment.

As described above, the fifth embodiment of the present disclosure has been described in detail with reference to the drawings, but the specific configuration is not limited to this embodiment, and design changes and the like are included within the scope of the present disclosure. Also, the constituent elements shown in the above-described embodiment and modifications can be combined as appropriate.

Sixth Embodiment

Next, a sixth embodiment of the present disclosure will be described with reference to FIGS. 49 to 53. In the following description, the same reference numerals are given to the same configurations as those already described, and redundant descriptions will be omitted. It should be noted that each of the following embodiments differs in the clip unit from the third embodiment. Therefore, in the following description, the differences from the third embodiment will be mainly described.

Figure 49:
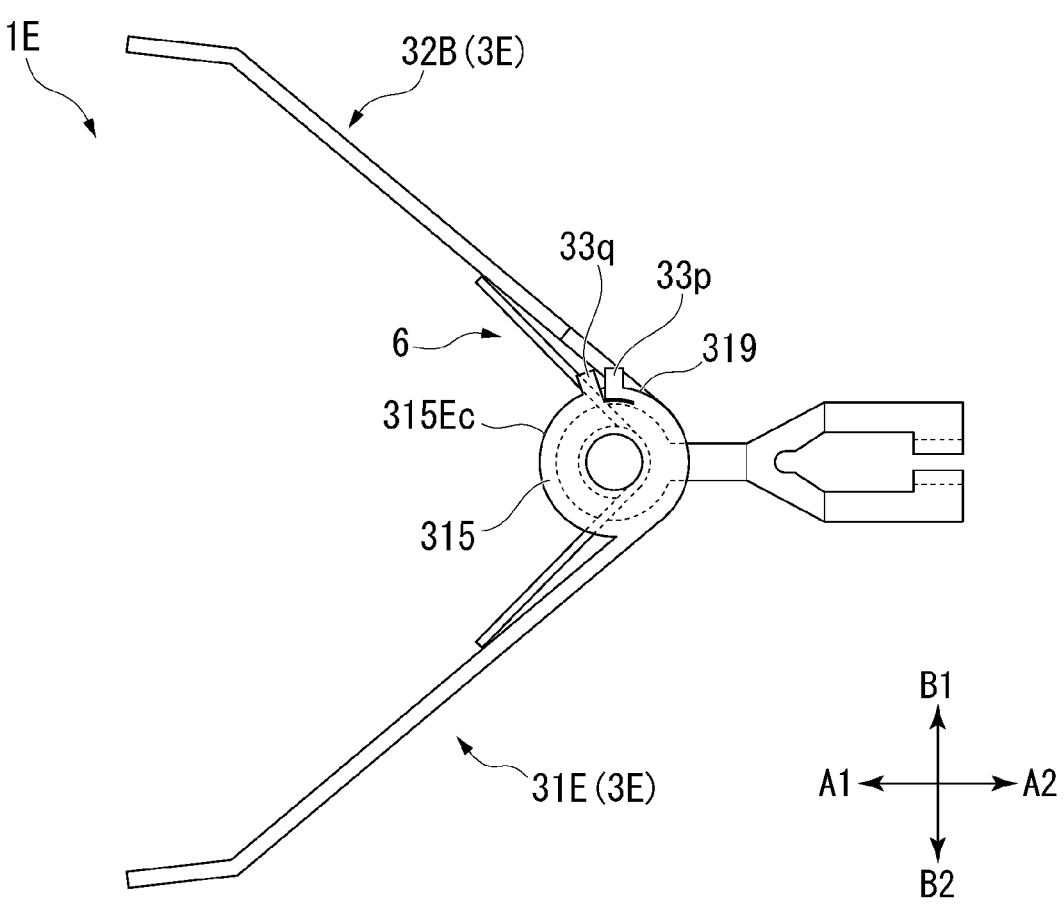
FIG. 49 is a side view showing an open state of an arm provided in a clip unit of a clip delivery device according to a sixth embodiment.
Figure 50:
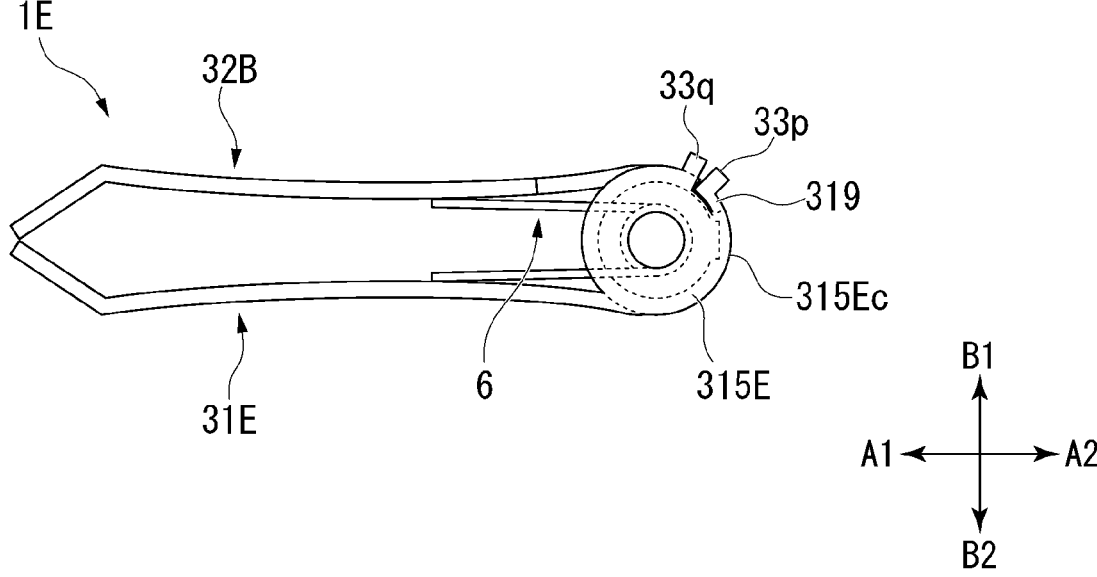
FIG. 50 is a side view showing a closed state of an arm provided in the clip unit.

FIG. 49 is a side view showing the open state of the arm 3E provided on the clip unit 1E. FIG. 50 is a side view showing the closed state of the arm 3E provided on the clip unit 1E.

A clip unit (endoscopic treatment instrument) 1E according to the sixth embodiment of the present disclosure, as shown in FIG. 49, does not have an engaging hook portion as compared with the clip unit 1B of the third embodiment. Also, the clip unit 1E has a different arm 3E from the arm 3B of the clip unit 1B. The arm 3E has a first arm 31E and a second arm 32B.

The first arm 31E includes a leaf spring portion 319 provided on the first rotation portion 315E with a first grasping portion (first unlocking portion) 33p protruding outward from the peripheral edge of the first rotation portion 315E. The outer side from the peripheral edge of the first rotation portion 315E is the direction away from the center of the first rotation portion 315E.

In addition, the first arm 31E includes a second grasping portion (second unlocking portion) 33q protruding outward from the peripheral edge of the first rotation portion 315E on the first rotation side surface 315Ec of the first rotation portion 315E. The first grasping portion 33p and the second grasping portion 33q are provided at the edge of the notch portion of the leaf spring portion 319 to form a grasping structure of the clip unit 1E. Also, the first grasping portion 33p and the second grasping portion 33q are arranged so as to be adjacent to the first rotation side surface 315Ec when viewed from the width direction C, as shown in FIG. 49.

Next, the operation and action of the clip delivery device will be described. The method of attaching (reloading) the clip unit 1E to the clip-introducing device using the cartridge and the method of releasing the clip of the clip delivery device are the same as those in the above-described embodiment, and therefore will be described. In addition, in this embodiment, the clip-introducing device 200D described in the fifth embodiment is used as the clip-introducing device loaded in the clip unit 1E.

Figure 52:
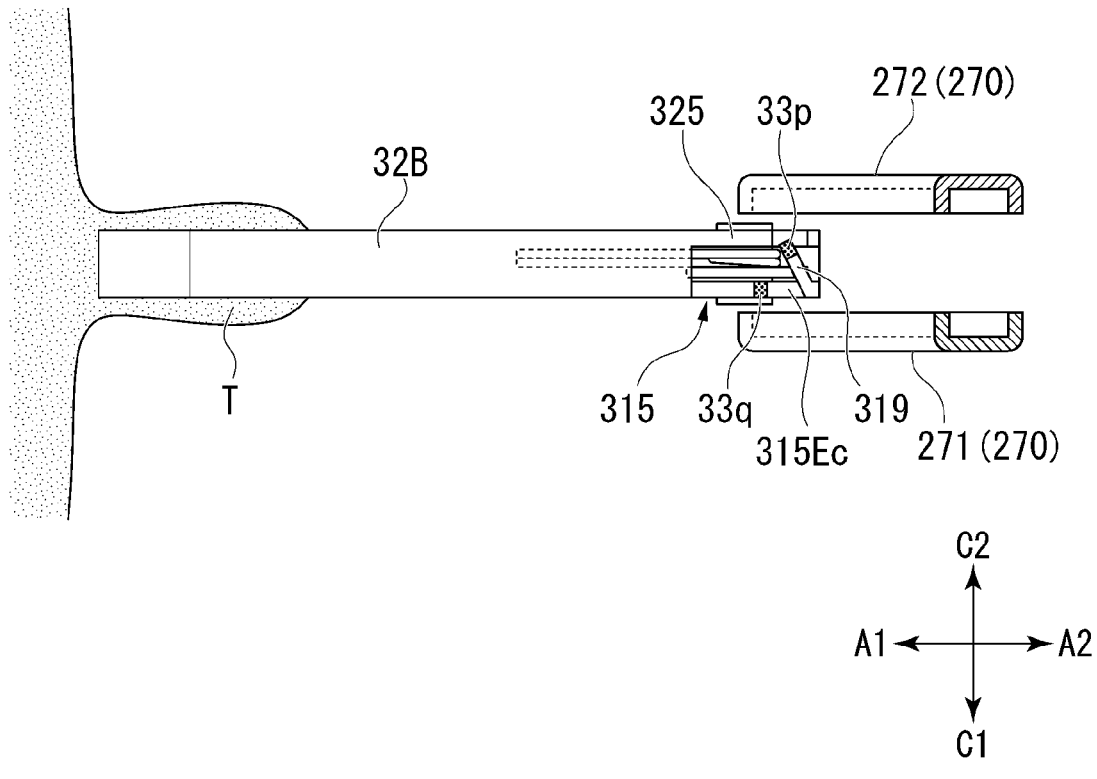
FIG. 52 is a plan view of the clip unit of FIG. 51 as viewed from above in a vertical direction.
Figure 53:
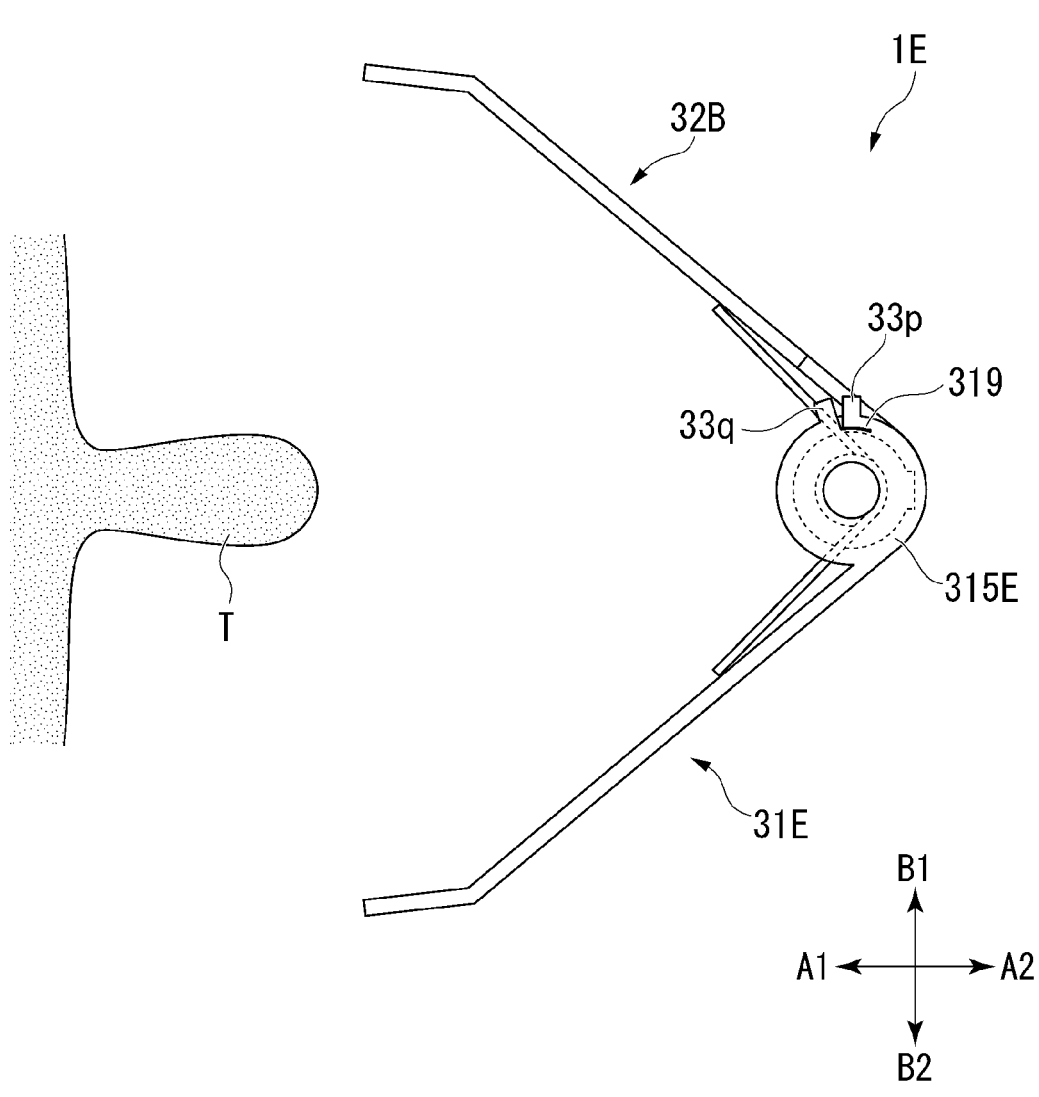
FIG. 53 is a diagram showing a state in which the clip unit in the closed state is unlocked.

The unlocking step by the grasping structure of the first grasping portion 33p and the second grasping portion 33q will be described with reference to FIGS. 51 to 53.

<Unlock Step>

Figure 51:
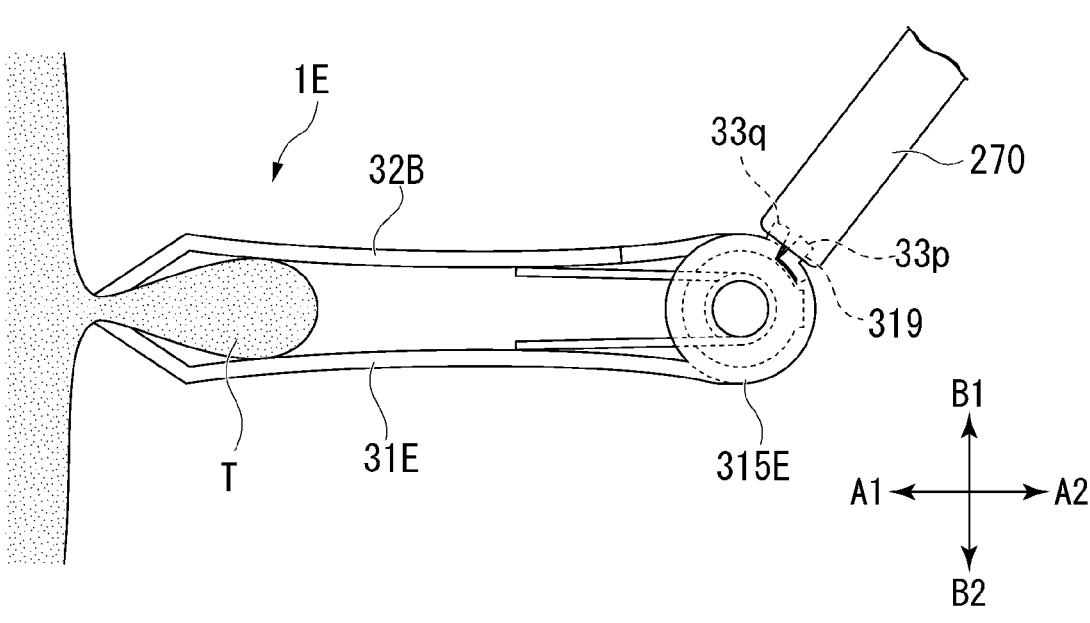
FIG. 51 is a side view of the clip unit in a closed state grasping tissue.

FIG. 51 is a side view of the clip unit 1E in the closed state grasping the tissue T. FIG. 52 is a plan view of the clip unit 1E of FIG. 51 viewed from the upper side B1 in the vertical direction B. FIG. 53 is a diagram showing a state in which the closed clip unit 1E is unlocked.

After executing the connection release step described in the above embodiment, the operator can use the forceps 270 of the clip-introducing device 200D to grasp the tissue T and release the locked clip unit 1E again. As shown in FIGS. 51 and 52, the operator arranges the forceps 270 of the clip-introducing device 200D between the forceps 270 so as to overlap the first grasping portion 33*p* and the second grasping portion 33*q* when viewed from the width direction C. In this state, the operator retracts the slider 242 along the operation portion main body 241 to further close the forceps 270 to the closing side.

The first grasping portion 33*p* and the second grasping portion 33*q* are pushed toward the central axis of the clip unit 1E by the forceps 270. A leaf spring portion 319 that engages with the through-hole 329 of the second rotation portion 325 and has the first grasping portion 33*p* is removed from the through-hole 329. Then, the locked (restricted) rotation of the first arm 31E and the second arm 32B is released. As shown in FIG. 53, the arm 3 is opened to the opening side (opening direction) in the opening/closing direction by the self-expanding force of the urging member 6 to be in the open state.

In this embodiment, the clip unit 1E can be unlocked. Therefore, when the clip unit 1E is placed at a position not desired by the operator, the lock of the clip unit 1E can be released.

As described above, the sixth embodiment of the present disclosure has been described in detail with reference to the drawings, but the specific configuration is not limited to this embodiment, and design changes and the like are included within the scope of the present disclosure. Also, the constituent elements shown in the above-described embodiment and modifications can be combined as appropriate.

In any of the above-described embodiments, the clip unit, clip delivery device and clip release method of the present disclosure can be securely locked while grasping the tissue without obstructing the suturing operation position.

What is claimed is:

1. A clip system, comprising:
a tubular applicator;
a first arm including a first rotation portion, the first arm rotating around the first rotation portion as a center of rotation;
a second arm including a second rotation portion connected to the first rotation portion, the second arm rotating around the second rotation portion as a second center of rotation; and
a connector, the connector including:
a first connecting portion connected to the first arm and the second arm; and
a second connecting portion configured to connect to the tubular applicator;
wherein:
the first rotation portion includes an engaged portion;
the second rotation portion includes an engaging portion configured to slide relative to the first rotation portion as the second arm rotates;
when the clip unit is pulled relative to the tubular applicator to which the clip unit is connectable, the first rotation portion and the second rotation portion are configured to lock a relative rotation of the first arm and the second arm by engagement between the engaging portion and the engaged portion;
the first connecting portion is disposed between the first arm and the second arm in a direction intersecting at least one of an opening or closing direction of the first arm and the second arm;
the engaged portion includes a notch provided on a side surface of the first rotation portion;
the engaging portion includes an elastic protrusion provided on the second rotation portion and protruding toward the first rotation portion; and the elastic protrusion is biased in a direction toward the side surface of the first rotation portion.

2. The clip unit according to claim 1, further comprising:
a biasing portion configured to bias the first arm and the second arm in an opening direction in which a distal end portion of the first arm and a distal end portion of the second arm are separated from each other.

3. The clip unit according to claim 1, wherein the connector further comprises:
a separating portion separably connecting the first connecting portion and the second connecting portion.

4. The clip unit according to claim 1, further comprising:
a connecting pin connecting the first rotation portion and the second rotation portion.

5. The clip unit according to claim 1, wherein at least one of the first arm and the second arm has a stopper protruding in a width direction perpendicular to a longitudinal axis direction, and wherein, when the clip unit is pulled relative to the tubular applicator to which the clip unit is connectable, with the stopper being in contact with the tubular applicator, the first rotation portion and the second rotation portion are configured to lock a relative rotation of the first arm and the second arm by engagement between the engaging portion and the engaged portion.

6. The clip unit according to claim 1, wherein the first arm and the second arm rotate by being accommodated in the applicator, and wherein the first rotation portion and the second rotation portion are configured to lock relative rotation of the first arm and the second arm in a state where the first rotation portion and the second rotation portion are accommodated in the applicator.

7. The clip unit according to claim 1, wherein:
the first arm and the second arm are configured to be relatively rotatable in a closed state; and
the first arm and the second arm are configured to lock relative rotation when the first arm and the second arm are elastically deformed in the closed state.

8. A clip device, comprising:
an applicator including a sheath extending in a longitudinal direction and a wire passing through the sheath; and
a clip unit including:
a first arm provided at a distal end of the wire, the first arm having a first rotation portion and rotating around the first rotation portion as a center of rotation; and
a second arm provided with a second rotation portion connected to the first rotation portion and rotating around the second rotation portion as a second center of rotation, wherein:
the first rotation portion includes an engaged portion;
the engaged portion is a notch provided on a side surface of the first rotation portion;
the second rotation portion includes an engaging portion configured to slide relative to the first rotation portion as the second arm rotates;
the engaging portion is an elastic protrusion provided on the second rotation portion and protruding toward the first rotation portion;
the elastic protrusion is biased in a direction toward the side surface of the first rotation portion; and
when the clip unit is pulled relative to the applicator, the first rotation portion and the second rotation portion are configured to lock a relative rotation of the first arm and the second arm by engagement between the engaging portion and the engaged portion.

9. The clip device according to claim 8, wherein a distal end of the wire includes a hook portion, wherein the first arm further includes a first through-hole provided in a center of the first rotation portion and through which the hook portion is inserted, and a first groove formed from a periphery to the first through-hole, wherein the second arm further includes a second through-hole provided in a center of the second rotation portion and through which the hook portion is inserted, and a second groove formed from a periphery to the second through-hole, and wherein in a closed state, the first rotation portion and the second rotation portion lock the rotation of the first arm and the second arm, and the hook portion passes through the first groove and the second groove to separate the applicator and the clip unit.

10. The clip device according to claim 8, further comprising:
    a biasing portion biasing the first arm and the second arm in an opening direction in which a distal end portion of the first arm and a distal end portion of the second arm are separated from each other.

11. The clip device according to claim 8, wherein at least one of the first arm and the second arm protrudes in a width direction perpendicular to the longitudinal direction and has a locking portion locking at a distal opening edge of the sheath.

12. The clip device according to claim 8, further comprising:
    a connection member including:
    a first connecting portion connected to the applicator;
    a second connecting portion connected to the first arm and the second arm; and
    a separating portion separably connecting the first connecting portion and the second connecting portion.

13. The clip device according to claim 8, further comprising:
    a connecting pin connecting the first rotation portion and the second rotation portion.

14. The clip device according to claim 8, wherein the first arm and the second arm rotate by being accommodated in the applicator, and wherein the first rotation portion and the second rotation portion are configured to lock relative rotation of the first arm and the second arm in a state where the first rotation portion and the second rotation portion are accommodated in the applicator.

\* \* \* \* \*